US009528536B2

United States Patent
Bally et al.

(10) Patent No.: US 9,528,536 B2
(45) Date of Patent: *Dec. 27, 2016

(54) SECURE EQUIPMENT TRANSFER SYSTEM

(71) Applicant: Nexxspan Healthcare, LLC, Lithia, FL (US)

(72) Inventors: Alexander Bally, Marston Mills, MA (US); Eric Colburn, Pittsburgh, PA (US)

(73) Assignee: Nexxspan Healthcare, LLC, Lithia, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/686,439

(22) Filed: Apr. 14, 2015

(65) Prior Publication Data

US 2015/0216606 A1  Aug. 6, 2015

Related U.S. Application Data

(63) Continuation-in-part of application No. 14/064,345, filed on Oct. 28, 2013, now Pat. No. 9,404,616, which
(Continued)

(51) Int. Cl.
*A61G 7/10* (2006.01)
*A47B 71/00* (2006.01)
(Continued)

(52) U.S. Cl.
CPC .............. *F16B 2/10* (2013.01); *A61G 7/012* (2013.01); *A61G 12/005* (2013.01);
(Continued)

(58) Field of Classification Search
CPC .. A61G 7/1025; A61G 7/1055; A61G 7/1057; A61G 7/1073; A61G 12/005; A61G 12/008; A61G 2203/80; A61F 5/045; A61M 5/1415; F16M 2200/02
(Continued)

(56) References Cited

U.S. PATENT DOCUMENTS

| 2,409,432 A | 10/1946 | Hubbard |
| 2,460,244 A | 1/1949 | Strauss |

(Continued)

FOREIGN PATENT DOCUMENTS

| NL | 2000571 | 10/2008 |
| WO | 2016167817 | 10/2016 |

OTHER PUBLICATIONS

Bally, Alexander; Issue Notification for U.S. Appl. No. 13/104,531, filed May 10, 2011, mailed Oct. 23, 2013, 1 pg.
(Continued)

*Primary Examiner* — Tan Le
(74) *Attorney, Agent, or Firm* — Taylor English Duma LLP

(57) ABSTRACT

Disclosed is a transfer system for a patient care apparatus, the transfer system including: a transfer device including a first docking cup and a second docking cup, each of the first docking cup and the second docking cup sized to accept a receiver; and a security mechanism enclosed within the transfer device and including a first security lever and a second security lever, the first security lever positioned to disengage a first receiver in the first docking cup when a second receiver is received within the second docking cup, and the second security lever positioned to disengage the second receiver in the second docking cup when the first receiver is received within the first docking cup.

27 Claims, 58 Drawing Sheets

Related U.S. Application Data is a continuation-in-part of application No. 13/104,531, filed on May 10, 2011, now Pat. No. 8,579,244.

(60) Provisional application No. 61/332,918, filed on May 10, 2010.

(51) Int. Cl.
    *F16M 13/00* (2006.01)
    *F16B 2/10* (2006.01)
    *A61G 7/012* (2006.01)
    *A61G 12/00* (2006.01)
    *A61G 7/00* (2006.01)
    *A61G 7/05* (2006.01)
    *A61M 5/14* (2006.01)

(52) U.S. Cl.
    CPC ......... *A61M 5/1417* (2013.01); *A61G 7/0015* (2013.01); *A61G 7/0506* (2013.01); *A61G 7/1025* (2013.01); *A61G 7/1073* (2013.01); *A61G 2203/80* (2013.01); *A61M 5/1415* (2013.01); *F16M 13/00* (2013.01)

(58) Field of Classification Search
    USPC .......... 248/125.2, 125.7, 314, 276.1, 288.51; 5/503.1, 658; 403/321, 322.1, 325, 326, 403/334; 414/343, 349
    See application file for complete search history.

(56) References Cited

U.S. PATENT DOCUMENTS

| | | | |
|---|---|---|---|
| D262,237 S | 12/1981 | Stauber | |
| 4,511,158 A | 4/1985 | Varga et al. | |
| 4,945,592 A | 8/1990 | Sims et al. | |
| D339,195 S | 9/1993 | Nash et al. | |
| 5,306,109 A | 4/1994 | Kreuzer et al. | |
| 5,366,191 A | 11/1994 | Bekanich | |
| 5,527,125 A | 6/1996 | Kreuzer et al. | |
| D381,745 S | 7/1997 | Owens | |
| 5,898,961 A | 5/1999 | Ambach et al. | |
| 7,065,812 B2 | 6/2006 | Newkirk et al. | |
| 7,254,850 B2 | 8/2007 | Newkirk et al. | |
| 7,258,310 B2 | 8/2007 | Norris | |
| 7,314,200 B2 | 1/2008 | Bally | |
| 7,418,749 B2 | 9/2008 | Graham et al. | |
| 7,661,641 B2 | 2/2010 | Wong et al. | |
| 7,676,865 B2 * | 3/2010 | Graham ............... | A61G 7/0503 248/158 |
| 7,735,788 B2 | 6/2010 | Newkirk et al. | |
| 7,748,672 B2 | 7/2010 | Walke | |
| 7,789,361 B2 * | 9/2010 | Bally ...................... | A61G 7/05 248/124.2 |
| 7,798,456 B2 | 9/2010 | Newkirk et al. | |
| 7,845,601 B1 | 12/2010 | Culpepper et al. | |
| 7,865,983 B2 | 1/2011 | Newkirk et al. | |
| 8,104,729 B2 * | 1/2012 | Walke .................. | A61G 12/002 248/125.1 |
| D655,408 S | 3/2012 | Bally | |
| D655,409 S | 3/2012 | Bally | |
| 8,579,244 B2 | 11/2013 | Bally | |
| 9,404,616 B2 | 8/2016 | Bally | |
| 2005/0253034 A1 * | 11/2005 | Bally ....................... | A61G 5/10 248/276.1 |
| 2006/0179571 A1 | 8/2006 | Newkirk | |
| 2006/0242763 A1 | 11/2006 | Graham et al. | |
| 2006/0249641 A1 | 11/2006 | Bally et al. | |
| 2007/0069093 A1 | 3/2007 | Graham et al. | |
| 2007/0267550 A1 | 11/2007 | Blankenship et al. | |
| 2008/0149788 A1 | 6/2008 | Wong et al. | |
| 2008/0217910 A1 | 9/2008 | Walke et al. | |
| 2009/0065668 A1 | 3/2009 | Walke | |
| 2011/0272538 A1 | 11/2011 | Bally | |
| 2014/0048661 A1 | 2/2014 | Bally | |
| 2016/0153611 A1 | 6/2016 | Bally | |

OTHER PUBLICATIONS

Bally, Alexander; Non-Final Office Action for U.S. Appl. No. 13/104,531, filed May 10, 2011, mailed Apr. 23, 2013, 15 pgs.

Bally, Alexander; Notice of Allowance for U.S. Appl. No. 13/104,531, filed May 10, 2011, mailed Aug. 22, 2013, 12 pgs.

Bally, Alexander; Restriction Requirement for U.S. Appl. No. 13/104,531, filed May 10, 2011, mailed Feb. 5, 2013, 6 pgs.

Bally, Alexander; U.S. Patent Application entitled: Secure Equipment Transfer System, having U.S. Appl. No. 13/104,531, filed May 10, 2011, 81 pgs.

Bally, Alexander; Non-Final Office Action for U.S. Appl. No. 14/064,345, filed Oct. 28, 2013, mailed Apr. 6, 2015, 14 pgs.

Bally, Alexander; U.S. Continuation Application entitled: Secure Equipment Transfer System, having U.S. Appl. No. 14/064,345, filed Oct. 28, 2013, 89 pgs.

Bally, Alex; International Search Report and Written Opinion for PCT/US2013/067007, filed Oct. 28, 2013, mailed Mar. 10, 2014, 8 pgs.

Bally, Alex; PCT Application entitled: Secure Equipment Transfer System, having serial No. PCT/US2013/067007, filed Oct. 28, 2013, 71 pgs.

Bally, Alexander; Issue Notification for U.S. Appl. No. 29/393,210, filed Jun. 1, 2011, mailed Feb. 15, 2012, 1 pg.

Bally, Alexander; Non-Final Office Action for U.S. Appl. No. 29/393,210, filed Jun. 1, 2011, mailed Oct. 26, 2011, 7 pgs.

Bally, Alexander; Notice of Allowance for U.S. Appl. No. 29/393,210, filed Jun. 1, 2011, mailed Nov. 23, 2011, 5 pgs.

Bally, Alexander; U.S. Design Application entitled: Symmetrical Transfer Device, having U.S. Appl. No. 29/393,210, filed Jun. 1, 2011, 8 pgs.

Bally, Alexander; Issue Notification for U.S. Appl. No. 29/393,211, filed Jun. 1, 2011, mailed Feb. 15, 2012, 1 pg.

Bally, Alexander; Non-Final Office Action for U.S. Appl. No. 29/393,211, filed Jun. 1, 2011, mailed Oct. 25, 2011, 6 pgs.

Bally, Alexander; Notice of Allowance for U.S. Appl. No. 29/393,211, filed Jun. 1, 2011, mailed Nov. 25, 2011, 5 pgs.

Bally, Alexander; U.S. Design Application entitled: Asymetrical Transfer Device, having U.S. Appl. No. 29/393,211, filed Jun. 1, 2011, 8 pgs.

Bally, Alexander; U.S. Provisional Patent Application Entitled: Secure Equipment Transfer System, U.S. Appl. No. 61/332,918, filed May 10, 2010; 63 pgs.

IMEC-TRUMPF North America, article located at <www.us.trumpf.com/products/,,,/imec.html>, accessed on Sep. 1, 2010, 1 pg.

Bally, Alexander; Final Office Action for U.S. Appl. No. 14/064,345, filed Oct. 28, 2013, mailed Jul. 15, 2015, 9 pgs.

Bally, Alex; International Search Report and Written Opinion for PCT Application No. PCT/US15/27300, filed Apr. 23, 2015, mailed Sep. 1, 2015, 13 pgs.

Bally, Alexander; Notice of Allowance for U.S Appl. No. 14/064,345, filed Oct. 28, 2013, mailed Nov. 9, 2015, 10 pgs.

Bally, Alexander; Issue Notification for U.S. Appl. No. 14/064,345, filed Oct. 28, 2013, mailed Feb. 24, 2016, 1 pg.

Bally, Alexander; Notice of Allowance for U.S Appl. No. 14/064,345, filed Oct. 28, 2013, mailed Mar. 25, 2016, 10 pgs.

Bally, Alexander; U.S. Patent Application entitled: Secure Equipment Transfer System having U.S. Appl. No. 15/019,323, filed Feb. 9, 2016, 76 pgs.

Bally, Alexander; U.S. Patent Application entitled: Sacrificial Mechanical Link having U.S. Appl. No. 15/049,466, filed Feb. 22, 2016, 56 pgs.

Bally, Alexander; U.S Patent Application entitled: Transfer System With Sacrificial Mechanical Link having U.S. Appl. No. 15/049,477, filed Feb. 22, 2016, 57 pgs.

Bally, Alexander; Issue Notification for U.S. Appl. No. 14/064,345, filed Oct. 28, 2013, mailed Jul. 13, 2016, 1 pg.

(56) References Cited

OTHER PUBLICATIONS

Bally, Alex; International Preliminary Report on Patentability for PCT/US2013/067007, filed Oct. 28, 2013, mailed May 3, 2016, 6 pgs.

Bally, Alexander; Non-Final Office Action for U.S. Appl. No. 15/019,323, filed Feb. 9, 2016, mailed Oct. 18, 2016; 21 pgs.

* cited by examiner

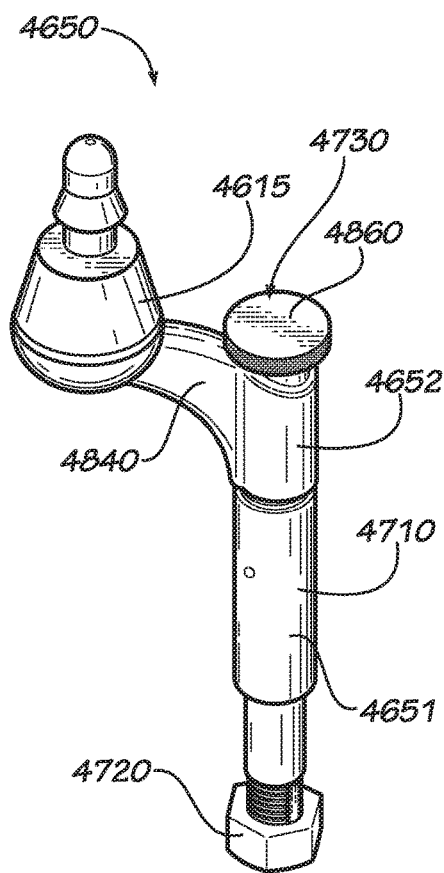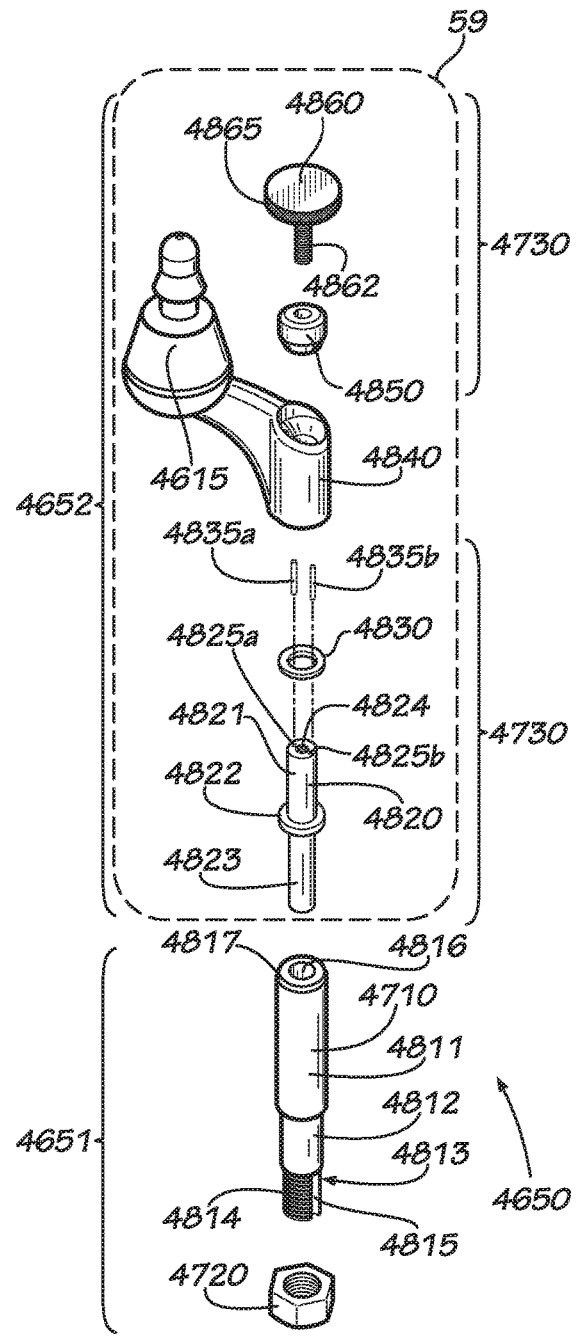
FIG. 47
FIG. 48

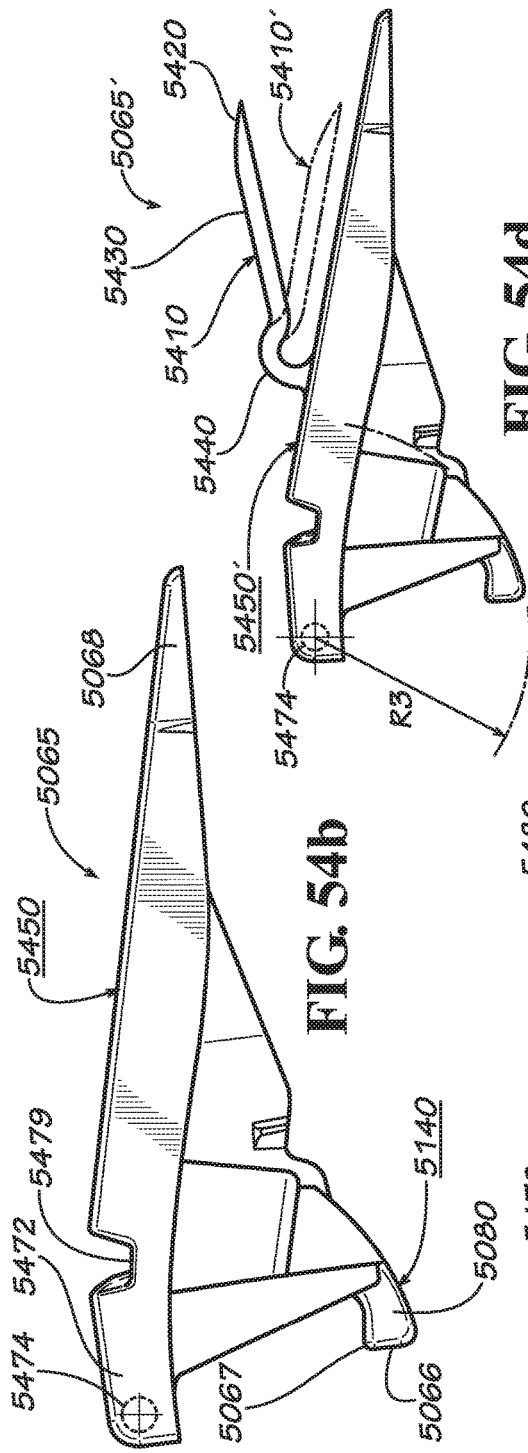
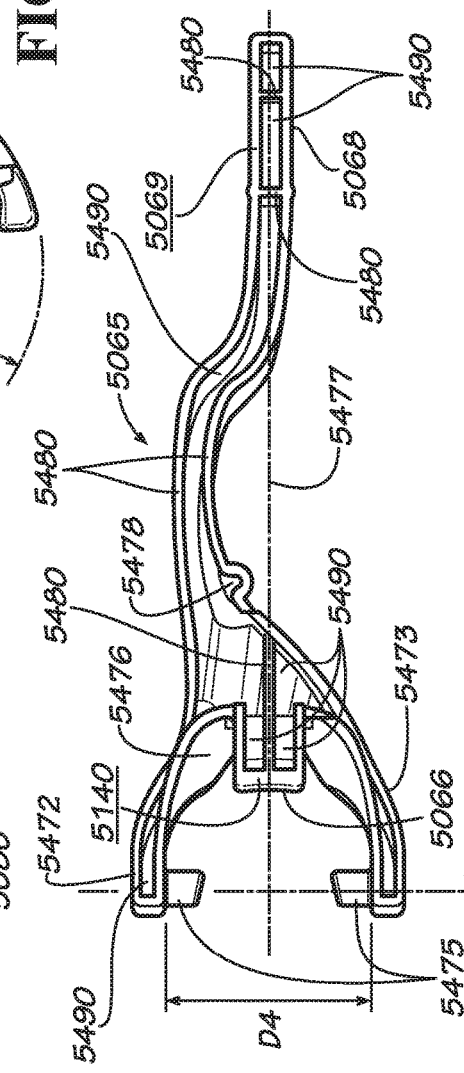
FIG. 54b
FIG. 54d
FIG. 54c

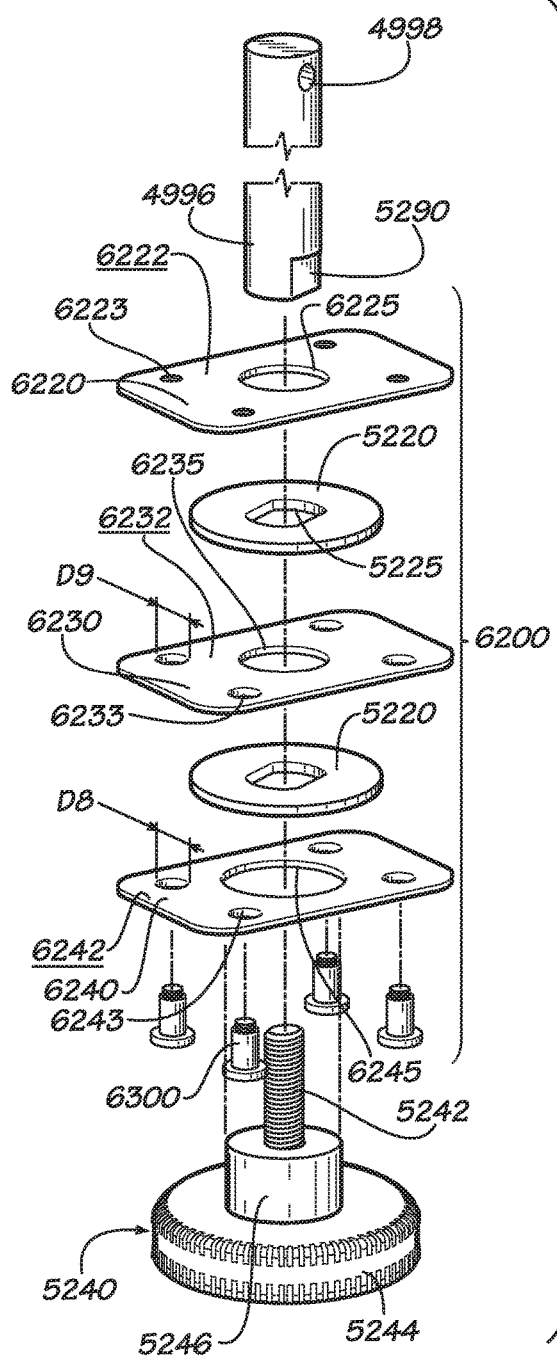
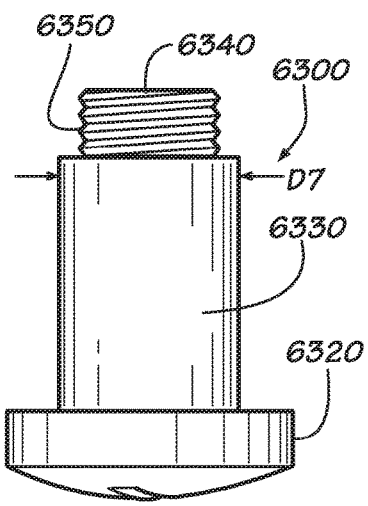
FIG. 63
FIG. 62a
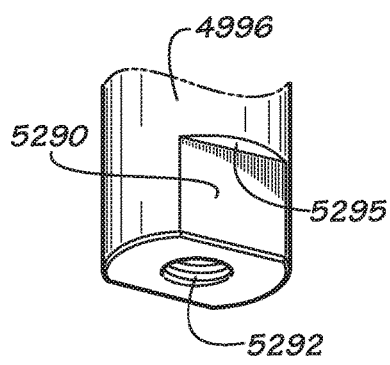
FIG. 62b

SECURE EQUIPMENT TRANSFER SYSTEM

REFERENCE TO RELATED APPLICATIONS

This application is a continuation-in-part of U.S. application Ser. No. 14/064,345, filed Oct. 28, 2013, which is a continuation-in-part of U.S. patent application Ser. No. 13/104,531, filed May 10, 2011, which issued into U.S. Pat. No. 8,579,244 on Nov. 12, 2013, which claims the benefit of U.S. Provisional Application No. 61/332,918, filed May 10, 2010, each of which are hereby specifically incorporated by reference herein in their entireties.

TECHNICAL FIELD

The present invention relates generally to medical equipment transfer systems. More specifically, the present invention relates to a transfer system for reliably, safely and securely transferring life support apparatus between various support platforms when transporting critically ill patients.

BACKGROUND

In the daily care of critically ill patients, a great diversity of medical equipment, including infusion management equipment and supplies, pressure transducers, physiological monitors and other equipment is employed. Such equipment typically is set up at the patient's bedside where it is supported by various stands, racks or hangers. For example, the equipment may be supported by 5-star floor stands, attached to headwalls, suspended from booms that are affixed to the ceiling, floor or wall mounted columns, or on other stationary or mobile platforms.

The difficulty arises when, at times, these patients must be transported from their rooms for administering of various hospital services such as surgery, imaging, radiology or special procedures. Similarly, these patients may need to be transported to other specialized facilities. Such transports are often necessary under emergency conditions while patients are distressed and frail, requiring that such transports be competed rapidly and with minimal disruption of therapy, life support and monitoring.

In the known methods for moving patients in tandem with their support equipment, the caregivers in addition to moving the patient bed must also wheel several intravenous-fluid (IV) stands next to or behind a bed, or pile the equipment onto the mattress next to the patient. These techniques typically prove hazardous because the IV stands may fall and tear out patient connections. Such patient transports are also inefficient and costly because much staff time is required to prepare a patient for transport and many caregivers are needed for moving the equipment in tandem with the bed along corridors, into elevators and through doors.

In an attempt to overcome these shortcomings, several approaches for safer, more efficient and faster transport of patients and life support equipment have been provided in the prior art for the consolidation of life support equipment in a single equipment support structure, wherein the equipment support structure is moved from a support within the room to a mobile support platform such as a patient bed. One known method involves vertically lifting an equipment support structure out of a docking cradle of a headwall or other structure by utilizing the elevating mechanism of the hospital bed and, after transport, depositing the equipment support structure in a stationary docking cradle, again relying on the height adjustment mechanism of the bed.

U.S. Pat. No. 4,945,592 (Sims) teaches use of the hospital bed as a lifting mechanism but fails to provide a safety system to lock the support structure to either the mobile or stationary platform. Further the support equipment cannot be placed on the bed in an optimal position for patient care during transport. Also, conditions on the ground are such that it is difficult to align mobile and stationary platforms for seamless transfers. A further problem in this system is that the system components are not standardized and are therefore costly, and components generally do not conform to effective infection control requirements.

Similarly, U.S. Pat. No. 7,065,812 (Newkirk) also fails to provide a safety system to prevent accidental dislodging of the equipment support structure from engagement to stationary or mobile platforms. Arms and docking mechanisms are not standardized and therefore are costly to manufacture, and the support equipment cannot be moved into an optimal location for effective patient care during transport, nor do components generally conform to effective infection control requirements.

US Published Application No. 2006/0242763 (Graham) fails to provide a safety system to prevent accidental dislodging of the equipment support structure from engagement to stationary or mobile platforms. Additionally, the docking elements are arranged vertically above each other in co-axial relationship, which restricts optimal positioning during transport, fails to provide effective articulation between equipment support structure and patient bed, and therefore does not allow optimal in-transport equipment positioning.

U.S. Pat. Nos. 5,527,125 and 5,306,109 (Kreuzer) provide a safety system to prevent accidental dislodging of the equipment support structure from engagement to stationary or mobile platforms but positions the engagement cones in side-by-side, coplanar relationship which does not permit placement of support equipment vis-a-vis the patient for optimal care during transport. The approach is complex and costly as there is no standardization of crucial docking components, and the safety system relies on a complex and costly sliding mechanism.

U.S. Pat. No. 7,661,641 (Wong) teaches a safety system to prevent accidental dislodging of the equipment support structure from engagement to stationary or mobile platforms but also arranges the docking elements vertically above each other in co-axial relationship which restricts optimal positioning during transport, fails to provide effective articulation between equipment support structure and patient bed and therefore does not allow optimal in-transport equipment positioning. The safety system and the requirement for a mobile base make this approach complex and costly to implement.

Other approaches as disclosed in U.S. Pat. Nos. 7,314,200 and 4,511,158 utilize transfer and docking by connecting to mobile and stationary platforms using a horizontal docking movement rather than a vertical one. These approaches are overly sensitive to misalignment in height and axial orientation of the components to be docked.

In view of the shortcomings of known medical equipment transfer systems, the present invention provides a novel transfer apparatus for transferring said life support equipment between different platforms such as a stationary wall or ceiling support structure and a mobile support platform such as a patient bed. There is therefore a need for a system for transferring patient support equipment from stationary to mobile platforms that is of low mechanical complexity, and that utilizes fewer, standardized, simpler components to permit low-cost manufacturing and reduced service and warranty costs by minimizing field maintenance and extending the mean time between failures. There is also a need for a patient transfer and transport system that assures the life support equipment is securely locked to either the stationary or mobile platform so that it cannot be accidentally removed or dislodged, yet allows seamless transfer of the life support equipment between stationary and mobile platforms that automatically engages the security lock during transfer by utilizing a vertical lift mechanism such as a typical, motorized patient bed. There is a further need for a patient transfer and transport system that minimizes in-service training of caregivers, by making transfer from stationary to mobile platforms intuitive, minimizing training of transport staff by eliminating or automating critical steps in the procedure, and relying less on memory or alertness of personnel. There is still a further need for a patient transfer and transport system that minimizes crevices, exposed fasteners and upward-facing cavities to facilitate effective cleaning and infection control. There is yet a further need for a patient transfer and transport system that is relatively insensitive to the misalignment of equipment typically encountered in hospitals during transfers between stationary and mobile platforms. There is also a need for a patient transfer and transport system that permits nursing staff to position and re-position the support equipment relative to the patient that allows ready access to the patient and facilitates easy monitoring and control of life-support equipment during transport, minimizes the total footprint of the bed and associated equipment, and minimizes the risk of dislodging fluid lines, cables and leads between equipment and patient during transfer between stationary and mobile platforms. Finally, there is a need for a patient transfer and transport system that is articulated to allow caregivers full freedom in repositioning the patient support equipment around the patient's head and allows the articulations to be locked in place during transport.

SUMMARY

In this regard, the present invention provides an equipment transfer device that is transferable from one support to another support. The transport device is comprised of a clamshell housing having two substantially identical but mirrored outer shells that are held together by screws. Each housing half further comprises two similar, half-conical recesses, preferably disposed on generally parallel, spaced-apart vertical axes such that, when assembled to form said clam-shell, the two housing halves form circular docking cups that are open to the bottom.

The docking cups are spaced apart horizontally along the central plane of the clamshell housing such that each docking cup can receive a docking cone from below, as further described below. Each docking cone is supported on a structure and is capable of moving in a generally vertical direction into engagement or out of engagement along the axis of their respective docking cups while maintaining horizontal separation to avoid interference and collision with one another. The docking cups may be positioned symmetrically on a horizontal plane, but in alternate embodiments the docking cups are preferably disposed on different horizontal levels, with a vertical separation between the upper and lower docking cups.

Additionally, a support post is rigidly trapped and fastened between the two housing halves, preferably in coaxial relationship with the upper docking cup. The support post protrudes from the upper end of the transfer device as a base to which an equipment support structure is rotatably attached. Support structures of various configurations may be interchangeably attached according to specific caregiver requirements.

In accordance with another aspect of the preferred embodiment of the present invention, there is provided a security mechanism that secures a first docking cone, upon engagement to the transfer device, to a first docking cup. The security mechanism only releases the first docking cone from the first docking cup upon insertion and full engagement of a second docking cone in the second docking cup. The security mechanism of this invention prevents accidental disengagement of the transfer device from either the stationary or mobile platforms to which it is docked as it securely locks an engaged docking cone to its respective docking cup. The transfer device may only be disengaged from a first docking cone when another docking cone is fully inserted and engaged in the other docking cup, or vice-versa. The security mechanism operates autonomously without human intervention. It is activated by user control of the vertical movement of the docking activation mechanism, such as the height adjustment of a hospital bed.

It is therefore an object of the present invention to provide a system for transferring patient support equipment from stationary to mobile platforms that is of low mechanical complexity, and that utilizes fewer, standardized, simpler components to permit low-cost manufacturing and reduced service and warranty costs by minimizing field maintenance and extending the mean time between failures. It is a further object of the present invention to provide a patient transfer and transport system that assures the life support equipment is securely locked to either the stationary or mobile platform so that it cannot be accidentally removed or dislodged, yet allows seamless transfer of the life support equipment between stationary and mobile platforms that automatically engages the security lock during transfer by utilizing a vertical lift mechanism such as a typical, motorized patient bed. It is still a further object of the present invention to provide a patient transfer and transport system that minimizes in-service training of caregivers, by making transfer from stationary to mobile platforms intuitive, minimizing training of transport staff by eliminating or automating critical steps in the procedure, and relying less on memory or alertness of personnel. It is yet a further object of the present invention to provide a patient transfer and transport system that minimizes crevices, exposed fasteners and upward-facing cavities to facilitate effective cleaning and infection control. It is a further object of the present invention to provide a patient transfer and transport system that is relatively insensitive to the misalignment of equipment typically encountered in hospitals during transfers between stationary and mobile platforms. It is still a further object of the present invention to provide a patient transfer and transport system that permits nursing staff to position and re-position the support equipment relative to the patient that allows ready access to the patient and facilitates easy monitoring and control of life-support equipment during transport, minimizes the total footprint of the bed and associated equipment, and minimizes the risk of dislodging fluid lines, cables and leads between equipment and patient during transfer between stationary and mobile platforms. Finally, it is an object of the present invention to provide a patient transfer and transport system that is articulated to allow caregivers full freedom in repositioning the patient support equipment around the patient's head and allows the articulations to be locked in place during transport.

Also disclosed is a transfer system for a patient care apparatus, the transfer system including: a transfer device including a first docking cup and a second docking cup, each of the first docking cup and the second docking cup sized to accept a receiver; and a security mechanism enclosed within the transfer device and including a first security lever and a second security lever, the first security lever positioned to disengage a first receiver in the first docking cup when a second receiver is received within the second docking cup, and the second security lever positioned to disengage the second receiver in the second docking cup when the first receiver is received within the first docking cup.

Also disclosed is a transfer device for a patient care apparatus including: a first docking cup and a second docking cup, each of the first docking cup and the second docking cup sized to receive a receiver; a security mechanism enclosed within the transfer device; and an offset arm mounted on the housing.

Also disclosed is a method of using a transfer system, the transfer system including a transfer device, the transfer device including a support shaft and a shaft brake engageable with the support shaft, the method including: disengaging the shaft brake by hand; rotating the support shaft; and re-engaging the shaft brake by hand.

These together with other objects of the invention, along with various features of novelty that characterize the invention, are pointed out with particularity in the further description annexed hereto and forming a part of this disclosure. For a better understanding of the invention, its operating advantages and the specific objects attained by its uses, reference should be had to the accompanying drawings and descriptive matter in which there is illustrated a preferred embodiment of the invention.

Various implementations described in the present disclosure may include additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

BRIEF DESCRIPTION OF THE DRAWINGS

The features and components of the following figures are illustrated to emphasize the general principles of the present disclosure. Corresponding features and components throughout the figures may be designated by matching reference characters for the sake of consistency and clarity. In the drawings which illustrate the best mode presently contemplated for carrying out the present invention:

FIG. 47 is a perspective view of a mobile support platform of the transfer system of FIG. 46;

FIG. 48 is an exploded view of the mobile support platform of FIG. 47;

FIG. 54b is a side view of a security lever of the transfer device shown in FIG. 49;

FIG. 54c is a bottom view of a security lever of the transfer device shown in FIG. 49;

FIG. 54d is a side view of another embodiment of the security lever of the transfer device shown in FIG. 49;

FIG. 62a is a detail exploded perspective view of a shaft brake mechanism of the transfer device of FIG. 52 together with a shaft of the transfer device;

FIG. 62b is a detail perspective view of a lower end of a support shaft of the transfer device of FIG. 52;

FIG. 63 is a side view of a standoff fastener of the shaft brake mechanism of FIG. 62;

FIG. 64b is a top perspective view of the shaft brake mechanism of FIG. 64a;

FIG. 64c is a side view of a standoff fastener of the shaft brake mechanism of FIG. 64a;

DETAILED DESCRIPTION

Figure 1:
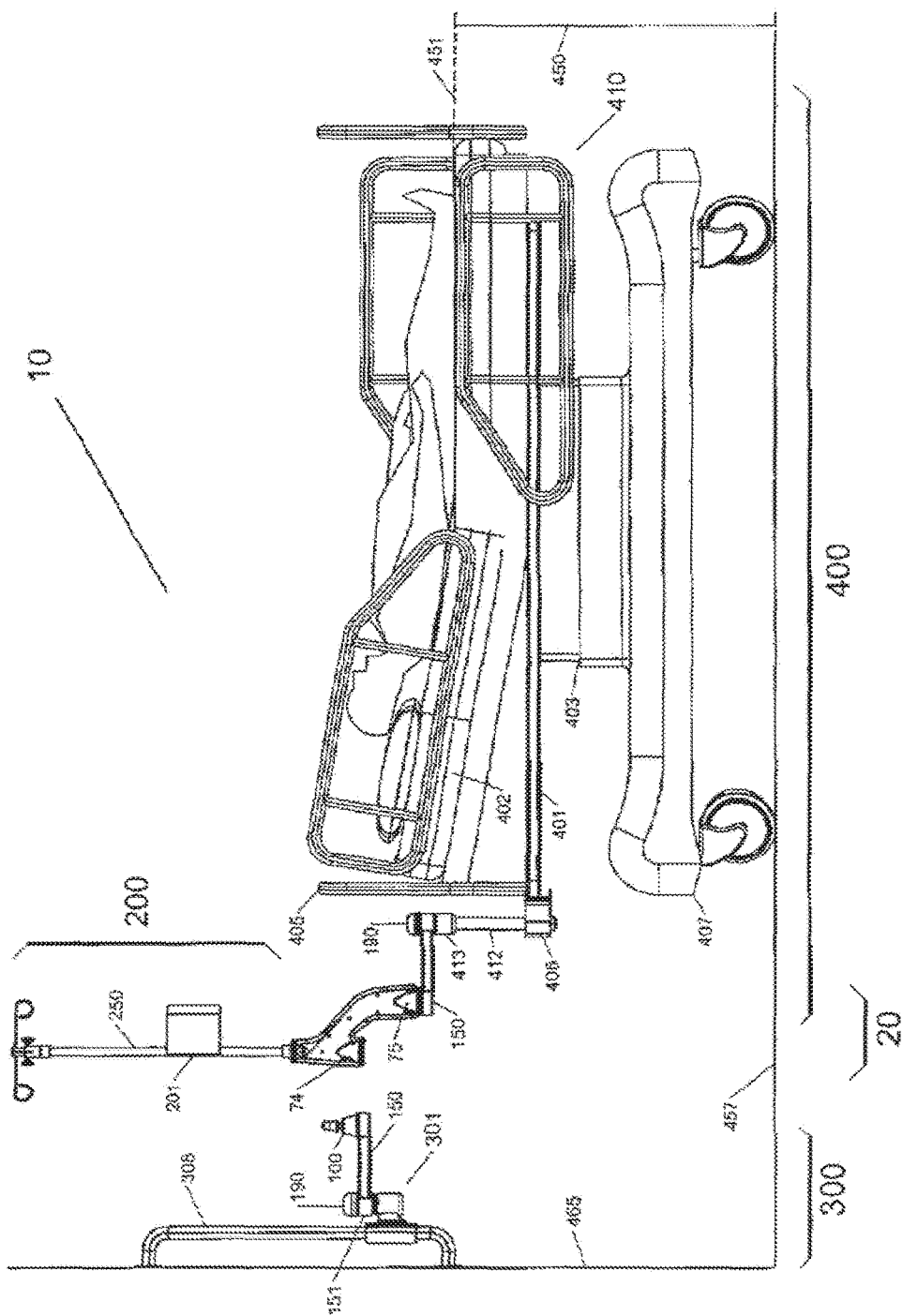
FIG. 1 is a side view of the transfer system of the present invention docked to a mobile support platform in preparation for transfer.

Disclosed is a transfer system and associated methods, systems, devices, and various apparatuses. The transfer system includes a transfer device, one or more receivers, and arms in various embodiments. It would be understood by one of skill in the art that the disclosed transfer system and transfer device are described in but a few exemplary embodiments among many. No particular terminology or description should be considered limiting on the disclosure or the scope of any claims issuing therefrom.

Now referring to the drawings, the equipment transfer system is shown and generally illustrated in the figures. As can be seen the principal component of the transfer system is a transfer device 20 that can be selectively supported and moved between a stationary support platform 300 and a mobile support platform 400 to facilitate the transfer of patient care apparatus 200 supported thereon.

Turning to FIG. 1, the transfer system 10 includes a stationary support platform 300, a mobile support platform 400 and a transfer device 20 that supports a patient care apparatus 200 and is capable of transferring the patient care apparatus 200 between a stationary support platform 300 and a mobile support platform 400 and vice-a-versa. Within the scope of the present invention the term "transfer" refers to transferring patient support equipment between stationary support platforms including walls, headwalls, ceiling-mounted or wall-mounted booms from various manufacturers, free-standing and/or movable columns and other structures typically found in hospital rooms and treatment facilities to which a stationary cone arm connector 301 may be attached, and mobile support platforms such as patient beds, gurneys, wheelchairs, ambulances, helicopters or other mobile platforms, and vice-versa. As anyone familiar with the art will appreciate, substituting alternative rotatable attachment means, alternative stationary support platforms, alternatives to post 308 and/or stationary cone arm connectors 301, as well as transfers between stationary platforms or between mobile platforms, are within the scope of this invention.

Figure 3:
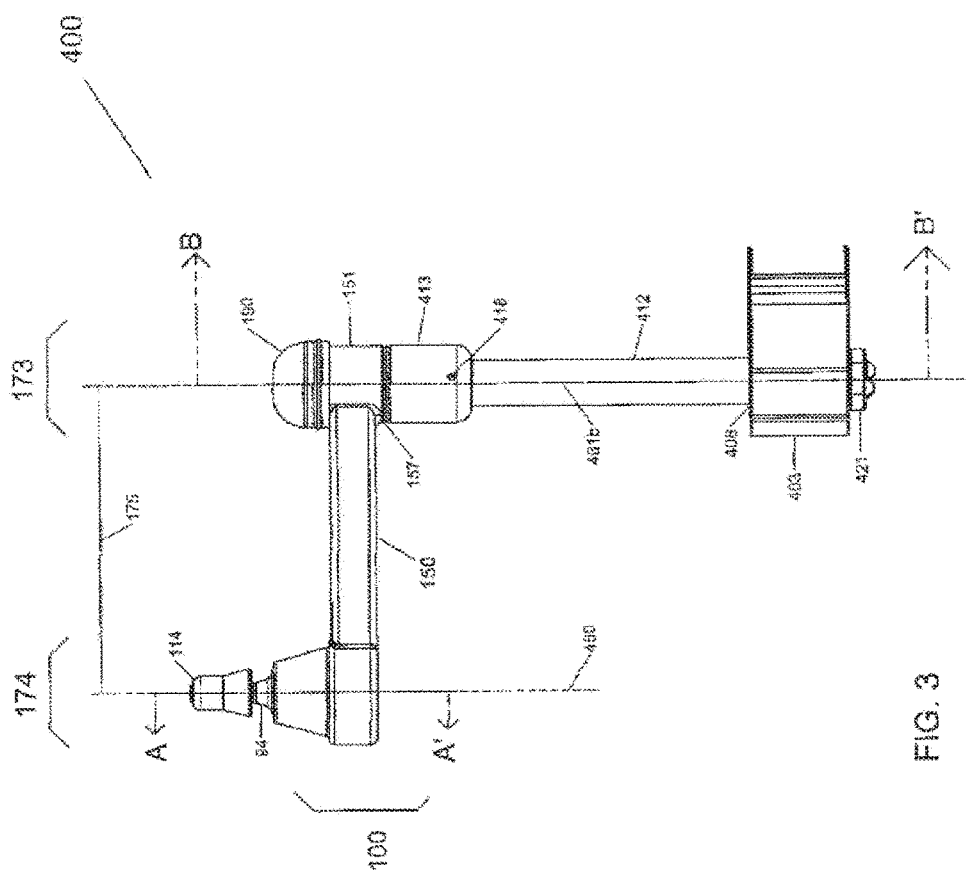
FIG. 3 is a side view of a mobile support platform showing an attachment bracket.
Figure 2:
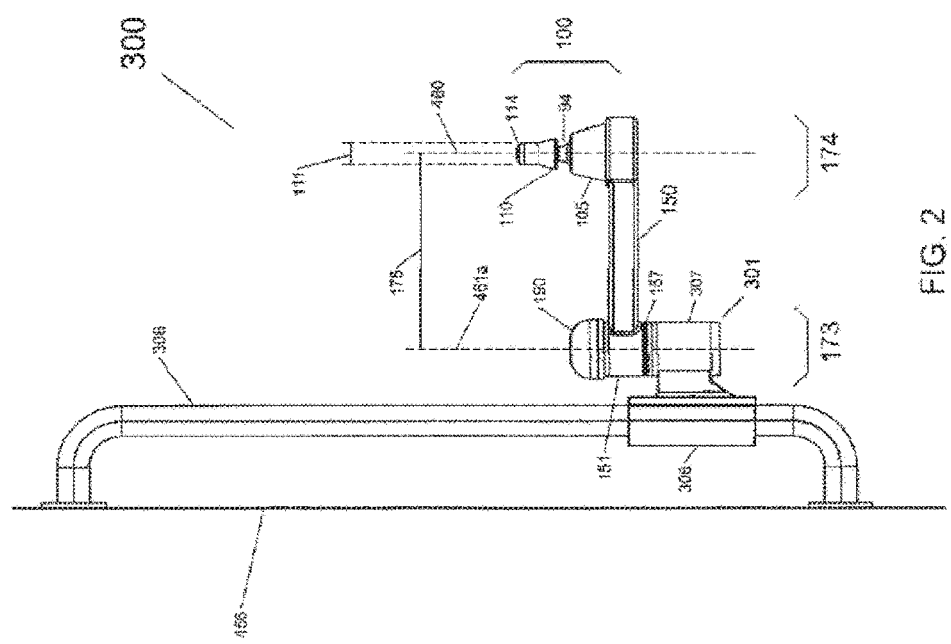
FIG. 2 is a side view of a stationary support platform attached to a wall.

Referring to stationary support platform 300 and mobile support platform 400 of the preferred embodiment, as shown in FIGS. 1-3, platforms 300 and 400 may both support a cone arm 150. Cone arm 150 has a distal end 174 and a proximal end 173. The distal end 174 comprises docking cone 100 for docking with transfer device 20 and the proximal end 173 comprises arm joint 151 which may be attached to stationary or mobile support platforms 300 or 400, respectively. Cone arm 150 may be attached to a stationary support platform, such as post 308, or directly to a wall 465 using stationary cone arm connector 301. Cone arm 150 may also be attached to a mobile support platform 400, such as a hospital bed, as more fully described below, using mobile cone arm adapter 413 which is mated to accessory bracket 406 of a hospital bed 410 by means of bed post 412 or other known connection.

Figure 4:
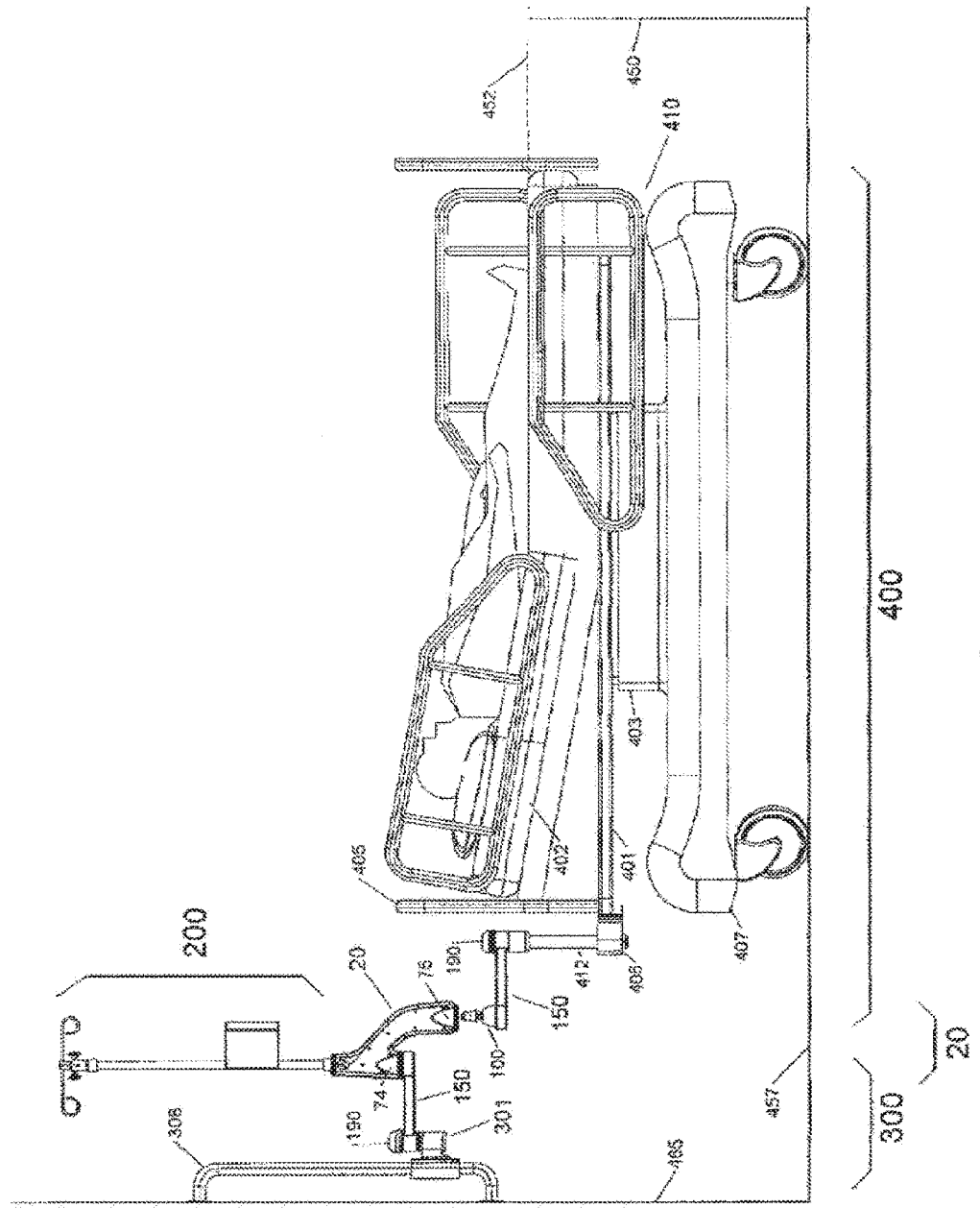
FIG. 4 is a side view the transfer system docked to a stationary support platform with the mobile support platform lowered for docking to the transfer device in preparation for transfer.
Figure 9:
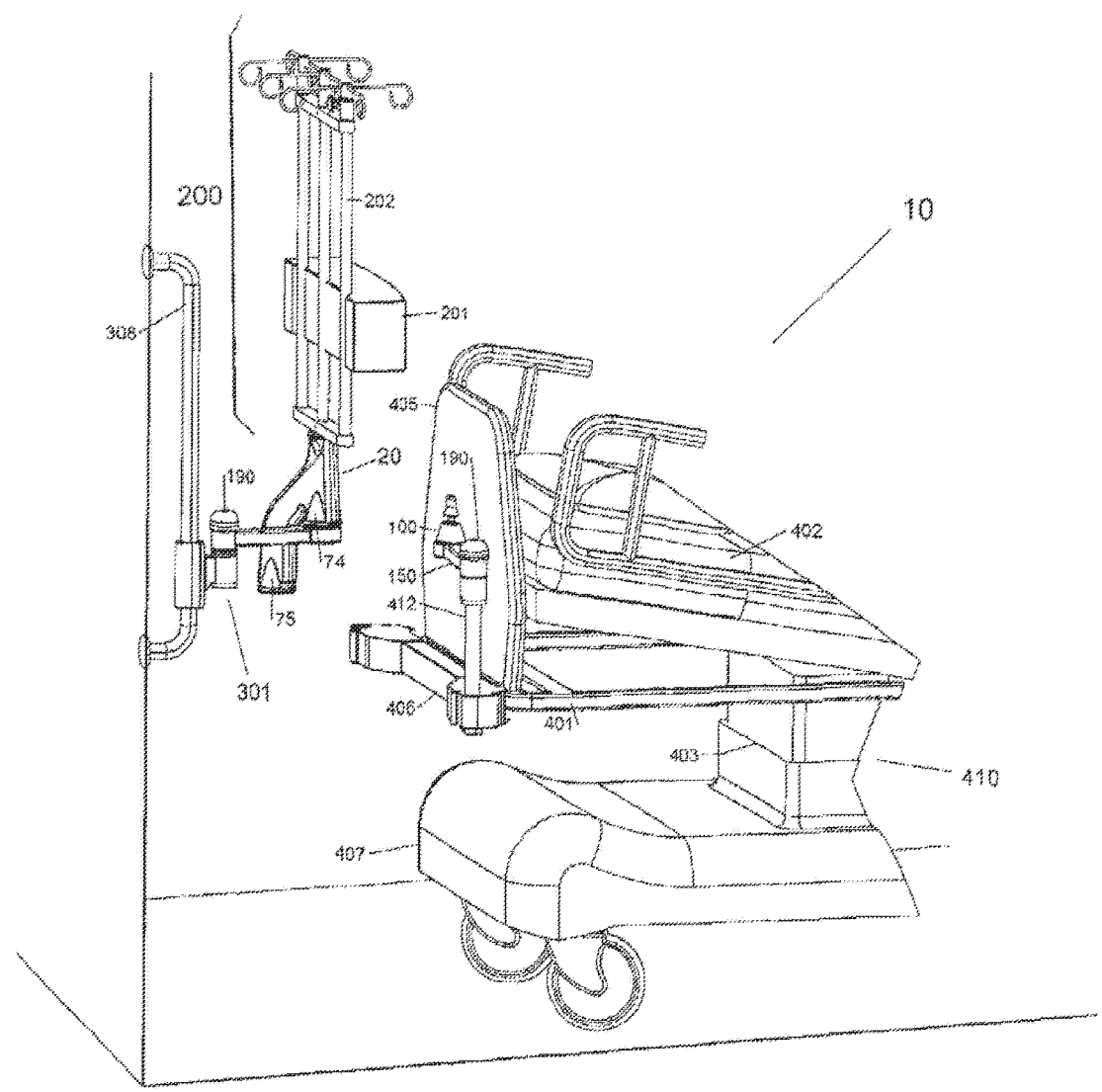
FIG. 9 is a perspective view of the transfer system with a transfer device docked to a stationary support platform and with the docking arm of the mobile support platform and the transfer device on the stationary support platform stowed after transport, and the mobile support platform partially cut away.

As shown in FIGS. 4 & 9, when treated in a hospital room, a patient typically may be attached to patient care apparatus 201 connected to an equipment support structure 200. The equipment support structure preferably is attached to transfer device 20 and rotatably docked to docking cone 100 of a cone arm 150 that is rotatably joined to a stationary cone arm connector 301. Cone arm 150, docking cone 100 and cone arm connector 301 provide articulation so that stationary support platform 300 may be positioned for optimal patient care. Having patient care apparatus 201 physically detached from hospital bed 410, while a patient is in a room, is preferred in many health care facilities in order to provide unobstructed patient access all around hospital bed 410. As used herein, the term "docking" and "docking maneuver" refers to inserting a docking cone into a docking cup generally in coaxial alignment and in a load-bearing relationship where cone arm 150 supports transfer device 20 and patient care apparatus 201.

Figure 16:
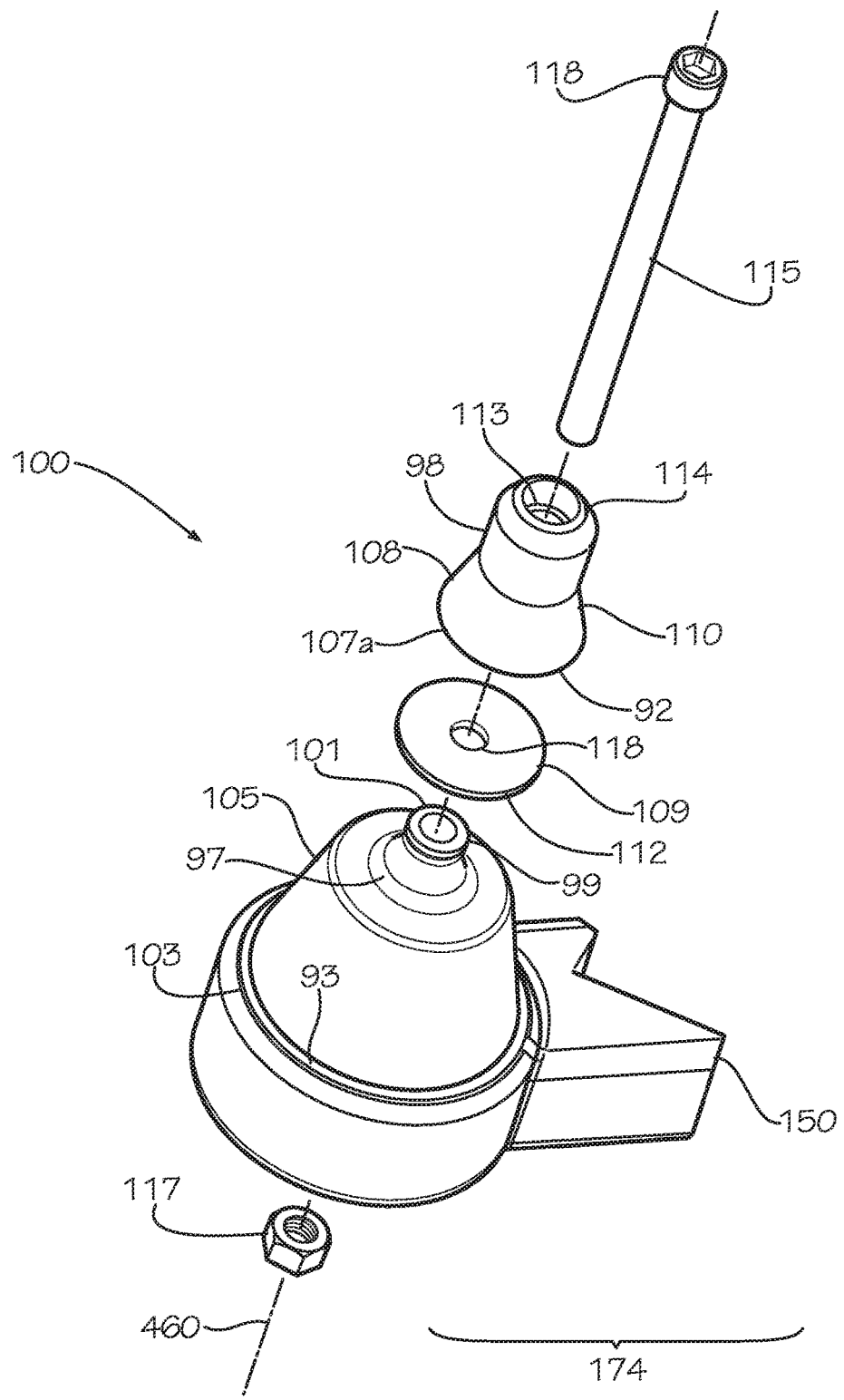
FIG. 16 is an exploded view of a docking cone.

As shown in FIGS. 2 and 3, the cone arms 150 that are attached to both the stationary support platform 300 and the mobile support platform 400 are substantially identical. In the preferred embodiment, arm length 175 is approximately 9.5 inches. However, arm length 175 may reasonably range between 4 inches and 15 inches, although shorter and longer arm lengths 175 may be used to meet specific requirements, and cone arms 150 of different lengths may be employed in a single transfer system 10. In addition, in the preferred embodiment shown in FIGS. 14 & 16, arm joint 151 and docking cone 40, as well as the components required in the arm joint 151 for achieving joint stability and user adjustment, have both been standardized in order to minimize manufacturing cost and parts inventory. As anyone familiar with the art may recognize, one or more additional articulating arm segments may be installed between arm joint 151 and stationary arm connector 301, and/or between mobile cone arm adapter and arm joint 151, in order to extend the reach and flexibility of system 10.

Figure 12:
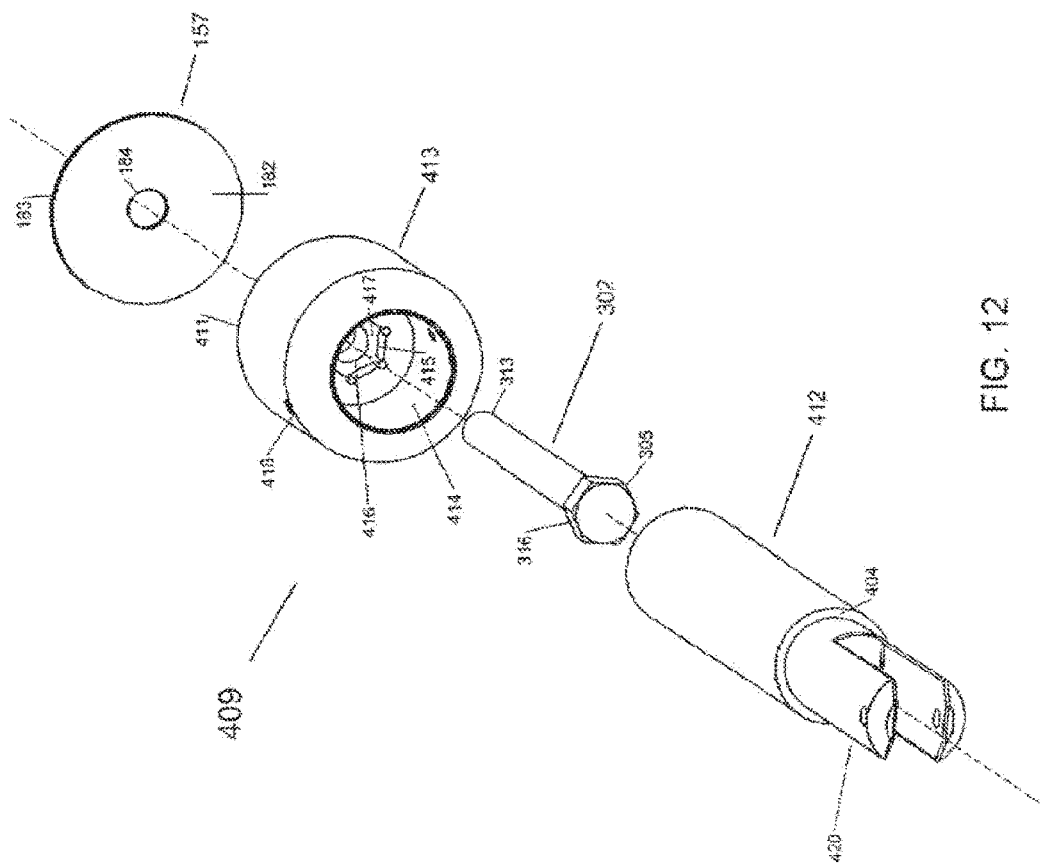
FIG. 12 is an exploded view of a bed connection.
Figure 13:
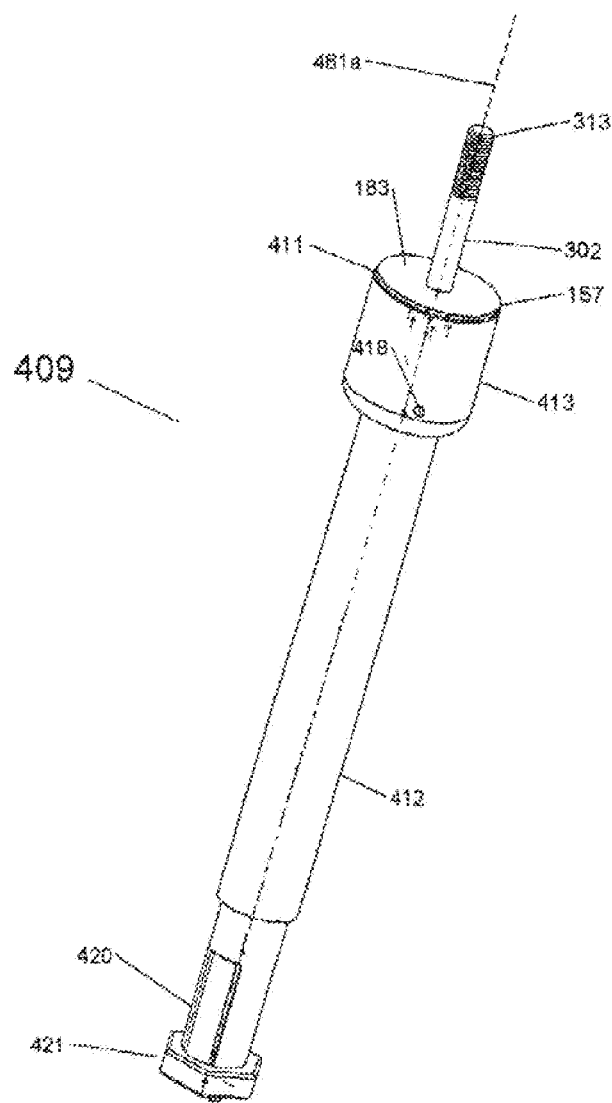
FIG. 13 is a perspective view of a bed connection.
Figure 14:
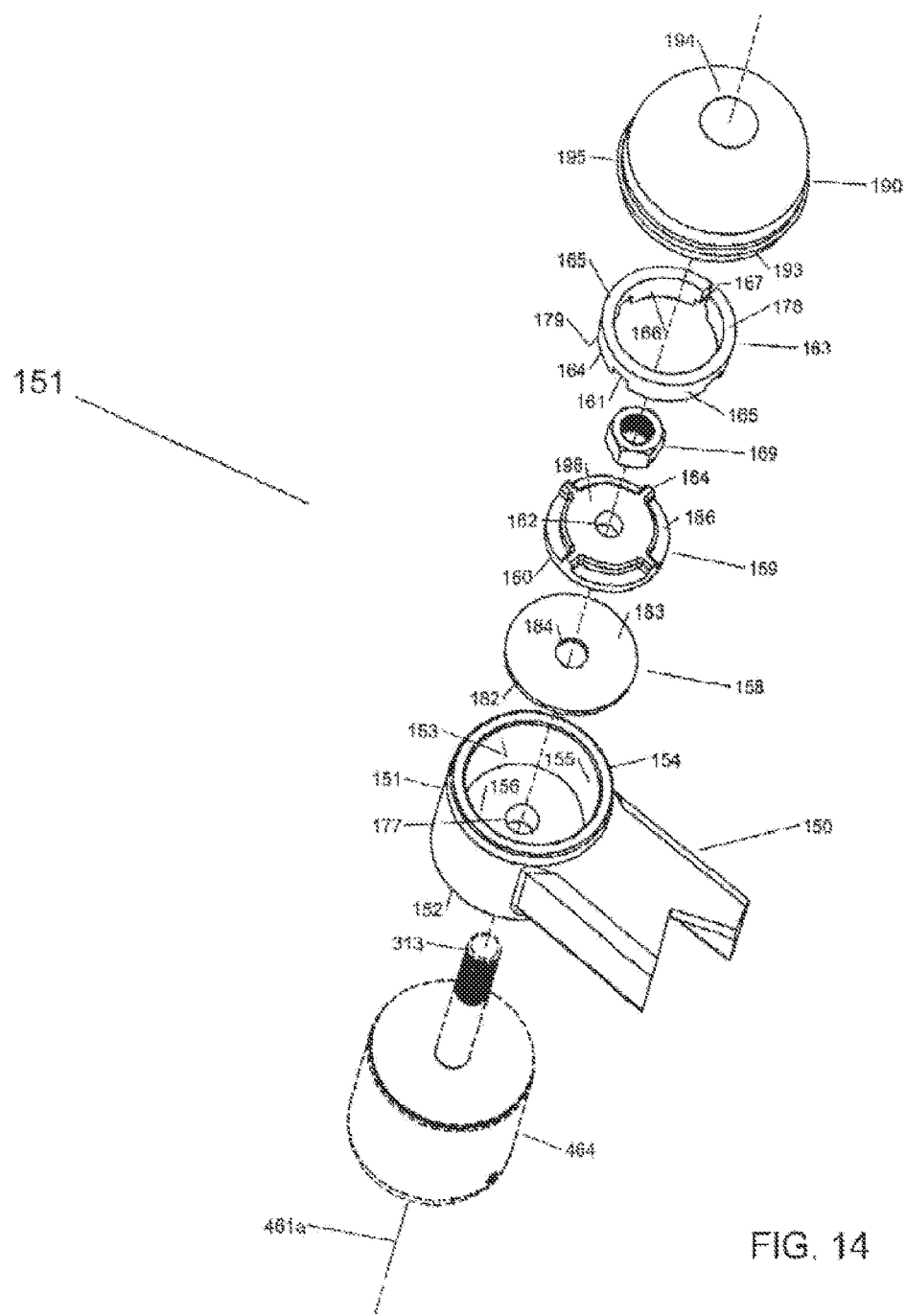
FIG. 14 is an exploded view of an arm joint showing attachment to either a stationary cone arm connection or a bed connection represented by a dotted outline.
Figure 15:
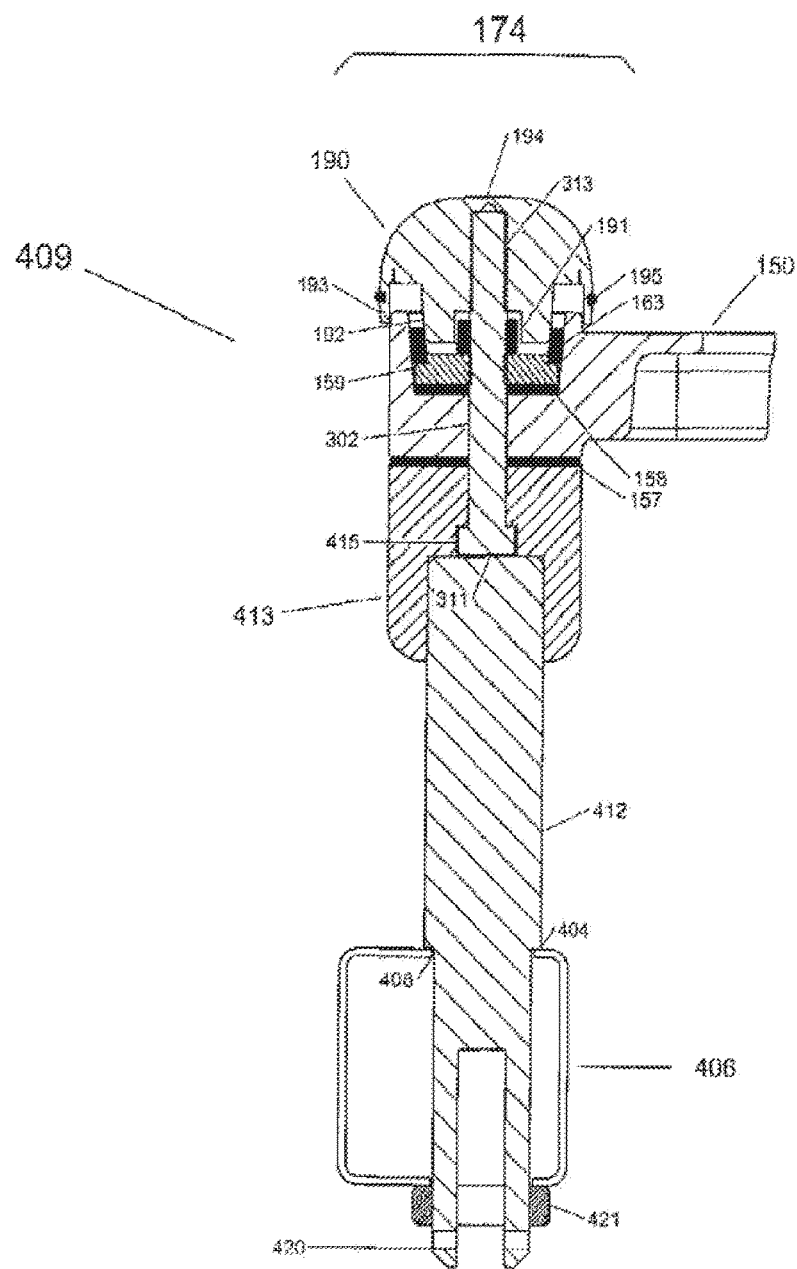
FIG. 15 is a sectional side view of a bed connection taken along line B-B' of FIG. 3.

As shown in FIGS. 10-13, stationary arm connector 307 and mobile cone arm adapter 413 have a stationary contact interface 312 and a mobile contact interface 411, respectively. Both contact interfaces 312, 411 are substantially identical and enable essentially identical attachment to arm joint 151 located at the proximal end 173 of cone arm 150, regardless whether attached to mobile or stationary platforms. As shown in FIGS. 14 & 15, standardization of attachment and joint tensioning components of cone arms 150 is instrumental in reducing the complexity and manufacturing cost of transfer system 10. Stationary contact interface 313 is a flat surface 312 and is perpendicular to the longitudinal axis of bolt 302. Bolt 302 protrudes from stationary contact interface 312 and is held in place and secured against rotation by capturing hexagonal bolt head 305 with bolt head restraints 310. Analogously, the mobile contact interface is perpendicular to longitudinal axis of bolt 302. Bolt 302 protrudes from mobile contact interface 411 and is held in place and secured against rotation by capturing hexagonal bolt head 305 with bolt head restraints 310.

Figure 10:
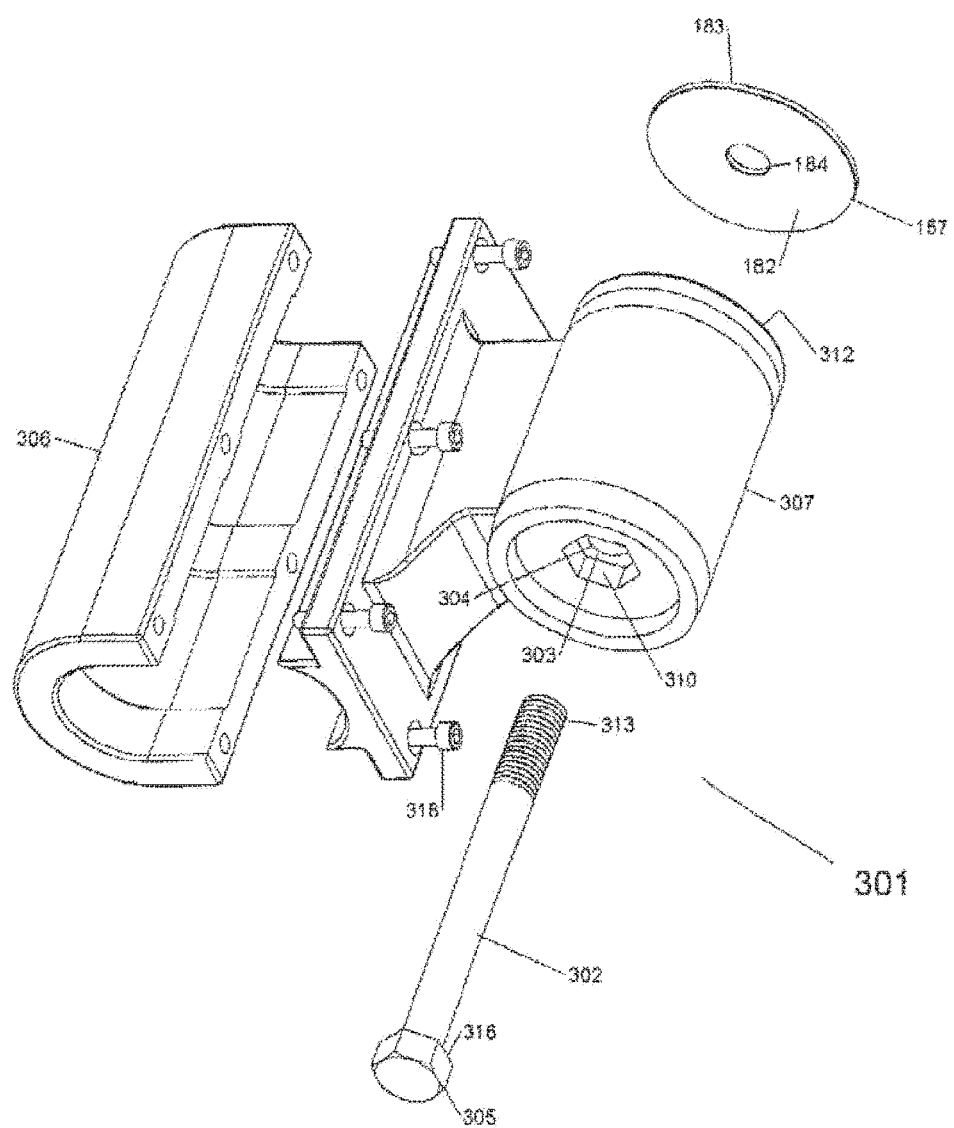
FIG. 10 is an exploded view of a stationary cone arm connector.

As shown in FIGS. 2, 9 & 10, stationary cone arm connector 301 is comprised of arm connector 307 and clamp 306. Arm connector 307 and clamp 306 cooperate, in a clamping and load-bearing relationship, to firmly attach stationary cone arm connector 301 to post 308 by means of attachment screws 318.

In order to achieve low manufacturing cost, the number of parts and components required in transfer system 10 is minimized by standardization. Cone arm 150 used with a stationary support platform 300 is preferably substantially identical to cone arm 150 used with a mobile support platform 400, and the components required and method used for attaching cone arm 150 to arm connector 307 of stationary support platform 300, as shown in FIG. 2, is preferably substantially identical to the components required and method used for attaching cone arm 150 to mobile cone arm adapter 413 of mobile support platform 400, as shown in FIG. 3.

Figure 11:
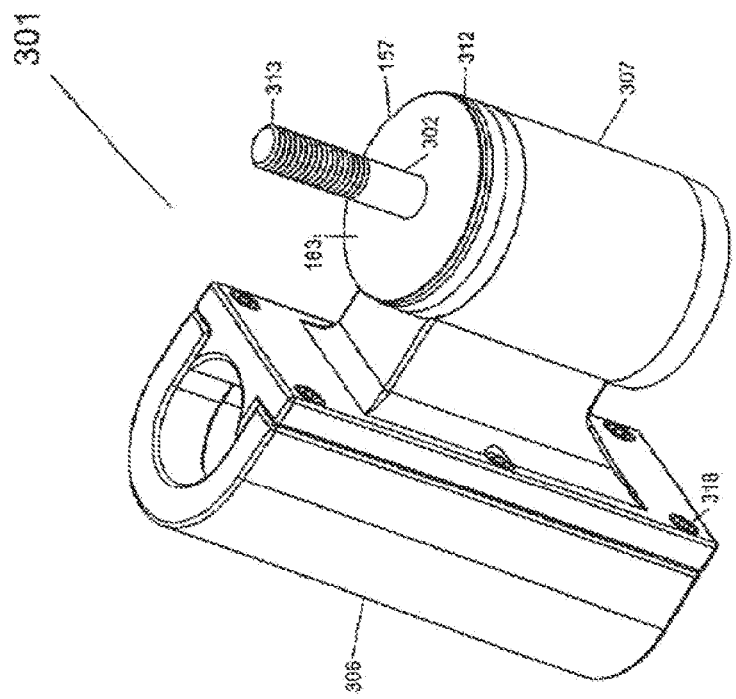
FIG. 11 is a perspective view of a stationary cone arm connector.

As shown in FIGS. 2, 11 & 12, arm joint 151 may be attached to stationary arm connector 307 to form a rotatable joint that permits cone arm 150 to rotate on arm connector axis 461*a* in a horizontal plane. The treaded bolt end 313 of bolt 302 is pushed up through bolt hole 315 with the bolt head base 316 of hexagonal head 305 in contact with bolt head bearing surface 303 and hexagonal head 305 in engagement with bolt restraints 310 to prevent rotation of bolt 302. Threaded bolt end 313 may issue from the center of, and perpendicularly to, stationary contact interface 312. Thrust bearing 157 may be placed on stationary contact interface 312 in coaxial relationship with bolt 302 and with lower bearing face 182 in coplanar and sliding relationship with stationary contact interface 312 to constitute a standardized attachment for cone arms 150 to stationary support platforms 300.

As shown in FIGS. 11-15, the connections between cone arm 150 and arm connector 307, and cone arm 150 and mobile cone arm connector 413, are substantially identical. Cone arm 150 may be placed onto bolt 302 with bolt bore 177 in coaxial relationship, and with the upper bearing face 183 of thrust bearing 157 in coplanar and sliding relationship with bearing surface 152 of arm joint 151, and with threaded bolt end 313 extending coaxially up through recess 153 of arm joint 151. Lock thrust bearing 158 may be placed over threaded bolt end 313 with the lower bearing face 182 of lock thrust bearing 158 in coplanar and sliding relationship with inner joint pressure surface 156. Pressure plate 159 may be threaded onto the treaded bolt end 313 by means of tapped center hole 162, with pressure surface 160 in coplanar relationship with, and tightened against, the upper bearing face 183 of lock thrust bearing 158 in order to cause tension on bolt 302 and take up slack in arm joint 151. Jam nut 169 is threaded onto threaded bolt end 313 and tightened against pressure plate 159 in jam-nut relationship to secure pressure plate 159 against rotation relative to bolt 302 during continued use of transfer system 10.

As shown in FIGS. 14 & 15, adjustment knob 190 is in threaded engagement with threaded bolt end 313 of bolt 302 that protrudes through jam nut 169. Clockwise or counter-clockwise rotation, respectively, of adjustment knob 190, permits users to adjust the friction between cone arms 150 and stationary and mobile support platforms 300 and 400, respectively, without affecting the load bearing ability or stability of arm joint 151. Adjustment knob 190 has a threaded center boss 191 with tapered outer surface 192, crown 194 and side skirt 193. Side skirt 193 is sized to protrude over, and overlap with, recess rim 154 of cone arm 150 when adjustment knob 190 is fully tightened to facilitate infection control. To offer better hand purchase when users tighten and loosen adjustment knob 190, crown 194 and side skirt 193 may be grooved to retain an external O-ring 195 or may be indented, serrated or otherwise shaped (not shown). Tapered outer surface 192 of threaded center boss 191 cooperates with friction wedge 163 to control joint friction.

Friction wedge 163 is an annulus with essentially parallel upper and lower surfaces 178, 179, respectively, outer wedge taper 165, inner wedge taper 166, and axial expansion cut 167 that permits friction wedge 163 to expand in response to tightening of adjustment knob 190. Lower wedge surface 179 is in contact with base surfaces 186 of registration recesses 161. Registration recesses 161 are sized to interdigitate with matching registration protrusions 164 on pressure plate 159 to limit rotation of friction wedge 163 relative to pressure plate 159 in order to prevent the known problem of tightening or loosening an arm joint, respectively, when a cone arm is moved clockwise or counter-clock wise.

Tightening adjustment knob 190 on bolt 302 pushes friction wedge 163 against pressure plate 159 and forces tapered outer surface 192 of threaded center boss 191 of adjustment knob 190 against inner wedge taper 166 of friction wedge 163 causing friction wedge 163 to expand. Outer wedge taper 165 of friction wedge 163 is forced against inner wall 155 of recess 153 of arm joint 151 to progressively increase or decrease joint friction when a user tightens or loosens adjustment knob 190.

Analogously, cone arm 150 may be attached to mobile support platform 300 by means of mobile cone arm adapter 413 fastened to vertical bed post 412. There are many known mobile support platforms 400, including hospital beds, stretchers and gurneys from various manufacturers, special procedure support devices, wheelchairs, and other structures typically found in hospitals and treatment facilities to which a mobile cone arm adapter 413 may be adapted for attachment to alternative stationary and mobile support platforms 300, 400 to enable system 10 to be used with known variations in known attachment methods. Such adaptations, as anyone familiar with the art may recognize, are within the scope of this invention. Analogously, as shown in FIGS. 3, 13 & 14, arm joint 151 may also be attached to mobile cone arm adapter 413 to form a rotatable joint that permits cone arm 150 to rotate on bed post axis 461b in a horizontal plane. Treaded bolt end 313 of bolt 302 is pushed up through bolt hole 315 with the bolt head base 316 of hexagonal head 305 in contact with bolt head bearing surface 303 and hexagonal sides of bolt head 305 in engagement with bolt restraints 310 to prevent rotation of bolt 302. Threaded bolt end 313 may issue from in the center of, and perpendicularly to, mobile contact interface 411. A thrust bearing 157 may be placed on mobile contact interface 411 in coaxial relationship with bolt 302 and with lower bearing face 182 of thrust bearing 157 in coplanar and sliding relationship with mobile contact interface 411 to constitute a standardized attachment for cone arms 150 to mobile support platforms 400.

As shown in FIGS. 1 & 2-9, transfer device 20 is selectively attachable to the docking cones 100 of cone arms 150 in order to transfer patient care apparatus 201 between stationary support platforms 300 and mobile support platforms 400. The transfer device 20 supports equipment support structure 200 by means of support post 41 that is rigidly attached to, and protrudes out of, upper end 33 of clamshell housing 21 and rotatably engages equipment support structure 200. Hospital staff may attach patient care apparatus 201 to equipment support structure 200, such as infusion management devices and supplies, monitoring equipment, and other life support apparatus that may be required for the care of critically ill patients. The vertical axis of rotation (not shown) of equipment support structure 250 preferably is coaxial with upper docking cone axis 462.

The configuration of equipment support structure 200 may vary depending on type and number of patient care apparatus being used, hospital protocols, type of therapy or life support requirements. However, various configurations of equipment support structures 200 preferably share the capability of being interchangeably attached to support post 41. Generally, transfer device 20 and equipment support structure 200 are rotatably joined and paired for the duration of a patient's hospital stay or longer.

Mobile support platform 400 of the preferred embodiment preferably is a hospital bed 410. In hospital beds, mattress height 450 typically is adjustable between working height 451, low docking level 152 and high docking level 453 by lift mechanism 403 that may be powered by an electric motor, hand crank or other mechanism. FIG. 1 shows mattress 402 of hospital bed 410 at working height 451—a height typically chosen by hospital staff to perform their care giving tasks. Height-adjustable frame 401 may comprise an accessory bracket 406 near headboard 405 of hospital bed 410. Accessory brackets 406 on conventional hospital beds 410 provide for attachment of accessories such as push handles, foldable IV poles, guide wheels or orthopedic frames, and therefore offer a suitable attachment structure for transfer device 20. As shown in FIGS. 1 & 15, cone arm 150 may be attached to accessory bracket 406 of hospital bed 410 by means of the threaded lower end 420 of bed post 412 that may be inserted vertically, in fixed, load-bearing and non-rotating relationship, into one of the accessory connection openings such as accessory sockets 408 available in typical accessory brackets 406, or it may be otherwise attached to the structure of a hospital bed by welds, mechanical fasteners, clamps or other known fastening methods.

The method of preparing a patient for transport, safely transferring patient care apparatus 201 from attachment in the room to attachment to bed 410, safely transporting a patient to another location, and safely and expeditiously returning the patient to a room, as shown in FIGS. 1-5, 11 & 14, is described below. As used in this disclosure, the term "transport" refers to moving a patient in tandem with life support equipment attached to a mobile platform such as a patient bed, gurney, wheelchair, ambulance, helicopter or other mobile platform between locations within or between medical facilities, such as intensive care rooms, operating rooms, radiology and other imaging facilities, catheterization labs, or between buildings and hospitals.

Figure 5:
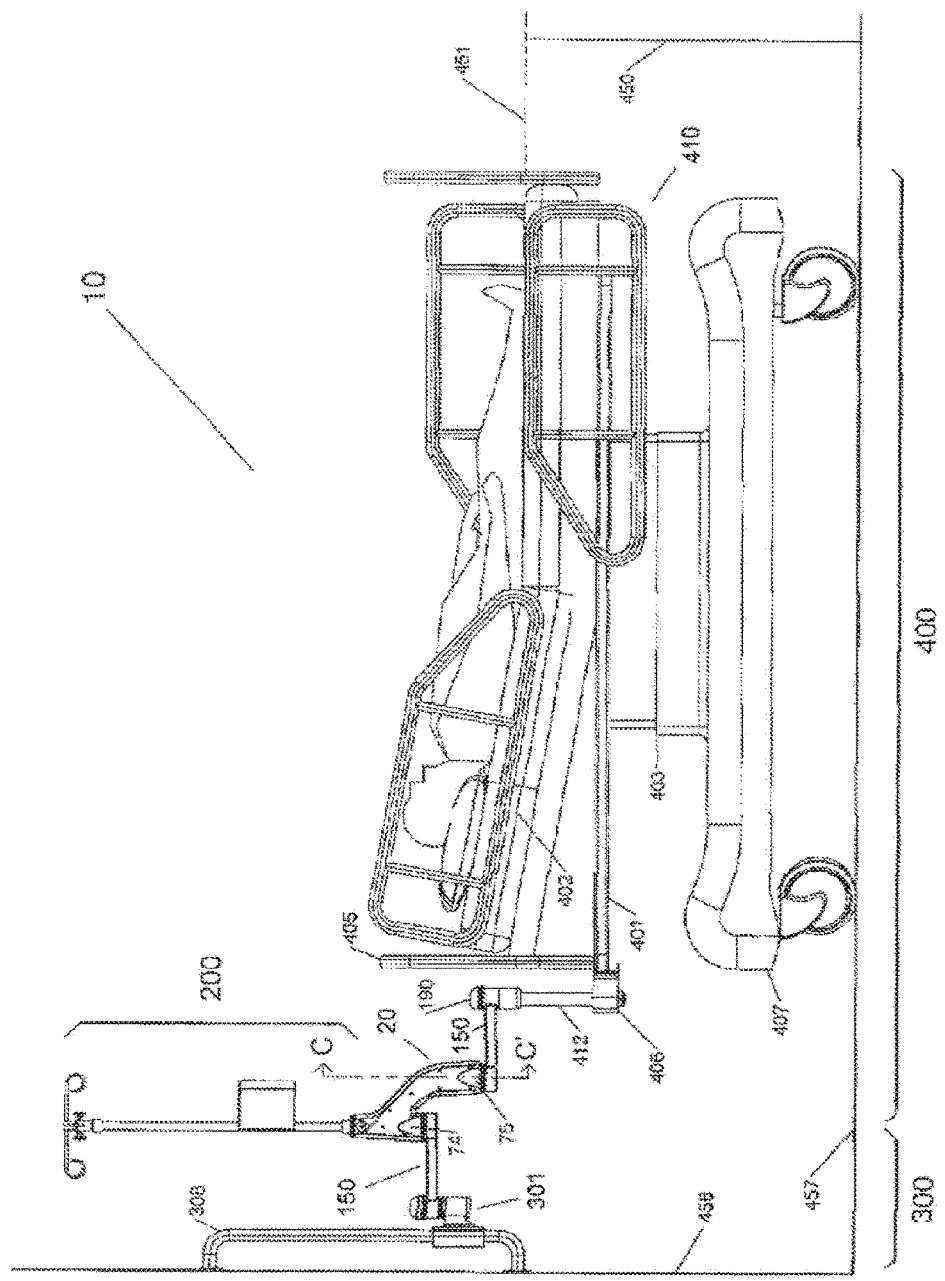
FIG. 5 is a side view of the transfer system docked to both a mobile support platform and the mobile support platform to simultaneously dock the transfer device during transfer.

Before transporting a patient from a room to another location, as shown in FIG. 4, upper docking cup 74 of transfer device 20 typically will be docked with, and secured to, a stationary support structure 300. In preparation of patient transport, transfer device 20 may be repositioned so that the lower docking cup faces hospital bed 410, and hospital bed 410 preferably may be moved closer to the stationary support platform 300. Activation of lift mechanism 403 may lower mattress height 450 from working height 451 to low docking level 452 to permit docking cone 100 of mobile support platform 400 to be maneuvered directly underneath, and into generally coaxial alignment with, lower docking cup 75 of transfer device 20. Activation of lift mechanism 403 of hospital bed 410 may raise mattress 402 and also raise docking cone 100 of mobile support platform 400, causing it to dock with transfer device 20. As shown in FIG. 5, docking cone 100 attached to stationary support platform 300 and docking cone 100 attached to mobile support platform 400 are simultaneously engaged in their respective docking cups 74, 75. Under continued activation of lift mechanism 403, security mechanism 120 automatically releases transfer device 20 from the stationary docking cone 100 and locks transfer device 20 to the mobile docking cone 100, as more fully described below.

Figure 6:
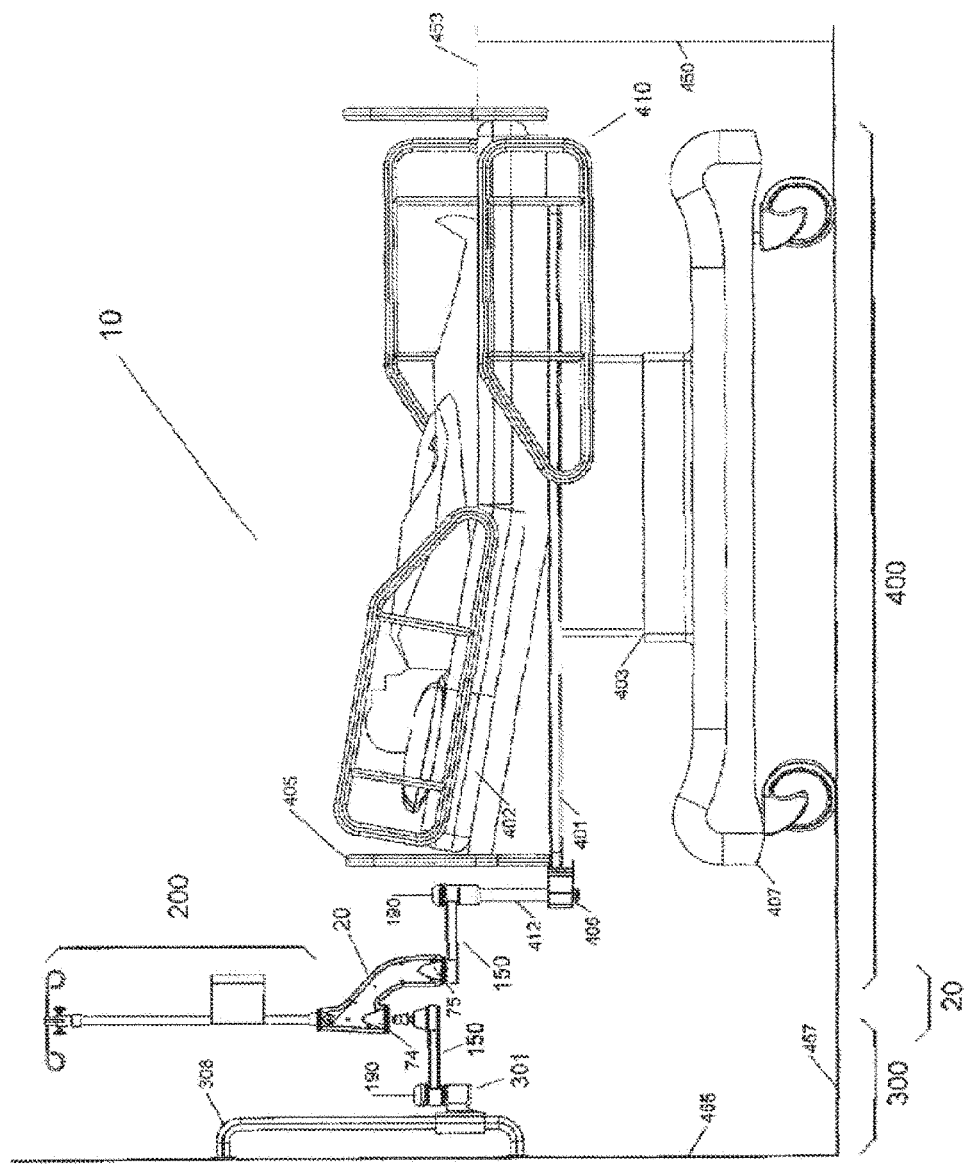
FIG. 6 is a side view of the transfer system docked to a mobile support platform and the mobile support platform raised to undock the transfer device from the stationary platform during transfer.

As shown in FIG. 6, continued activation of lift mechanism 403 lifts transfer device 20 out of engagement with stationary docking cone 100 until the transfer device clears the stationary docking cone. In the preferred embodiment, cone arms 150, mobile cone arm adapter 413, stationary cone arm connector 301, adjustment knobs 190, and upper and lower docking cups 74, 75 of transfer device 20 constitute a system of pivoting linkages that permit caregivers to position patient care apparatus 201 where it is needed for optimal patient care, and the arm length 175, as well as the spacing of upper and lower docking cup axes 462 and 463 offer a practical trade-off between easy adjustability and low cost.

Figure 7:
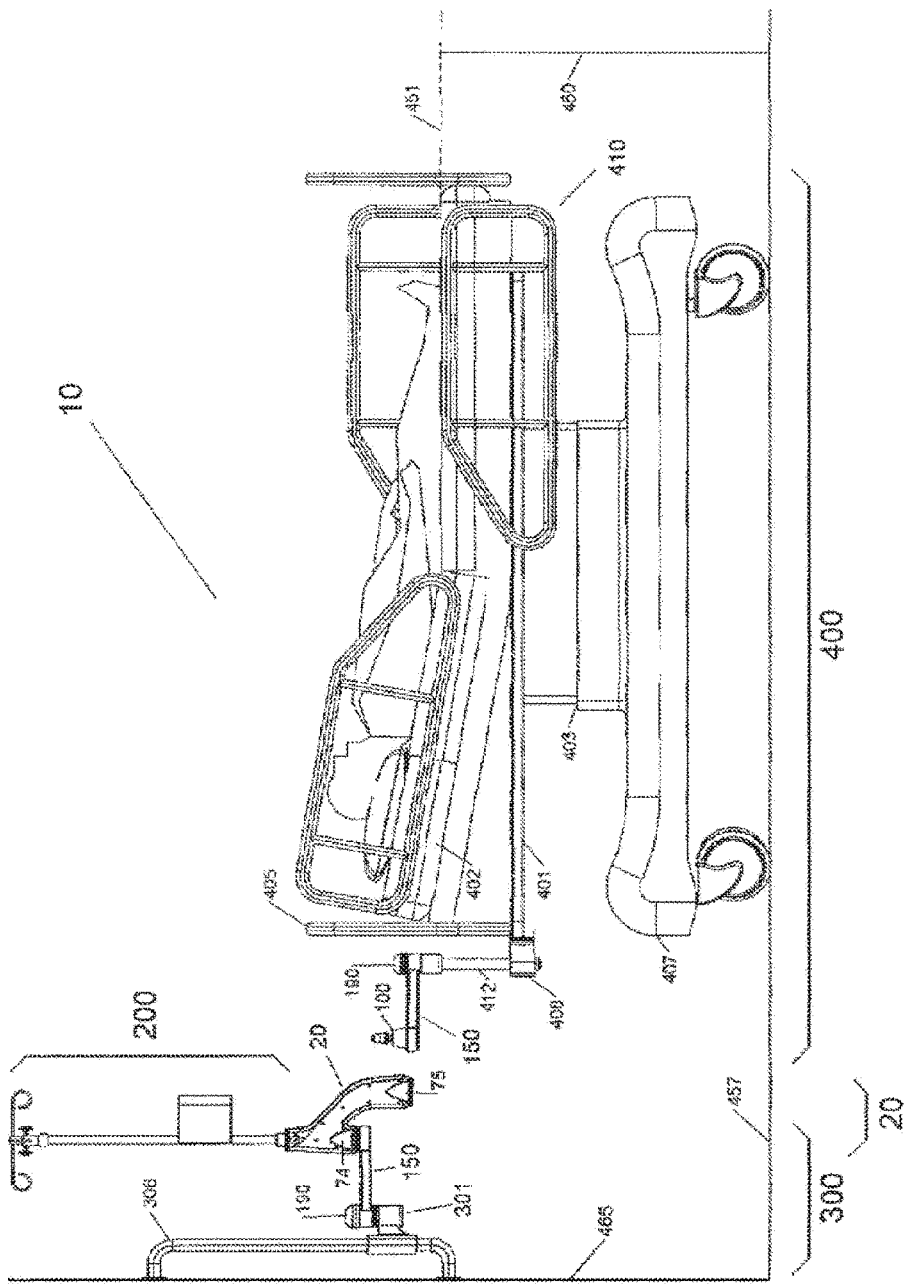
FIG. 7 is a side view of the transfer system docked to a stationery support platform and with the transfer device disengaged from a mobile support platform during transfer.
Figure 8:
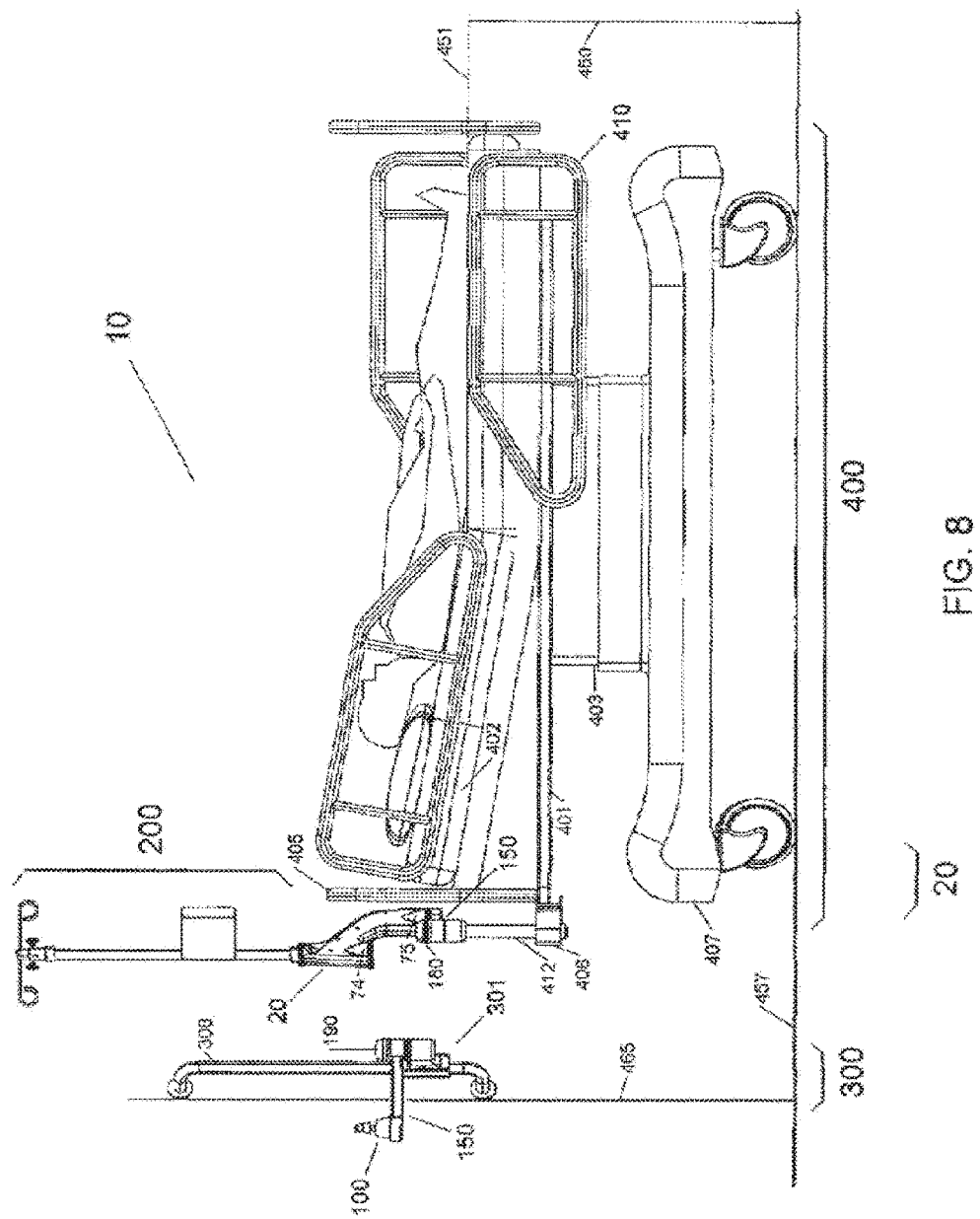
FIG. 8 is a side view of the transfer system docked to a mobile support platform during transfer and the docking arms on the stationary platform and the transfer device on the mobile support platform stowed for transport.

As shown in FIG. 7, moving hospital bed 410 away from stationary support platform 300 and out of docking alignment enables the medical staff to reverse lift mechanism 403 to lower mattress height 450 to the preferred working height 451. As shown in FIG. 8, caregivers are now free to reposition transfer clamp 20 and equipment support structure 200 so it nests closely with hospital bed 410 and the patient's head without disturbing the connections between patient and patient care apparatus. Articulation of transfer device 20 by rotation of cone arms 150 on docking cone axes 460 and bed post axis 461b permits nursing staff to minimize the combined footprint of mobile support platform 400 for efficient and safe transport, in tandem with the patient care apparatus 201, through doorways, corridors and elevators.

In the preferred embodiment, as shown in FIGS. 17-24, transfer device 20 is an assembly of two essentially identical but mirrored housing halves 22 and 23 that are joined along central joint plane 34 and fastened together by screws 42 to form a generally hollow, thin-walled clamshell housing 21 suitable for cost-effective molding or casting. Each housing half 22, 23 has generally smooth, easy-to-clean exterior surfaces 35 comprising label recesses 25 to permit covering assembly screws 42 and other surface irregularities with labels 43 to seal crevices for effective infection control. The interior surfaces 36 of housing halves 22, 23 comprise bosses, ribs and other features that cooperate to retain and fasten pivot pins 26, assembly screws 42, fasteners on which to anchor springs 27 as well as other structural and/or functional elements such as docking cups 60 and support post 41.

Support post 41 is retained by saddle bosses 38, shaped to conform to the outside diameter of support post 41, between first and second housing halves 22, 23, preferably in coaxial relationship with upper docking cup axis 462. Assembly screws 42 are installed to rigidly attach support post 41 to the clamshell housing 21. Support post 41 protrudes from the upper end 33 of clamshell housing 21 to rotatably engage equipment support structure 200.

Figure 19:
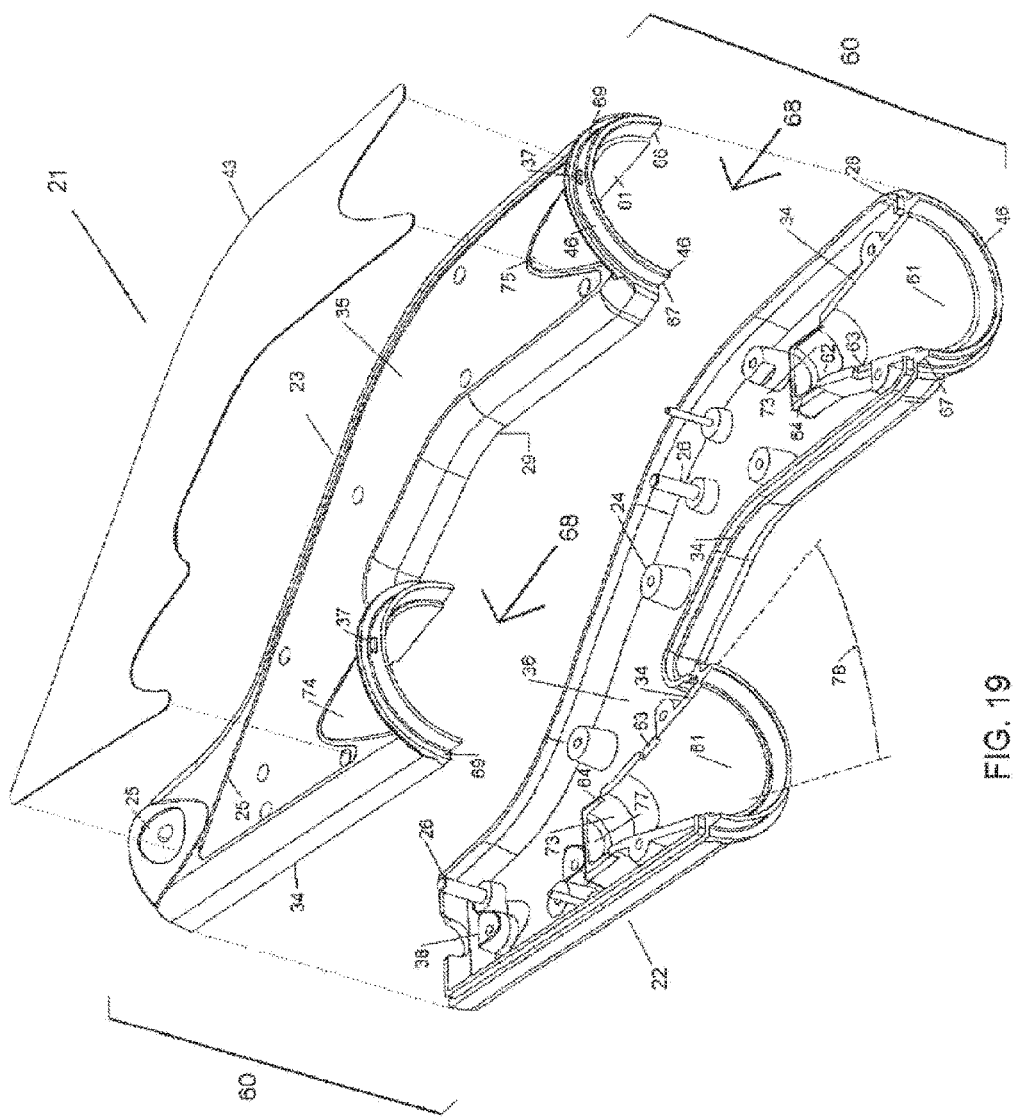
FIG. 19 is a perspective exploded view of the transfer device of the present invention.

As shown in FIG. 19, docking cups 60 are constituted by matching up generally identical but mirrored depressions in the first and second housing halves 23, 24 when the two housing halves are joined to form clam shell housing 21. Upper and lower docking cup axes 462, 463 coincide with the central joint plane 34 of clamshell housing 21 and are generally parallel to each other. Each docking cup 60 constitutes a generally conical cavity 61, with an elongated, cylindrical extension 73 configured to receive docking cone 100 in coaxial alignment.

As shown in FIGS. 19-22, docking cup openings 68 (indicated by arrow 65) face downward and are positioned in the two housing halves 22, 23 such that they are open to the outside for insertion of docking cones 100 without exposing security mechanism 120. Docking cup axes 462 and 463 of the upper and lower docking cup are spaced apart horizontally by cup axis spacing 45. In the preferred embodiment, cup axis spacing 45 is a two to two-and-a-half multiple of the outer ring diameter 278 of docking ring 275 to provide adequate horizontal spacing so users may align docking cones 100 with the respective docking cups 74 and 75 and carry out the docking maneuver with minimal risk of collision or interference between upper and lower cone arms 150 during transfer.

Preferably, the lower docking cup 75 is disposed along bottom cup edge 30 of transfer device 20, and the upper docking cup 74 is positioned higher. Vertical cup spacing 40 between upper and lower docking cups 74 and 75 preferably is approximately equal to the overall cone height 185 to enable docking in case the cone arms of stationary and mobile platforms 300, 400 cross over. Vertical cup spacing 40 assures that users may potentially rotate the transfer device through a full 360 degree rotation when docked on the lower docking cup axis 463 and not otherwise obstructed by hospital bed 110 or other extraneous structures. In the preferred embodiment, vertical cup spacing 40 is approximately 6.75 inches but, depending on specific requirements, may be larger or even zero with both docking cups aligned on the same horizontal plane.

The preferred embodiment of the present invention describes docking cups 60 with cup openings 68 that are open toward the bottom, and docking cones 100 that have their narrow end facing up. While there are advantages regarding security and infection control for this orientation of docking cups and docking cones, upward-opening docking cups and downward-pointing docking cones are within the scope of this invention.

Figure 17:
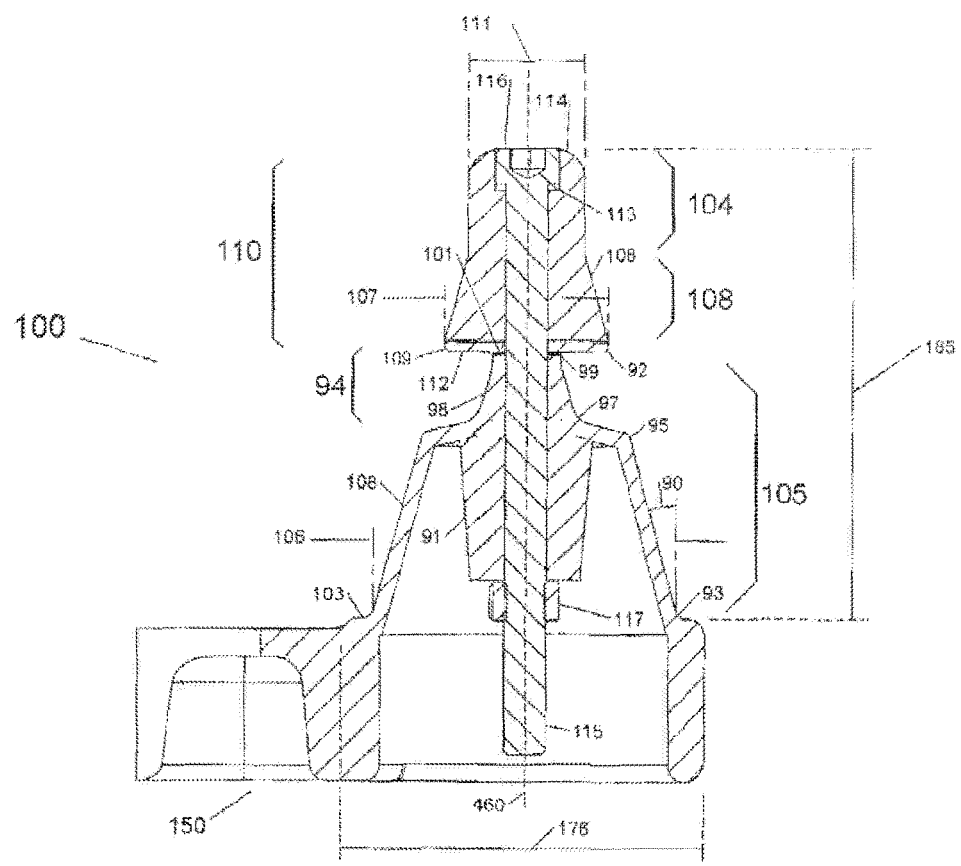
FIG. 17 is a sectional side view of a docking cone taken along line A-A' of FIG. 3.
Figure 18:
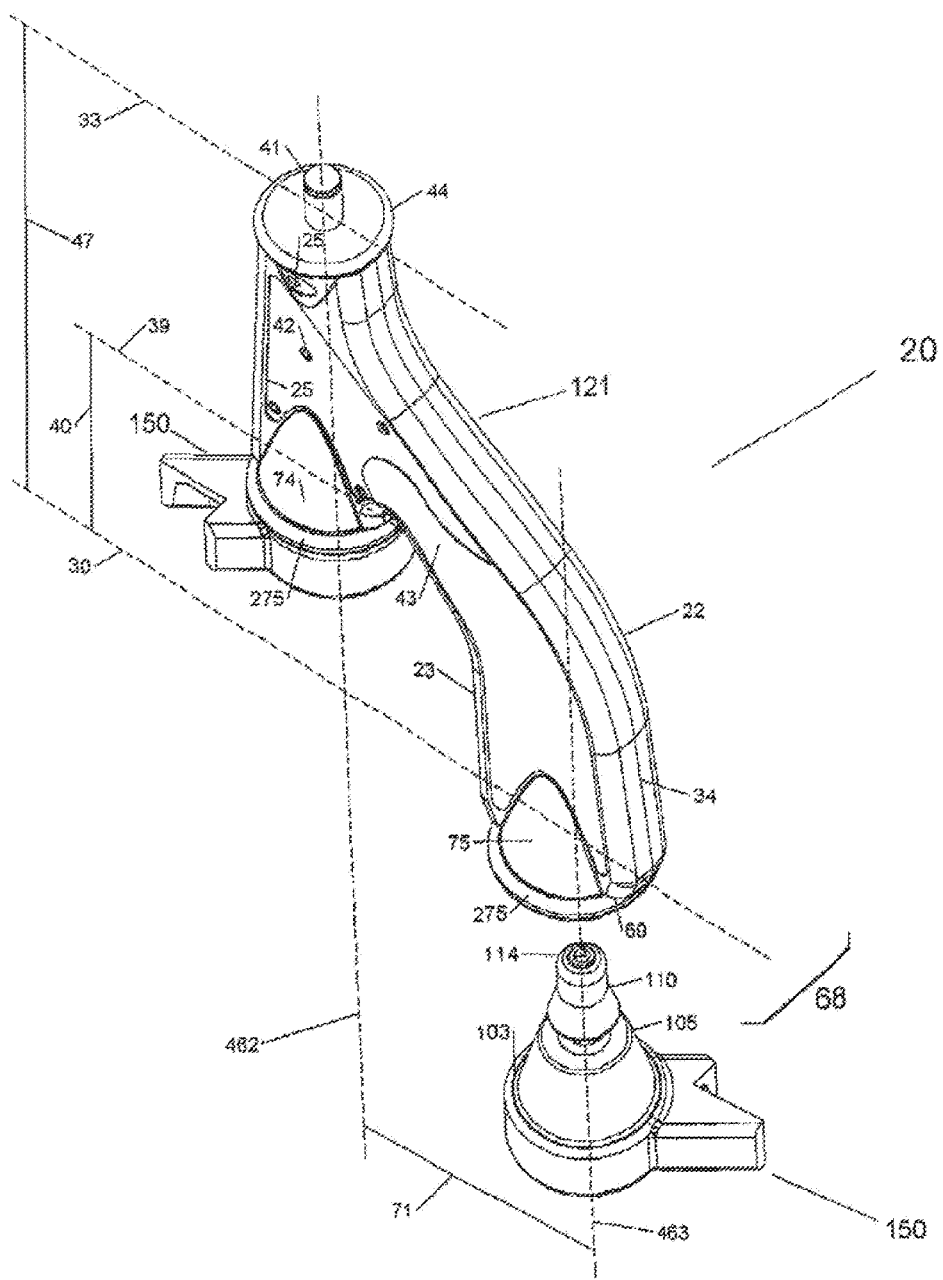
FIG. 18 is a perspective side view of a transfer system with mobile and stationary support platforms partially cut away.
Figure 23:
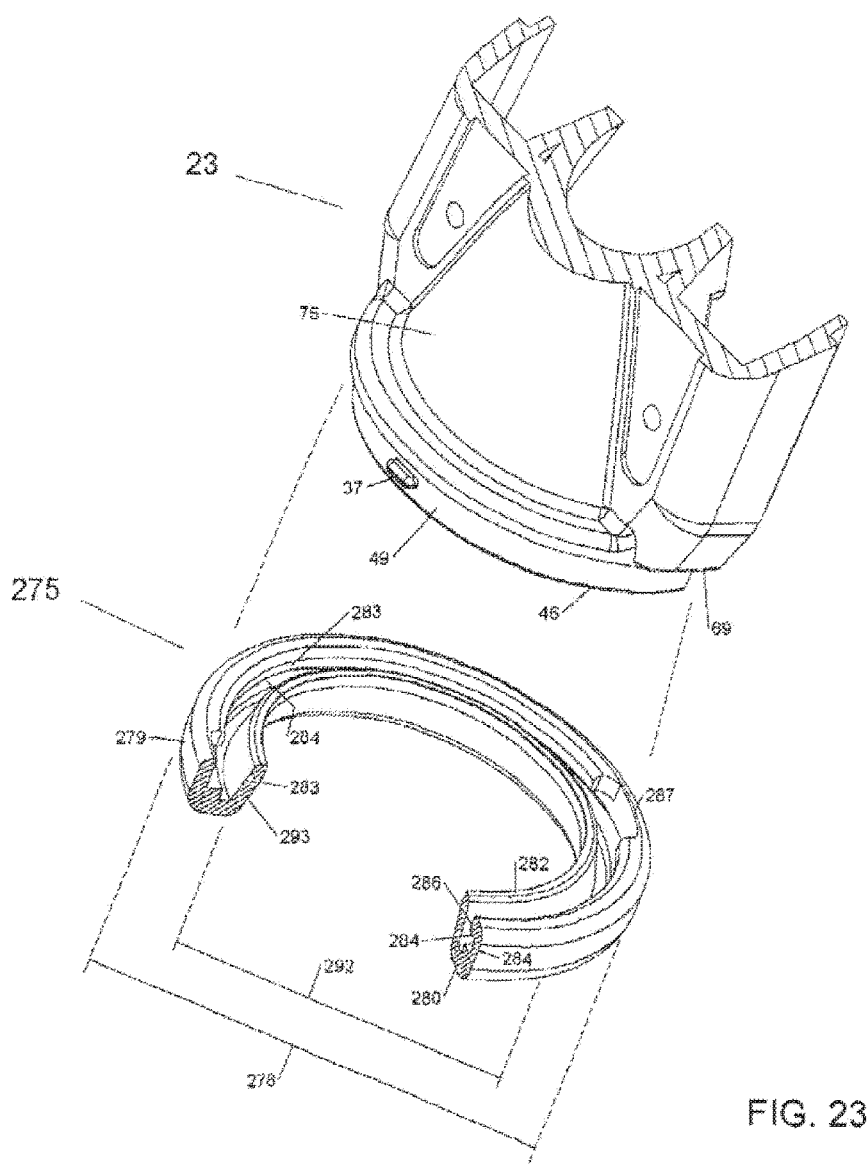
FIG. 23 is an exploded perspective view of a docking ring and a second housing half, with both the docking ring and the second housing half partially cut away.

Docking rings 275 preferably generally are toroid bodies that terminate, reinforce, and provide accurate concentricity to, support flanges 46 of the upper and lower docking cups 74, 75 at cup openings 68. Docking rings preferably are made from a high-strength material with anti-friction characteristics such as a DELRIN or similar acetal resin, high-density polyethylene or other engineering plastics and guide and support transfer device 20 on docking cones 100 during the docking maneuver. As shown in FIG. 23, docking ring 275 has an upper support surface 282 that is in contact with ring support 69 of first and second housing halves, and a bottom support surface 280 that is in contact with base flange 103 of docking cone 100 when docked to transfer device 20 as shown in FIGS. 17 & 18. Registration groove 283 of docking ring 275 has a tapered inner groove surface 285 and a cylindrical outer groove surface 286, and is sized and positioned to receive ring support flanges 46 that depend from the bottom of ring supports 69 of housing halves 22, 23 and form a coaxial and load-bearing joint between docking rings 275 and cup openings 68. Retaining undercut 284 extends radially from outer groove surface 286 of registration groove 283 and receives keys 37 that project radially from outer faces 49 of ring support flanges 46 when docking ring 275 is connected to cup opening 68. Keys 37 of first and second housing halves 22 and 23 may be introduced into retaining undercut 284 of docking ring 275 though keyways 287 and, upon introduction, docking ring 275 may be rotated on ring support flange 46, with keys 37 in engagement with retaining undercut 284, to secure docking ring 275 to clamshell housing 21 in the manner of a bayonet closure. Bottom support surface 280, base flange fillet 93 and the conical portion 108 of cone base 105 of docking cone 100 are sized to receive the bottom support surface 280 and cone support 293 in concentric, nested and load-bearing relationship. Outer ring surface 279 projects beyond the bottom edges of the docking cup 60 and protects the cup openings 68 against impact and abrasion.

As shown in FIGS. 1, 16, 17 & 25, a first cone arm 150 is attached to stationary support platform 300 and a second cone arm 150 is attached to mobile platform 400, and each cone arm 150 comprises a docking cone 100 at its distal end 174 that is configured for docking engagement in docking cups 74, 75 of transfer device 20.

Docking cone 100 is a frustoconical body, and cone base 105 has a cone base diameter 176 that is substantially equal to distal end arm width 176. Docking cone 150 has a base flange 103 with base flange fillet 93 and transitions into cylindrical portion 104 at its narrow, upper end. Between cone tip 114 and cone base flange 103, the outer surface of conical portion 108 of docking cone 100 steps closer to the cone's central axis 111 to form security notch 94. Notch lower edge 95 and cone base upper end 99 demise the lower and upper edges, respectively, of security notch 94. The outer diameter of plate support surface 101 at cone base upper end 99 is substantially smaller than upper base diameter 107 of conical portion 108 of upper cone 110, and engagement plate 109 may be positioned, in coaxial relationship, between plate support surface 101 and the bottom surface of conical portion 108. Security mechanism 120 engages security notch 94 in the secured cone position 130, and notch upper edge 92 of engagement plate 109 protects the upper cone 110 against damage from security levers 121, 122. Engagement plate 109 is a washer, preferably made from steel with an outside diameter that is substantially equal to upper base diameter 107 of upper cone 110. Notch fillet 97 and notch portion 98 form the transition between plate support surface 101 and notch lower edge 95 to provide a space for engagement of security latches 126, 127 during activation of security mechanism 120. Upper cone 110 preferably is made from a tough engineering plastic including a DELRIN or similar acetal resin, high-density polyethylene or any other structural material with low friction characteristics and is fastened to cone base 105 by cone bolt 115 in concentric relationship with docking cone axis 460. Cone bolt head 116 is recessed into cone tip recess 113 of upper cone 110 to form a continuous, smooth cone tip 114.

Cone bolt 115 optionally may be inserted from below and in threaded engagement with a blind, internally threaded hole (not shown) in cone tip 114. In the preferred embodiment, cone bolt 115 penetrates cone bolt holes 118 of upper cone 110, engagement plate 109 and inner cone boss 91 of cone base 105. Retaining nut 117 is threaded onto cone bolt 115 and tightened against inner cone boss 91 to assemble upper cone 110, engagement plate 109 and cone base 105 into a strong, load-bearing docking cone 100. To facilitate low-cost manufacturing of cone arms 150 and docking cones 100, processes such as molding or casting may be employed and therefore security notch 94 preferably is created by an assembly of easily fabricated parts rather than as a single part where security notch 94 may be an undercut. However, docking cones 100 may also be formed as a single part. Cone base 105, preferably made from metal such as aluminum or other structural materials, may be cast together with cone arm 150 in one piece or assembled from separate components 105, 150 by welding, mechanical fasteners or other known joining methods.

As shown in FIGS. 20-22 & 25, when the docking maneuver is initiated, docking cone 100 may not be fully engaged in docking cup 60. Docking cup 60 and docking cone 100 cooperate during docking to minimize negative consequences of misalignment between docking cone axis 460 on the one hand and arm connector axis 461a and/or bed post axis 461b on the other hand, as may be expected in the real-life hospital environment, and to enable users to easily target the cone tip 114 of docking cone 100 for entry into docking cup 60. During the transfer maneuver, cone tip 114 progressively slides up along the inner surface of conical cavity 61 inside of docking cup 74 or 75, until cone tip 114 enters cylindrical extension 73 of docking cup 60. During the docking maneuver, the external surfaces of the external base 105 and the upper cone 110 are in contact with, and progressively slide up along, the conical inner contour of the bottom support surface 280 of docking ring 275.

The inner surface of conical cavity 61 of docking cups 74 and 75 is sized and shaped to be generally concentric and coaxial with the tapered external wall of conical portion 108 of cone base 105, and with the tapered external walls of upper cone 110. The conical cavity 61 has a cylindrical extension 73 that is generally concentric with, and sized to receive, cone tip 114. The inner conical contour 280 of docking ring 275 has a control diameter 292 that is substantially equal to the cone base diameter 106, and shaped to be supported by the conical exterior walls of cone base 105 and base flange fillet 93, when fully docked to docking cone 100 in coaxial, load-bearing relationship with either upper docking cup axis 462 or lower docking cup axis 463.

In the preferred embodiment, contact between docking cone 100 and docking cups 74, 75 is restricted to designated structures with low-friction characteristics in order to control friction and wear. When docking cone 100 and docking cups 74, 75 are fully docked, cone tip 114 is in substantial coaxial and concentric engagement with the cylindrical bore 62 of cylindrical extension 73, and cone tip 114 is in substantial sliding contact with inner end surface 77 of cylindrical extension 73. Also, when fully docked, cone tip 114 is in sliding contact with the inner surface of cylindrical bore 62, and base flange 103 and base flange fillet 93 of docking cone 100 are in substantially concentric sliding contact with upper support surface 202, bottom support surface 280 and cone support 293 of cone ring 275, thereby creating a contact-free clearance space 79 by which abrasion-sensitive surfaces are separated.

Figure 20:
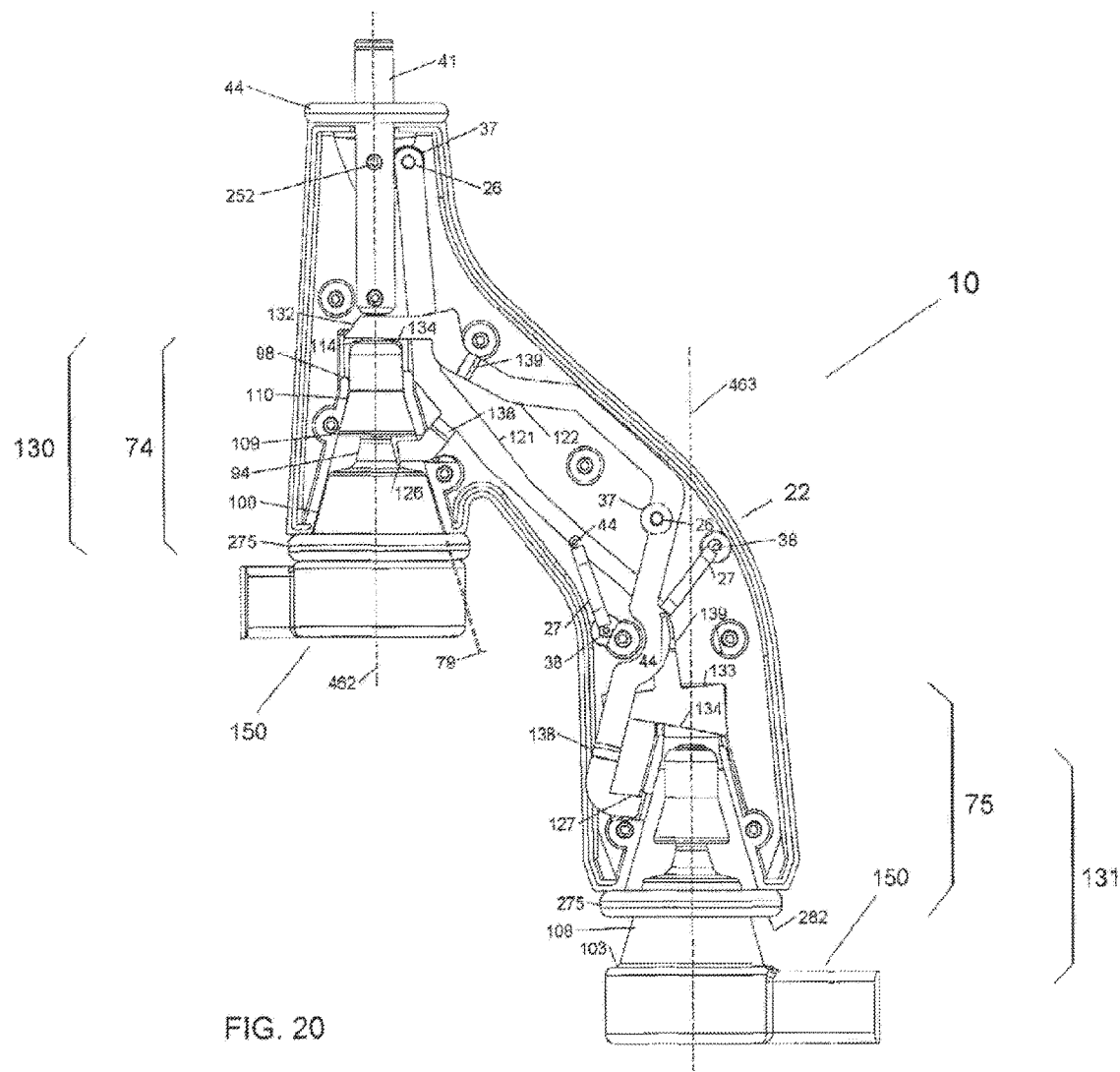
FIG. 20 is a side view of the transfer system with mobile and stationary support platforms partially cut away, the transfer device shown in cross section with a docking cone engaged in the upper docking cup and a lower docking cone disengaged.
Figure 22:
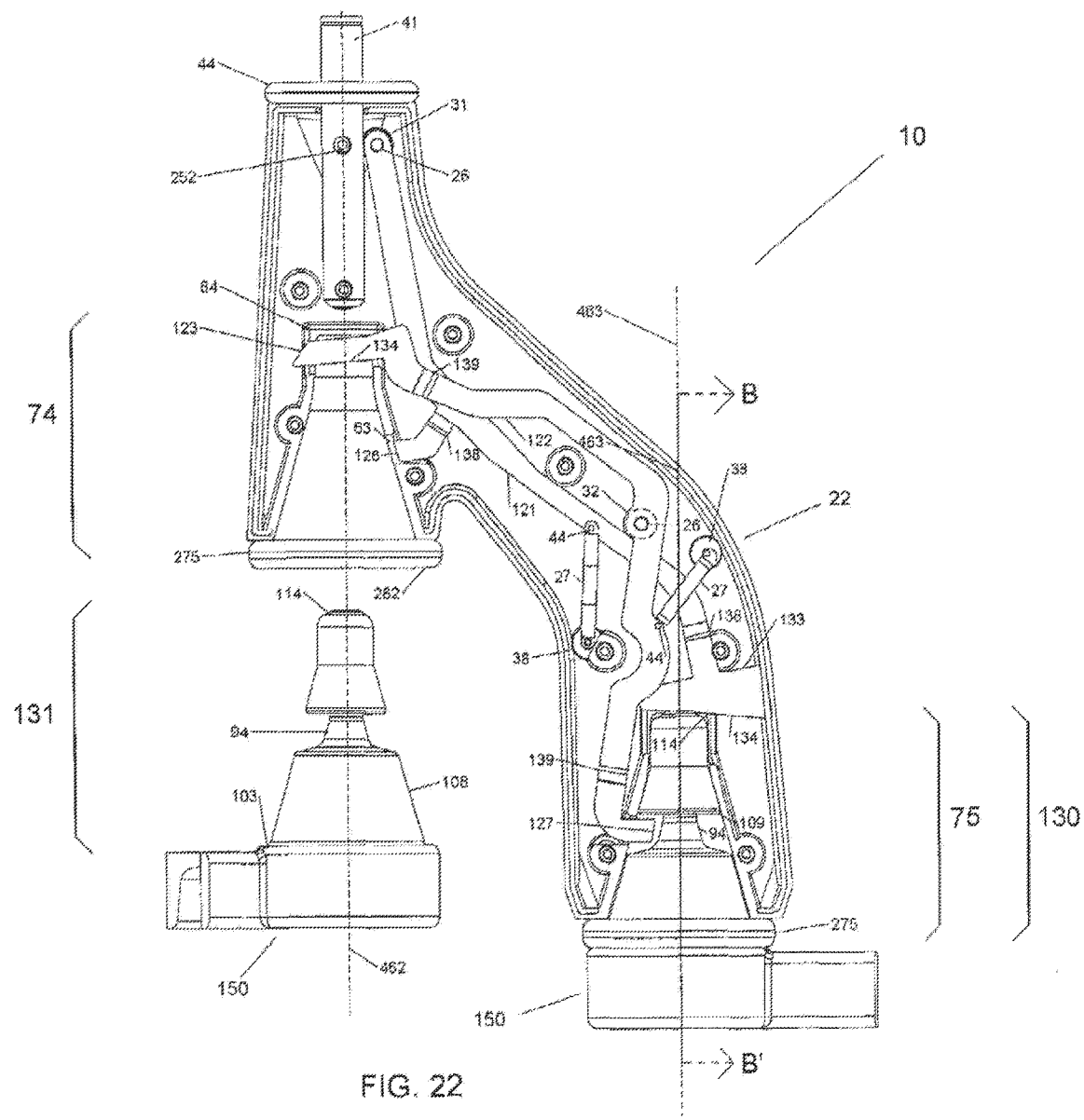
FIG. 22 is a side view of the transfer system with mobile and stationary support platforms partially cut away, the transfer device shown in cross section with a docking cone engaged in a lower docking cup and a docking cone disengaged from an upper docking cup.
Figure 24:
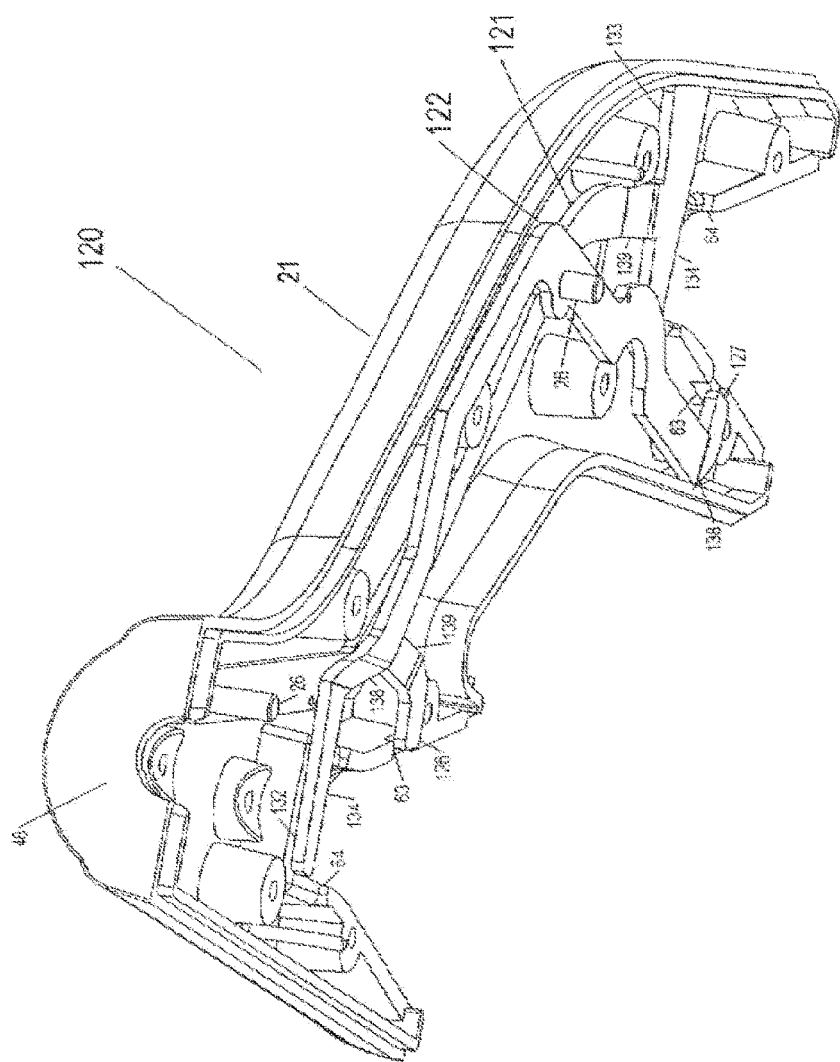
FIG. 24 is a perspective top view of a first housing half with an upper security lever and a lower security lever assembled.
Figure 25:
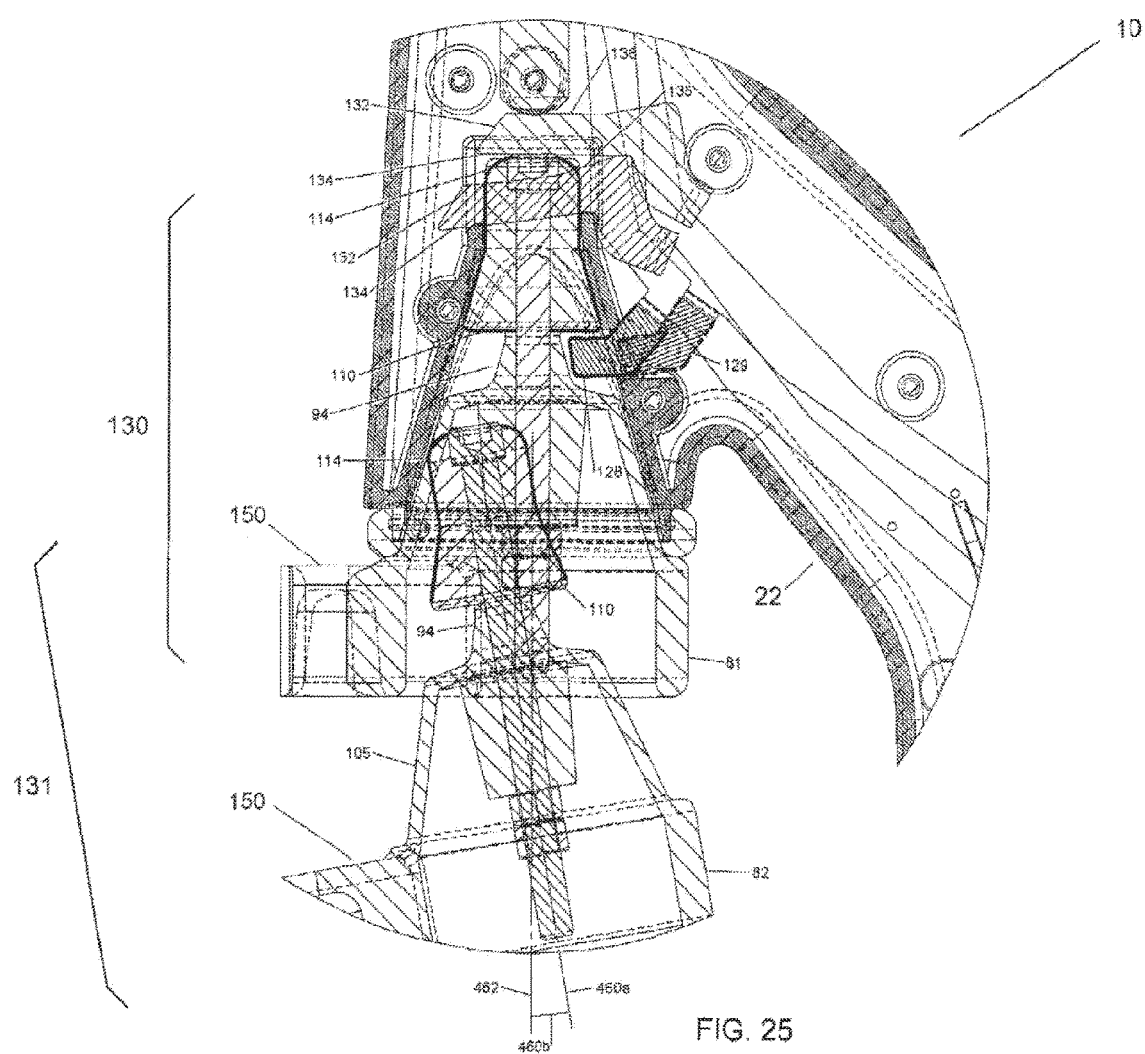
FIG. 25 is a schematic, sectional side view of a transfer device, with the stationary support platform partially cut away, the lower docking cup and equipment support structure cut away, and showing one docking cone docked to an upper docking cup and a second docking cone in misaligned position in preparation of docking, taken along line C-C' of FIG. 5.
Figure 26:
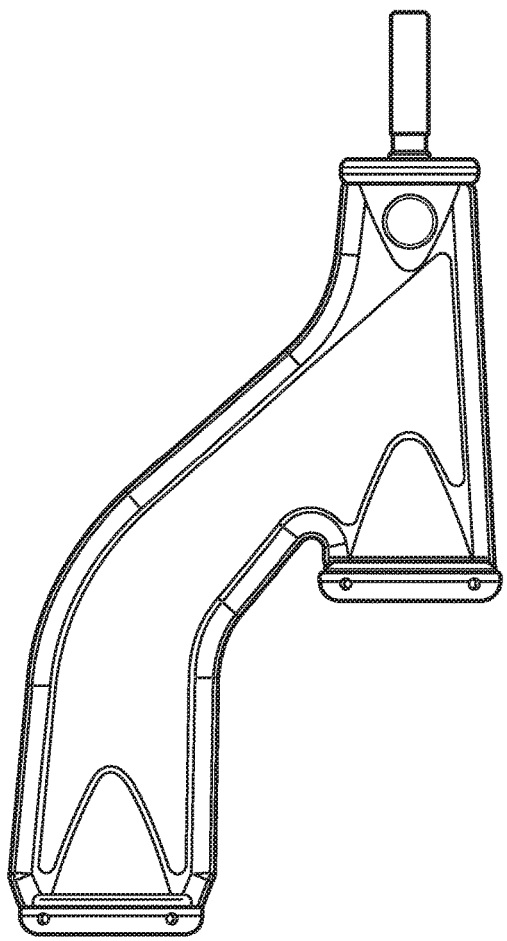
FIGS. 26-32 are various views of a first embodiment of the transfer device of the present invention.
Figure 27:
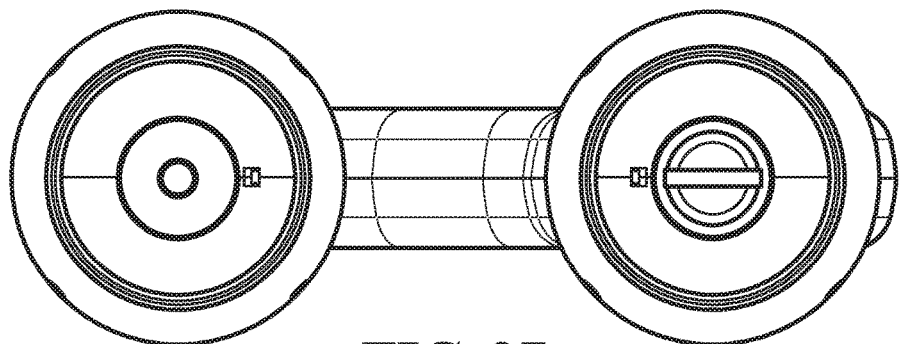
Figure 29:
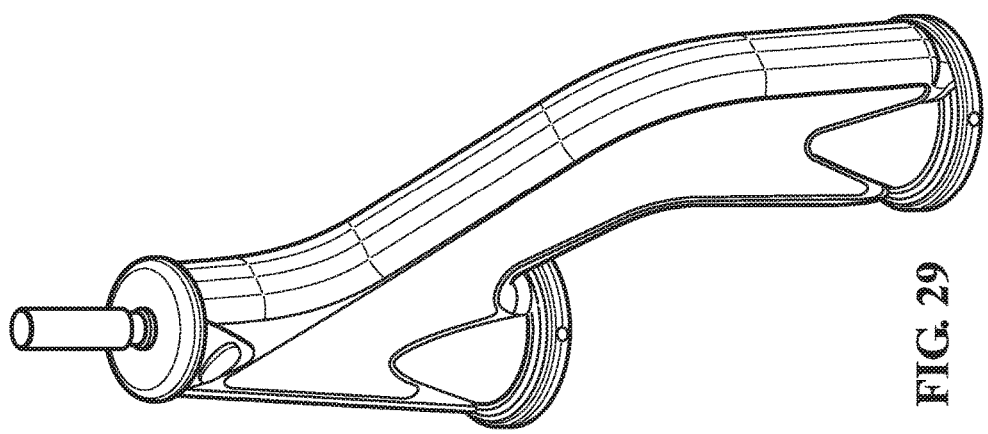
Figure 28:
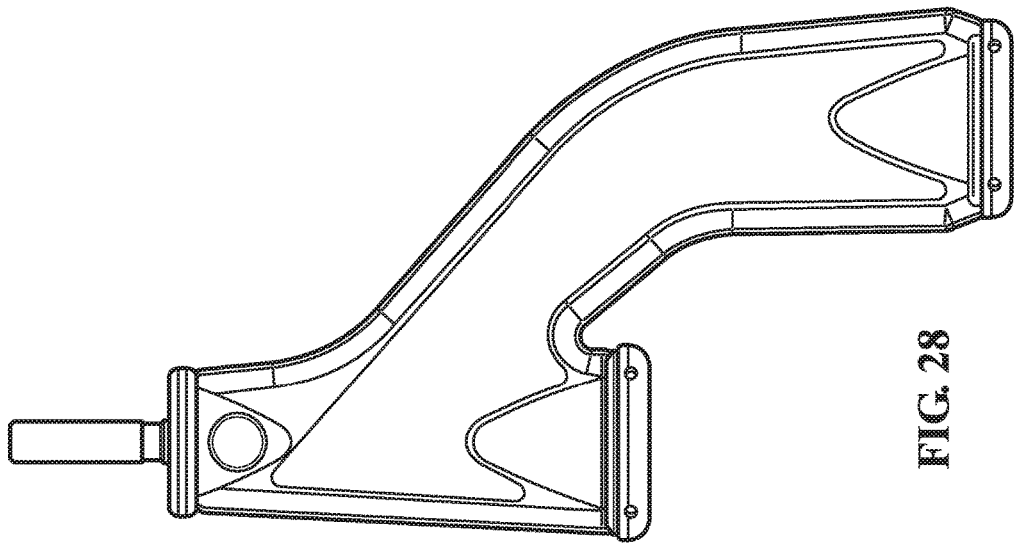
Figure 30:
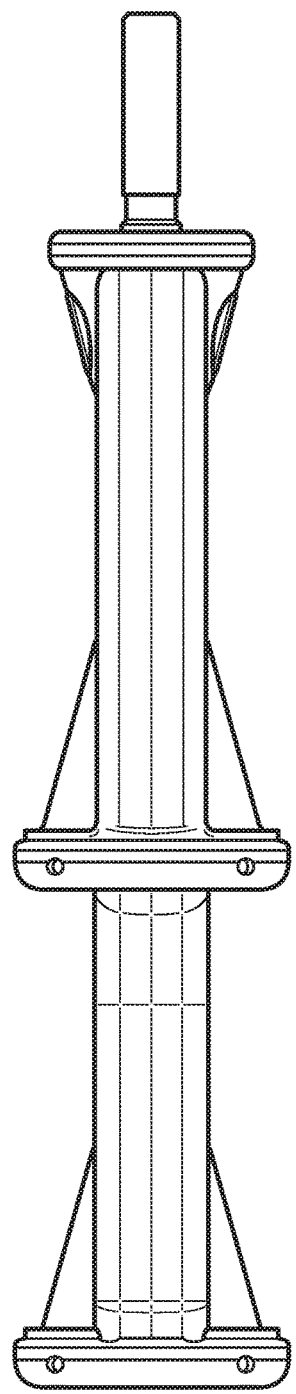
Figure 31:
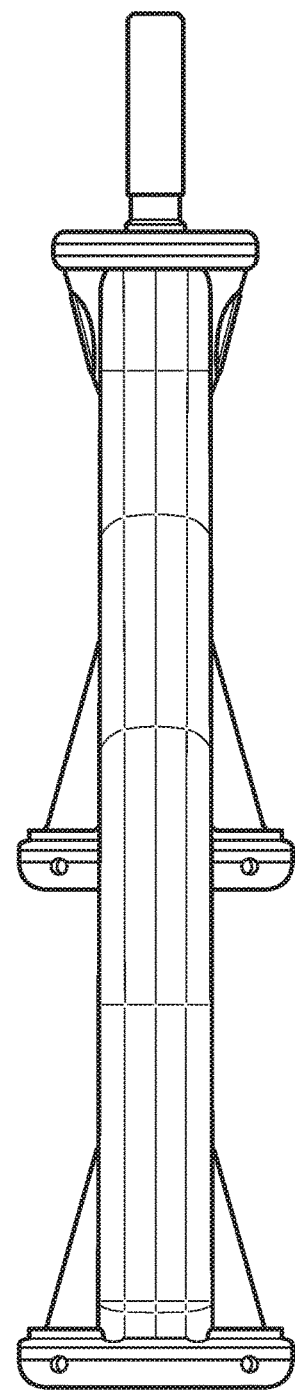
Figure 32:
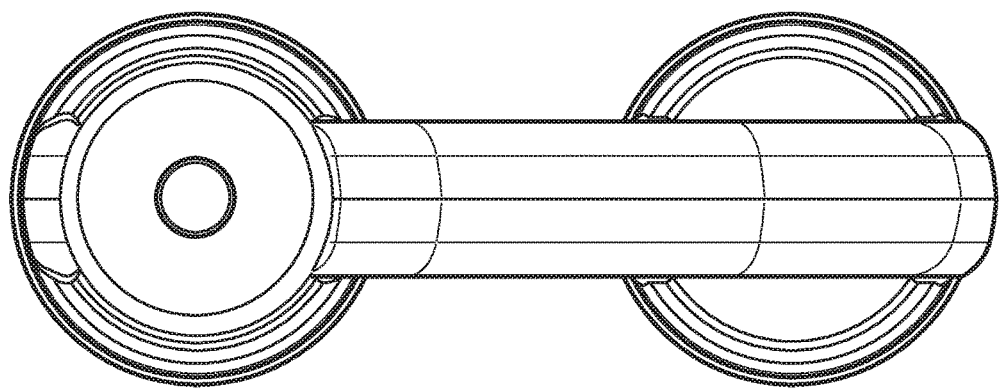

As shown in FIGS. 20 & 24, security mechanism 120 minimizes the risk of accidentally disconnecting or dislodging transfer device 20 from a docking cone 100 to which it may be docked. Security mechanism 120 is fully enclosed inside of clamshell housing 12. When a first docking cone is in docking engagement with upper docking cup 74 of transfer device 20, transfer device 20 cannot be removed from the first docking cone as long as lower docking cup 75 is not in docking engagement with a second docking cone. With reference to FIG. 22, when a second docking cone is in docking engagement with lower docking cup 75 of the transfer device, transfer device 20 cannot be removed from the second docking cone as long as docking cup 74 is not in docking engagement with the upper docking cup 74. Thus, security mechanism 120 prevents transfer device 20 from being removed from a stationary platform 300 or a mobile platform 400 unless, and only under the condition that, transfer device 20 simultaneously is also fully and securely docked to another support platform to which it is being transferred. Only simultaneous, full docking engagement inside both docking cups 74,75 by two docking cones 100 causes security mechanism 120 to automatically release both the security latches 126 and 127, permitting a caregiver the choice of either releasing the transfer device 20 from the cone arm 100 docked to the upper docking cup 74, or releasing the transfer device 20 from the cone arm 100 docked to the lower docking cup 75. Extracting a first docking cone 100 by a distance of ¼ inch or less from either docking cup 74 or 75 causes the security mechanism 120 to engage the second docking cone, and vice versa, without operator intervention except user activation of the lift mechanism 403 of hospital bed 410 to cause the docking cone 100 attached to the mobile cone arm adapter 413 to be raised or lowered, as the case may be, to control the docking maneuver, as described more fully below. Anyone versed in the art will appreciate that other known means, both manual and powered, may be substituted for the lift mechanism of a hospital bed in order to activate the docking maneuver and security mechanism of this invention.

Upper security lever 212 and lower security lever 122 cooperate with security notch 94 and cone tip 114 of docking cone 100, and with upper and lower docking cups 74 and 75 to retain a docking cone in docking engagement with its respective docking cup. With reference to FIG. 20, when a first docking cone 100 is in docking engagement with upper docking cup 74 and no docking cone 100 is in docking engagement with lower docking cup 60, upper security lever 121 securely retains the first docking cone in docked relationship with transfer device 20. Analogously, with reference to FIG. 22, when a second docking cone 100 is in docking engagement with lower docking cup 75 and no docking cone 100 is in docking engagement with upper docking cup 60, lower security lever 122 securely retains the second docking cone in docked relationship with transfer device 20.

Figure 21:
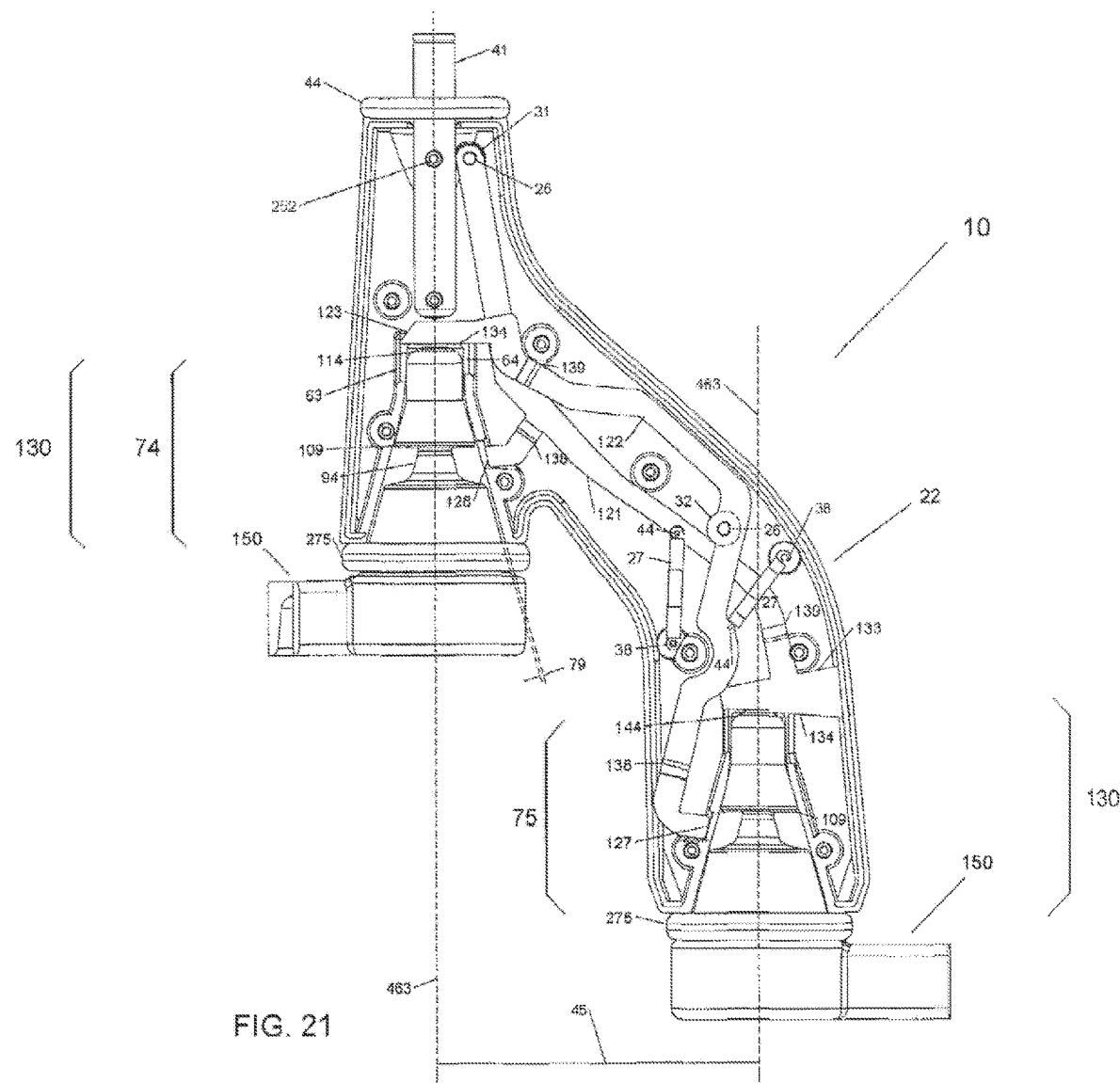
FIG. 21 is a side view of the transfer system with mobile and stationary support platforms partially cut away, the transfer device shown in cross section with a docking cone engaged in a lower docking cup and a docking cone engaged in an upper docking cup during transfer.

Simultaneous full docking engagement of two docking cones 100 in transfer device 20, as shown in FIG. 21, with one docking cone 100 seated in the upper docking cup 74 and the other docking cone 100 seated in the lower docking cup 75, causes upper security lever 121 to release the first docking cone, and security lever 122 to release the second docking cone.

Security levers 121 and 122 have analogous functions and share key structures and features such as a pivot holes 123, security latches 126 and 127, and cone feelers 132 and 133, and are both shaped to clear screw bosses 24 and pivot boss 37, as well as sidewalls and other internal features to avoid collisions when pivoting between secured cone position 130 and released cone position 131. Security levers 121 and 122 preferably are made from sheet steel or other rigid, structural materials.

Pivot pins 124 are trapped between upper and lower pivot bosses 31, 32, respectively, on the inside surfaces 36 of first and second housing halves 22 and 23. Security lever 121 and security lever 122 are both rotatably attached to pivot pins 124 at pivot holes 123 to permit each security lever to pivot between a first secured cone position 130 to a second released cone position 131. Each security lever 121, 122 comprises a security latch 126, 127, respectively, that pivots from a first secured position 130 to a second released position 131, or into and out of engagement with security notch 94 of docking cone 100 to control retention of the docking cone in the respective docking cup of transfer device 20. Each security lever 121, 122 also comprises a security cone feeler 132, 133 that causes security levers 121, 122 to pivot from a first secured cone position 130 to a second released cone position 131 when pivotably displaced by the cone tip 114 of a docking cone 100 during transfer.

In the preferred embodiment, as shown in FIGS. 20-24, upper and lower docking cups 74, 75 are disposed along upper cup edge 39 and lower cup edge 30, respectively, requiring each of the security levers 121, 122 to have a different configuration and shape. Thus, each security latch 126, 127 and each cone feeler 132, 133 is positioned on its respective security lever at a different position in relation to its respective pivot hole 123, as more fully described below.

As shown in FIGS. 21-25, a pivot hole 123 is located at the upper end of upper security lever 121 and a lower cone feeler 133 is located at the bottom end of upper security lever 121. Pivot pin 124 is pivotably attached at pivot hole 123 to upper pivot boss 31 on the interior surfaces 36 of clamshell housing 121, and upper pivot boss 31 is located above upper docking cup 74 and near upper docking cup axis 462. Lower cone feeler 133 depends from upper security lever 121 in an offset relationship by offset 138. Upper security latch 126 is located between pivot hole 123 and lower cone feeler 133 and also depends from upper security lever 121 in an offset relationship by offset 138. Offset 138 causes lower cone feeler 133 and upper security latch 126 to be in coplanar relationship. Lower cone feeler 133 and upper security latch 126 are both sized and positioned to align with docking cone axes 460 when cones 100 are fully docked in upper and lower docking cups 74 and 75 and cooperate with cone tip 114 of docking cone 100 in the lower docking cup 75 and security notch 94 of docking cone 100 in the upper docking cup 74.

As also shown in FIGS. 21-25, lower security latch 127 is located at the lower end of lower security lever 122 and upper cone feeler 132 is located at the upper end of lower security lever 122. Pivot hole 123 is located between the lower security latch 127 and upper cone feeler 132, and is pivotably attached to lower pivot boss 32 on the interior surfaces 36 of clamshell housing 121 by pivot pin 124. Lower pivot boss 32 is located above lower docking cup 75 and near lower docking cup axis 463 and upper cone feeler 133 depends from lower security lever 122. Lower security latch 127 is located below pivot hole 123 and upper cone feeler 132 is located above pivot hole 123, and both lower security latch 127 and upper cone feeler 132 depend from lower security lever 122 in a reverse-offset relationship by reverse-offset 139. Reverse-offset 139 causes upper cone feeler 132 and lower security latch 127 to be in coplanar relationship. Upper cone feeler 132 and lower security latch 127 are both sized and positioned to align with docking cone axes 460 when cones 100 are fully docked in upper and lower docking cups 74 and 75 and cooperate with cone tip 114 of docking cone 100 in the upper docking cup 74 and security notch 94 of docking cone 100 in the lower docking cup 75.

Upper security latch 126 and lower cone feeler 133 are offset from upper security lever 121 in one direction (138) and lower security latch 127 and upper cone feeler 132 are offset from lower security lever 121 in the opposite direction (139). Because upper and lower security latches 126 and 127 as well as upper and lower cone feelers 132 and 133 are coplanar and positioned within the clamshell housing 121 in parallel alignment with, and centered upon, central joint plane 34, upper and lower security levers 121, 122 are positioned on different panes within clamshell housing 21 so that they do not collide when independently pivoting between secured cone position 130 and released cone position 131.

As shown in FIG. 19, latch clearance notches 63 and feeler clearance notches 64 in the first and second housing halves 22 and 23 permit security latches 126 and 127, and cone feelers 132 and 133, to extend into the conical cavities 61 of docking cups 74, 75 where security latches and cone feelers 126, 127, 132 and 133, respectively, are positioned to interact with docking cones 100 that may move into and out of docking relationship with docking cups 74 and 75, as previously described.

Springs 27 are attached between spring anchors 44 of each security lever 121, 122 and spring bosses 38 on housing halves 22, 23 in order to urge each security lever 121 and 122 into its respective secured cone position 130 to provide firm engagement of upper and lower security latches 126, 127 in the respective security notches 94, and position upper and lower cone feelers 132, 133 for activation by a cone tip 144 during docking.

When docking cone 100 is firmly seated in upper docking cup 74, upper security latch 126 is in full engagement with security notch 94 of the docking cone 100 engaged in cup 74. Conversely, when docking cone 100 is firmly seated in lower docking cup 75, lower security latch 127 is in full engagement with security notch 94 of the docking cone 100 engaged in cup 75. If upward force is applied anywhere to transfer device 20 through an accidental collision with an object in the environment or an unauthorized attempt to remove the transfer device from engagement with docking cone 100 to which it is attached, either security latch 126 or 127 engages engagement plate 109 of security notch 94 to interdict extraction of transfer device 20 from the docking cone which supports it.

In an alternate embodiment, as shown in FIGS. 40 to 45, transfer device 620 is an assembly having an upper housing 621, a lower housing 622 and a support post 641 received therebetween. Two substantially identical subassemblies 748 are assembled to, and retained by, upper housing 621 in generally equidistant, parallel and symmetric relationship with support post 641. Docking cups 660 are received in upper housing 621 in substantially parallel relationship with, and generally equidistant from, support post 641 and are seated in the upper housing by means of locking rim 628. Lower housing 622 interdigitates with docking cups 660 by means of registration notches 646. Support post 641 is received in the bottom guide 624 of lower housing 622 and retention opening 644 in the upper end 633 of upper housing 621. Support post 641 protrudes from the upper end of upper housing 621 to rotatably engage equipment support structure 200.

As previously described, docking cups 660 are substantially identical and comprise generally identical conical hollows 661, each having an elongated extension 673 to receive upper cone 710 of docking cone 700 in coaxial alignment, as more fully described below. Bottom openings 680 of docking cups 660 face downward and are positioned such that they are open to the outside for insertion of docking cones 700 without exposing security mechanism 720.

Figure 42:
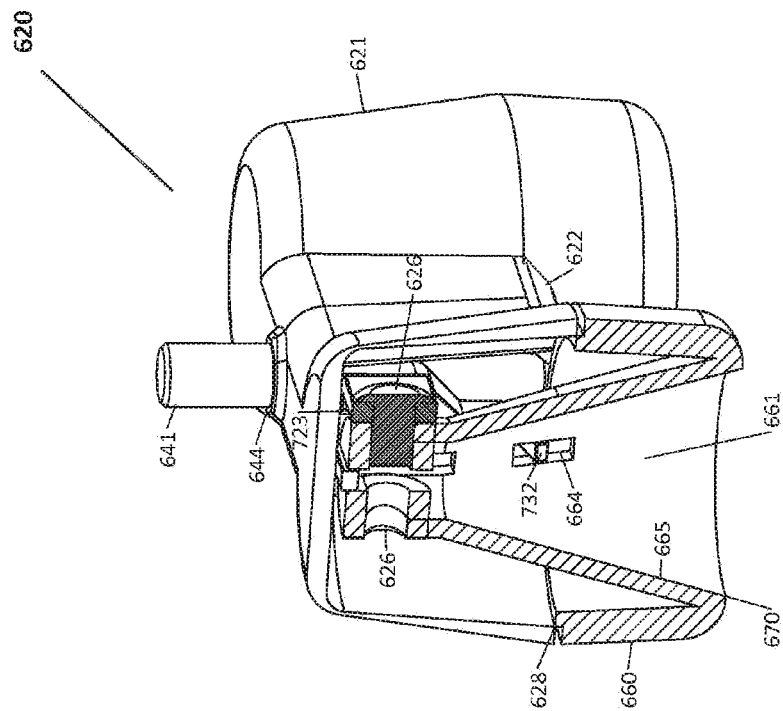
FIG. 42 is a cross sectional view of a third embodiment of the transfer device of the present invention taken along A-A of FIG. 40.
Figure 41:
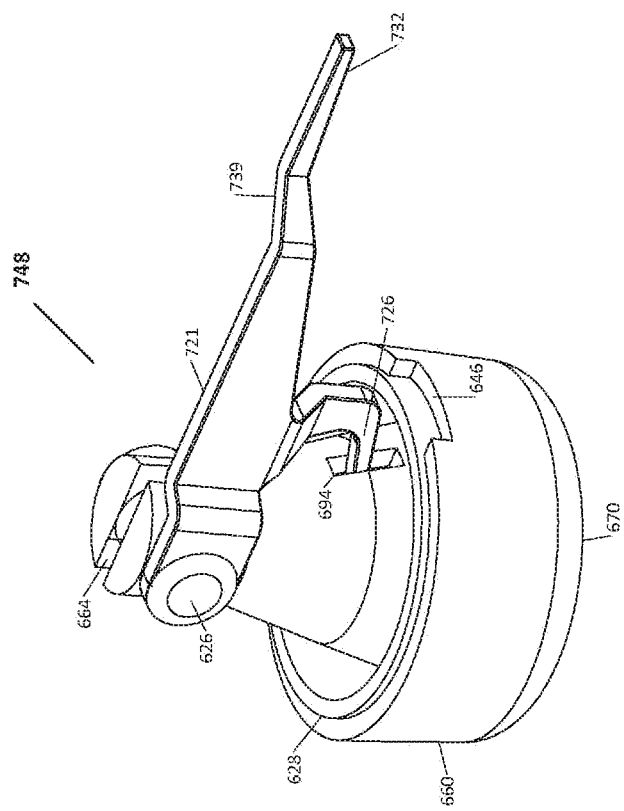
FIG. 41 is an exploded view of one cup of a third embodiment of the transfer device of the present invention with the cover shell removed.
Figure 43:
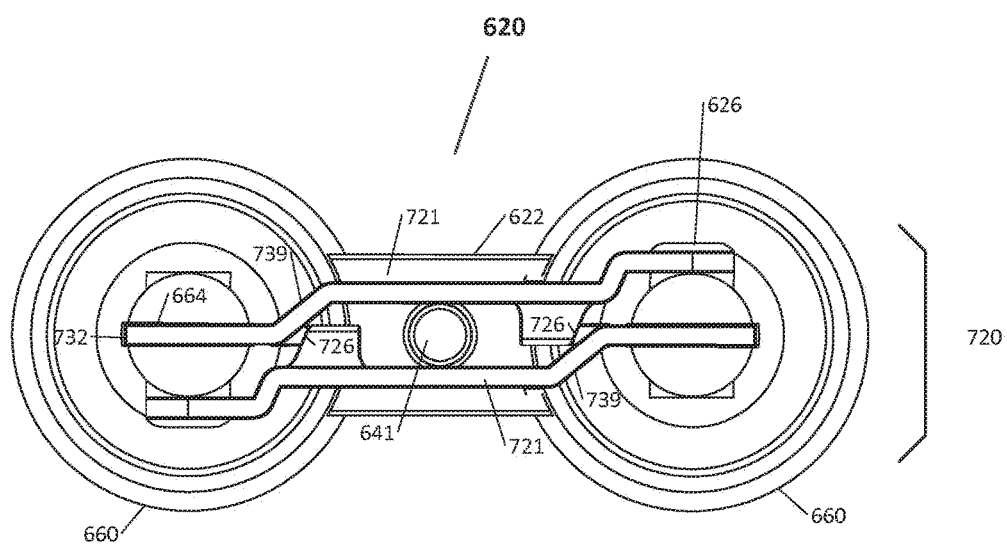
FIG. 43 is a top view of the transfer device with the cover shell removed.
Figure 44:
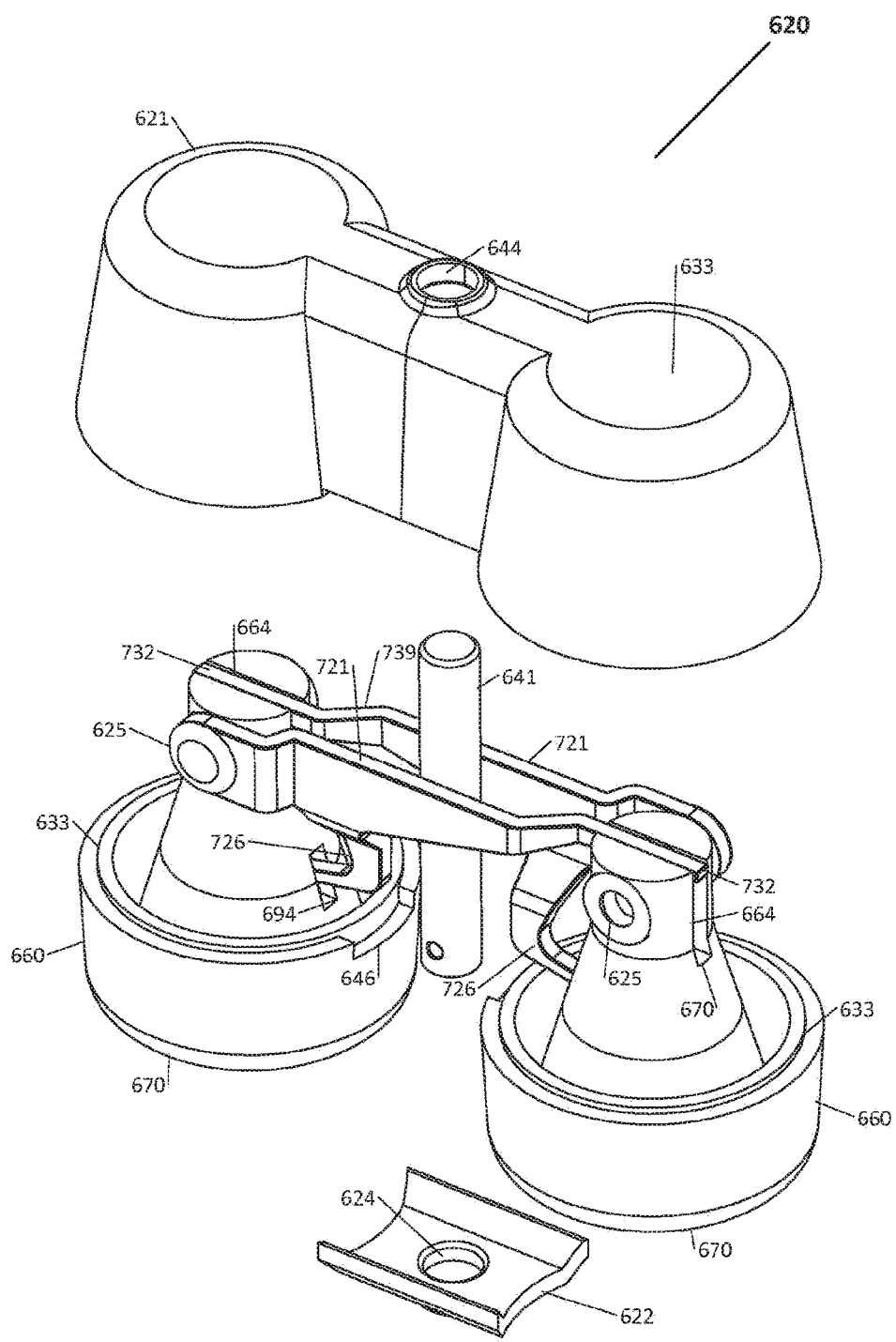
FIG. 44 is an exploded view of the transfer device.

As shown in FIGS. 41 & 42, docking cup 660 preferably is formed as a solid of revolution with an inner conical surface 665 shaped to coaxially receive frustoconical docking cone 700. The docking cup comprises a bottom contour 670 shaped to deflect misaligned insertion of cone tip 711 of upper cone 710; a security notch 694; and a feeler notch 664. Further, docking cup 660 preferably comprises a pivot 626 to pivotally attach security lever 721, thus constituting a self-contained subassembly 748 of a docking cup with integral, pivoting security lever, as shown in FIG. 41. Two substantially identical subassemblies 748 are assembled to, and retained by, upper housing 621 in generally equidistant, parallel and symmetric relationship with post 641.

Each security lever 721 of security mechanism 720 comprises a security latch 726 that pivots from a first secured position to a second released position, or into and out of engagement with security engagement notch 709 of docking cone 700 to control retention of the docking cone in the respective docking cup of transfer device 620. Each security lever 721 also comprises a cone feeler 732 that causes the security latch 726 of said security lever 721 to pivot from a first secured position to a second released position in response to being displaced upward, against the bias of spring 747 (not shown), by the cone tip 711 of docking cone 700.

Figure 45:
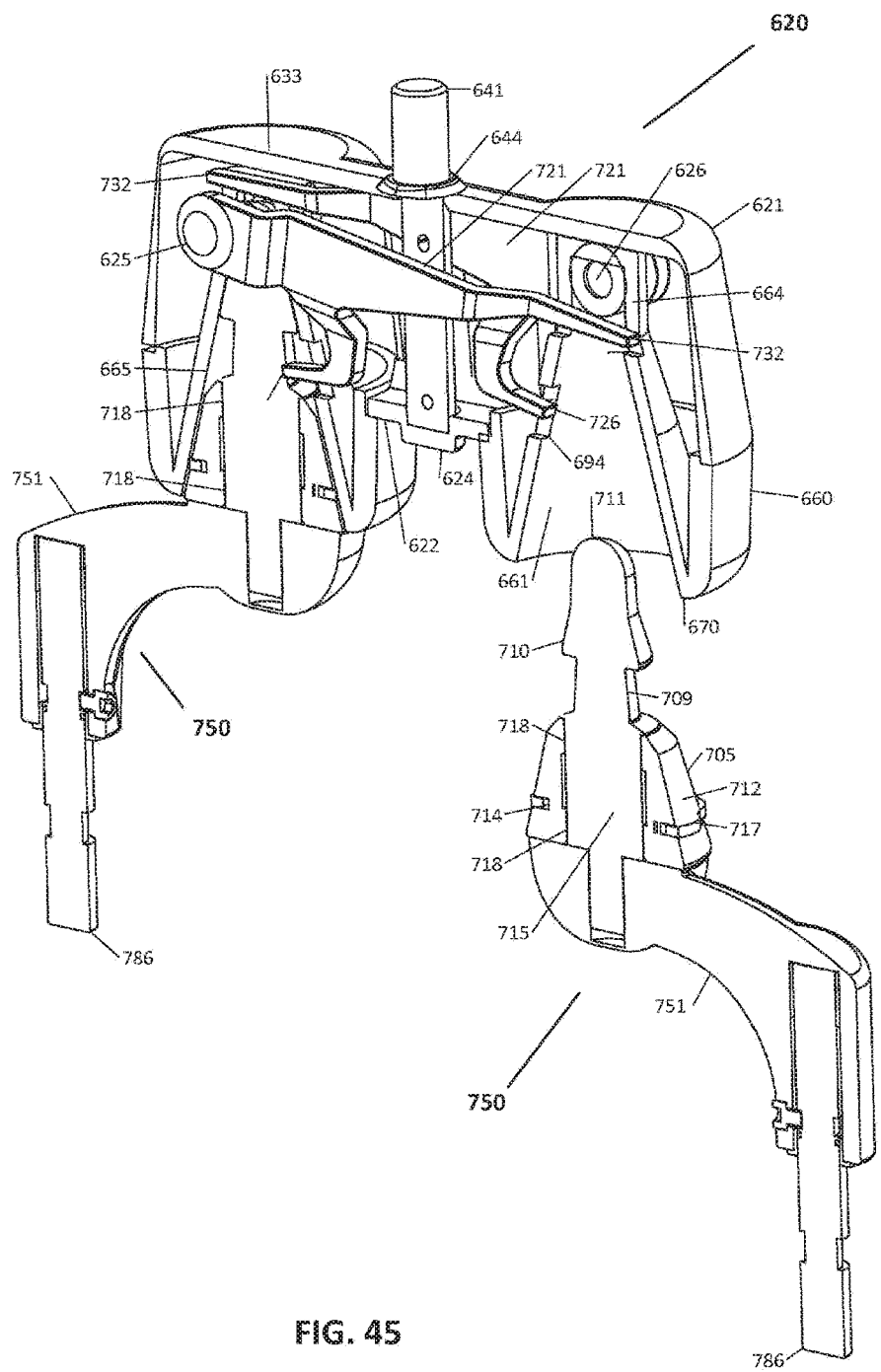
FIG. 45 is a cross sectional view of the transfer device and system.

As shown in FIG. 45, a cone arm 750 is attached to a stationary or mobile support platform. Cone arm 750 comprises arm structure 751, preferably an aluminum casting with, at its proximal end, a shaft 786 and at its distal end a docking cone 700 that is configured for docking engagement with docking cups 660 of transfer device 620. A spine 715 comprises upper cone 710, cone tip 711, inner bearing surface 718, and security engagement notch 709 and is attached to arm structure 751. As described above, the docking cone 700 has a security engagement notch 709 that cooperates with security latch 726 of security lever 721 to prevent or enable retention of docking cone 700, as the case may be, from docking cup 660.

It can also be seen in FIG. 41 that the security lever 721 has an offset 739 therein that creates a spaced apart relation that allows support post 641 to sit in the space created between the security levers 721. As a result, support post 641 can be positioned low in the transfer device 620 to achieve a low overall profile 650 of the transfer device 620 to accommodate attachment of more medical apparatus to the equipment support structure 200.

Turning now to FIG. 45, an alternate arrangement of cone arm 150 and docking cone 100 is shown. Rotation of transfer device 20 about docking cone 100 tends to allow the uncontrolled rotation, or swing-out, of the transfer device during transport. To prevent said swing-out rotation, revolving cone 705 is configured to rotate about spine 715. The inner bearing surface 718 is in contact with spine 715 and may optionally be coated with damping grease to slow and control the rotation of revolving cone 705 relative to spine 715. However, the use of alternative damping means other than grease is within the scope of this specification.

A groove 714 provided in the outer bearing surface 712 of revolving cone 705 is filled with a friction material 717 that extends outwardly to contact inner conical surface 665 of docking cup 660. When transfer device 620 is received onto revolving cone 705, friction material 717 engages the inner conical surface 665 of docking cup 660 to prevent rotation of the transfer device 620 relative to outer bearing surface 712 of revolving cone 705. This engagement transfers the rotation of the transfer device 620 to the rotation-controlled interface between the inner bearing surface 718 and spine 715, thereby effectively controlling rotation and swing-out of the overall transfer device 620.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described.

Figure 46:
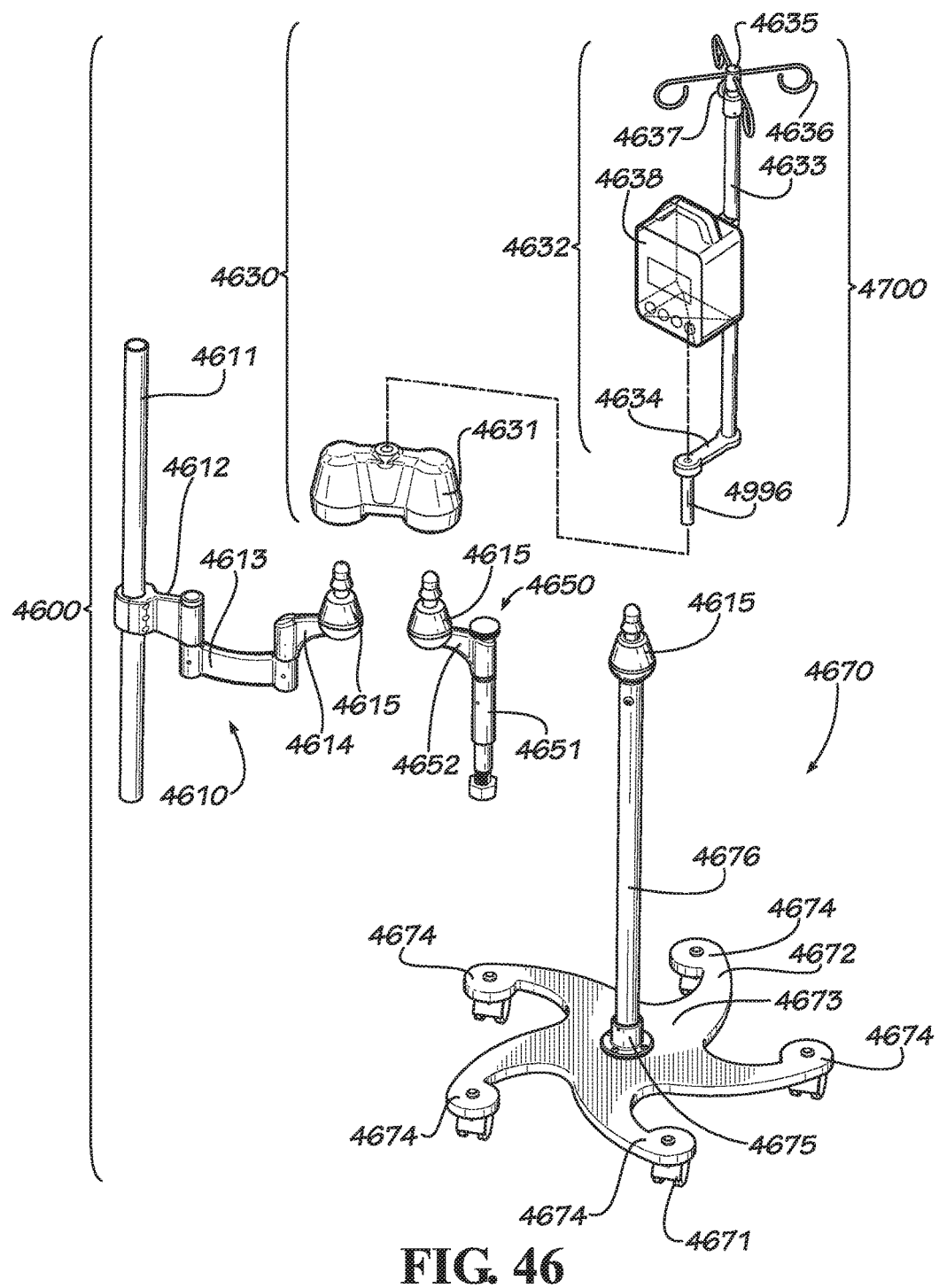
FIG. 46 is a perspective view of several matching components of another embodiment of a transfer system and an embodiment of a portable support platform.

FIGS. 46-70 disclose additional embodiments of transfer systems. FIG. 46 discloses a transfer system 4600, including a transfer apparatus 4630, a stationary support platform 4610, a mobile support platform 4650, and a mobile stand-alone support platform 4670. Various elements of transfer system 4600 are compatible with the disclosed embodiments in FIGS. 1-45. This compatibility makes it possible for the docking cups of previously disclosed transfer devices to receive the cones of the newly support platforms in various embodiments, and for the ability of previously disclosed support platforms to be received by the docking cups of the newly disclosed transfer device in various embodiments.

Transfer apparatus 4630 includes a transfer device 4631 and a patient care apparatus 4632. The patient care apparatus 4632 includes an offset arm 4634 and a pole 4633 that is an IV pole in the current embodiment. The patient care apparatus 4632 also includes a patient care device 4638—shown as an IV pump in the current embodiment. As will be explained in further detail, a center of gravity of the patient care device 4638 is located directly over the shaft 4996 in various embodiments of the patient care apparatus 4632. In various embodiments, the patient care apparatus 4632 includes multiple IV poles, one or more IV infusion pumps, or another type of patient care device mountable either directly or indirectly on the pole 4633 or offset arm 4634 or another portion of the patient care apparatus 4632. In various embodiments, offset arm 4634 includes ball detents (not shown) similar to ball detents 5394 shown in FIG. 53 in order to increase the resistance against rotation of offset arm 4634 or to provide set angular positions at which offset arm 4634 can be "indexed" or rotated in pre-set increments. In various embodiments, the patient care apparatus 4632 includes a top portion 4635 and an adjustment knob 4637 to allow the top portion 4635 to be raised or lowered with respect to the pole 4633. In various embodiments, the top portion 4635 includes hooks 4636. In various embodiments, hooks 4636 can take on any number of different shapes and are not limited to the "rams-horn" style shown. In various embodiments, the quantity of hooks 4636 varies from that shown. In various embodiments, a patient care apparatus kit 4700 includes the patient care apparatus 4632 and a shaft 4996 (shown also in FIG. 49) and can be installed or replaced in the field to change the configuration of the particular patient care apparatus 4632 as desired by the user.

Stationary support platform 4610 includes a mounting pole 4611, a pole link arm 4612, a connecting link arm 4613, and a receiver arm 4614. In various embodiments, mounting pole 4611 is secured to a nearby surface, such as a wall, of the room or other environment in which transfer system 4600 is used and is secured by one or more readily-available brackets (not shown). In various embodiments, the brackets are of an appropriate size, shape, and material to secure mounting pole 4611 and are capable of supporting as much as several hundred pounds or more. In various embodiments, the patient care apparatus 4632 weighs in excess of 100 pounds. In various embodiments, a portion of pole link arm 4612 wraps around a portion of mounting pole 4611 and is held firmly in place by a clamping force provided by a plurality of fasteners 6519 (shown in FIG. 68) that effectively adjust the roughly circular inside diameter of that portion of the pole link arm 4612 that wraps around and is able to adjustably secure the pole link arm 4612 to the mounting pole 4611 at any one of a number of different positions up and down the mounting pole 4611.

As will be describe below in further detail, connecting link arm 4613 is joined to pole link arm 4612 by one or more fasteners that allow connecting link arm 4613 to rotate with respect to pole link arm 4612. Receiver arm 4614 is joined to connecting link arm 4613 by one or more fasteners that allow receiver arm 4614 to rotate with respect to connecting link arm 4613. In various embodiments, the aforementioned connections between the mounting pole 4611 and the pole link arm 4612, between the pole link arm 4612 and the connecting link arm 4613, and between the receiver arm 4614 and the connecting link arm 4613 allow a user to articulately move a receiver 4615 to any one of an infinite number of positions within a radius defined by the combined length of the pole link arm 4612, the connecting link arm 4613, and the receiver arm 4614. In various embodiments, receiver arm 4614 includes the receiver 4615. In various embodiments, the receiver 4615 is frustoconical in shape and may be also described as a cone.

Figure 67:
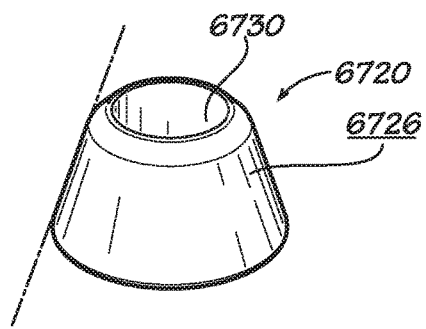
FIG. 67 is a perspective view of an angled cone insert of a receiver of the transfer system of FIG. 49.

The mobile support platform 4650 of FIG. 46 includes a receiver arm 4652 and a mobile support adapter 4651. In various embodiments, receiver arm 4652 includes a receiver 4615. In various embodiments, receiver 4615 can be incorporated into any one or more components of transfer system 4600 including, but not limited to stationary support platform 4610, mobile support platform 4650, and mobile stand-alone support platform 4670. In various embodiments, the receiver 4615 is frustoconical in shape and may be described as a cone. The frustoconical shape of receiver 4615 in the current embodiments is shown with angled side surface 4942' (shown and identified in FIG. 59) in the current embodiment of mobile stand-alone support platform 4670 such that the angled side surface 4942' is substantially flat in cross-section. As discussed below, various embodiments of the docking cone will include substantially scalloped or concave exterior side surfaces (as shown in FIG. 67).

In various embodiments, mobile support platform 4650 is configured to attach to or mount on a mobile platform such as a patient bed, gurney, wheelchair, ambulance, helicopter or other mobile platform between locations within or between medical facilities, such as intensive care rooms, operating rooms, radiology and other imaging facilities, catheterization labs, or between buildings and hospitals. Any mobile platform that includes a frame of sufficient strength and rigidity can be utilized. In various embodiments making use of a hospital bed 410, the mobile support platform 4650 is configured to attach to a frame of the hospital bed 410 via attachment of the lower end of mobile support platform 4650 to a portion of the frame of hospital bed 410.

The mobile stand-alone support platform 4670 of FIG. 46 is substitutable with stationary support platform 4610 or mobile support platform 4650 in various embodiments including medical environments where a stationary support platform or mobile support platform does not exist or is otherwise not available. Mobile stand-alone support platform 4670 includes a base 4672 and a support pole 4676 mounted to the base 4672 with a pole base 4675. Base 4672 includes central portion 4673 and a plurality of legs 4674— specifically five legs 4674 in the current embodiment although any number of legs 4674 may be present in various embodiments and the disclosure of five legs 4674 should not be considering limiting on the current disclosure. Attached to each leg 4674 with a fastener is a leg support 4671. In various embodiments, the leg support is a leg or a caster. In various embodiments, the leg support may incorporate the fastener or the fastening elements of the fastener such as the internal or external threads. The fastener may also take the form of one or more weldments or an adhesive. The presence of leg supports 4671 allows the mobile stand-alone support platform 4670 to be transported to and between those aforementioned environments where a stationary or mobile support platform does not exist or is otherwise not available. Once positioned, however, the mobile stand-alone support platform 4670 effectively becomes stationary by locking the leg supports 4671. In various embodiments, the locking feature is integral with the leg support although the disclosure of a locking feature that is integral with the leg support should not be considered limiting. Extending from base 4672 is the support pole 4676. The support pole 4676 includes a receiver 4615 at the top that in various embodiments is aligned axially with the support pole 4676. In various embodiments, no leg supports are required and base 4672 will sit flat on a horizontal surface such as a floor.

In various embodiments, the receiver—described in some embodiments as a docking cone—includes rotation-dampening features designed to lock or hinder the rotation of transfer apparatus 4630 with respect to receiver 4615 so as to prevent undesirable movement or rotation of transfer apparatus 4630 during movement of any of the support platforms 4650,4670, including in situations that require hospital bed 410, the mobile stand-alone support platform 4670, or another mobile platform to be moved. For example, in various embodiments the rotation-dampening feature prevents the transfer apparatus 4630 from swinging freely during movement of a hospital bed 410 as it is pushed down hospital hallways or around corners.

FIGS. 47-48 disclose mobile support platform 4650. FIG. 47 shows mobile support platform 4650 in assembled form. In various embodiments as previously described, mobile support platform 4650 includes a mobile support adapter 4651 and a receiver arm 4652. Mobile support adapter 4651 includes an adapter shaft 4710 and an adapter fastener 4720. Receiver arm 4652 includes an arm portion 4840, a receiver 4615, and an arm brake mechanism 4730. In various embodiments, arm brake mechanism 4730 includes a brake fastener 4860. FIG. 48 shows an exploded view of mobile support platform 4650. Adapter shaft 4710 of mobile support adapter 4651 includes an upper portion 4811 and a lower portion 4812. In various embodiments, upper portion 4811 defines an edge treatment 4817 and a bore 4816. In various embodiments, lower portion 4812 of mobile support adaptor 4651 includes an attachment portion 4813 incorporating a threaded portion 4814 and defining a cut 4815. In various embodiments, bore 4816 of mobile support adaptor 4651 is sized to receive lower portion 4823 of brake shaft 4820. In various embodiments, lower portion 4823 of brake shaft 4820 is restricted from rotating or translating with respect to mobile support adaptor 4651 by use of a fastener such as a set screw for coupling brake shaft 4820 to mobile support adaptor 4651.

In various embodiments, attachment portion 4813 including threaded portion 4814 and cut 4815 are designed to mount on any one of a number of areas of the frame of a hospital bed 410 or any of a number of other aforementioned pieces of furniture or equipment. In various embodiments, nut 4720 secures mobile support adaptor 4651 to the equipment to which it is mounted after attachment portion 4813 has been inserted through a mounting hole (not shown) on such equipment. In various embodiments, an additional adaptor is utilized to connect mobile support adaptor 4651 to such equipment.

In addition to brake fastener 4860, arm brake mechanism 4730 includes a brake shaft 4820, a washer 4830, a pair of fasteners 4835*a,b*, and a brake spacer 4850. In various embodiments, fasteners 4834*a,b* are pins. In various other embodiments, one or more of fastener 4834 is any one of a group of fasteners including, but not limited to, a key or squared shaft. In various embodiments, the arm brake mechanism 4730 works in concert with the arm portion 4840 to prevent the rotation of or resist the rotation of receiver arm 4652 about mobile support adapter 4651. In various embodiments, brake shaft 4820 includes an upper portion 4821, a flange portion 4822, and a lower portion 4823. In various embodiments, brake shaft 4820 defines a bore 4824 and a pair of fastener bores 4825*a,b*. In various embodiments, bore 4824 includes threads matching a threaded portion 4862 of brake fastener 4860. In various embodiments, fasteners bores 4825*a,b* are sized to receive fasteners 4834*a,b*. In various embodiments, each of fastener bores 4825*a,b* is a straight-sided hole sized to fit fasteners 4835*a, b*, respectively, and defined in and extending axially into upper portion 4821 of brake shaft 4820, far enough to fit at least a portion of the length of fasteners 4835*a,b*. In various embodiments, one or more of fastener 4834 is integrally formed as part of brake shaft 4820 where one or more of fastener bore 4824 would otherwise be located. In various embodiments, one or more of fastener 4834 is integrally formed as part of brake spacer 4850 where one or more of a plurality of fastener bores 6010*a,b* (shown in FIG. 60) of brake spacer 4850 would otherwise be located.

In various embodiments, brake fastener 4860 includes not only the threaded portion 4862 but also a fastener head 4865. In various embodiments, the fastener head 4865 includes a textured grip 5930. In various embodiments, the textured grip 5930 includes a knurled pattern. In various embodiments, the textured grip 5930 includes features that facilitate a grip on the fastener head 4865 for loosening and tightening the brake fastener 4860 with a reduced force. In various embodiments, the fastener head 4865 has a diameter as much as five to ten times a diameter of the threaded portion 4862 of the brake fastener 4860 for increased leverage—by an increase in a distance from the center of rotation at which the force is acting—and therefore less force is required to tighten the brake fastener 4860 to achieve the same tightening torque, though other diameter ranges may be present in various other embodiments. In various embodiments, the fastener head 4865—including the textured grip 5930—has a liquid-shedding and easily-cleanable design. In various embodiments, the fastener head 4865 is formed from a group of durable materials including, but not limited to, plastics, rubbers, and metals. In various embodiments, the fastener head 4865 is formed around threaded portion 4862 such that the one cannot rotate with respect to the other. In various embodiments, the fastener head 4865 is a knob.

In various embodiments, brake fastener 4860 includes a fastener head 4865 that includes a lever portion extending from threaded portion 4862 and a cam device where threaded portion 4862 and fastener head 4865 intersect. Like a quick-release lever on a wheel of a higher-end bicycle, the incorporation of the cam device effectively shortens the exposed length of the threaded portion 4862 when the lever portion is bent from a non-locking position to a locking position. Shortening the exposed length threaded portion 4862 effectively engages the arm brake without rotating threaded portion 4862. A user who rotates threaded portion 4862 about an axial center of threaded portion 4862, a step that can be desirable but it not required, simply adjusts the clamping force that is achieved once the lever portion is engaged. In various embodiments, the mechanical advantage created by the lever portion reduces the force (or torque in the case of a rotating fastener) required at the point of final engagement of brake fastener 4860—and arm brake mechanism 4730 by extension—which can be of benefit to users whose strength may be limited. In various embodiments, the use of a lever allows speedy and predictable tight engagement of the arm brake mechanism 4730.

Figure 49:
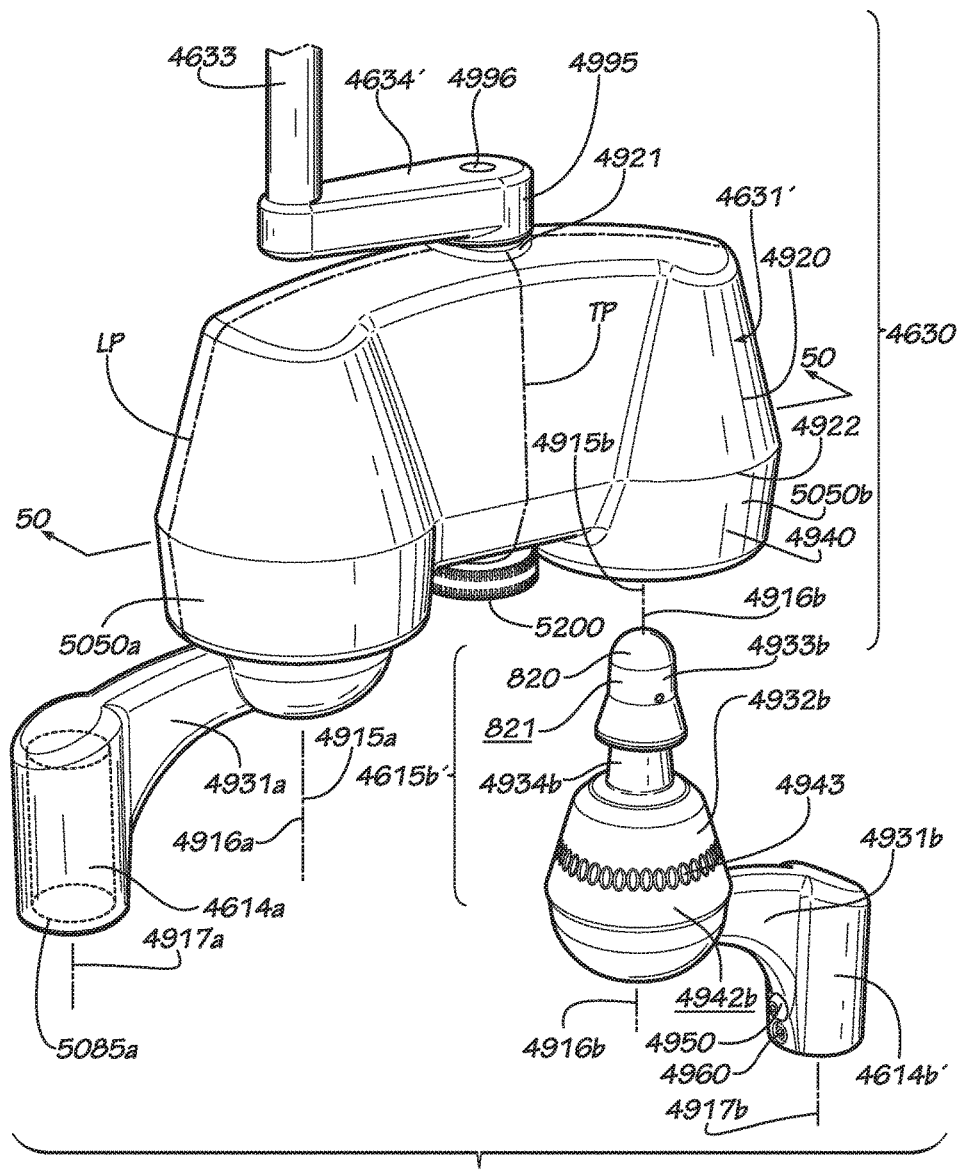
FIG. 49 is a perspective view of another embodiment of a transfer system including a transfer apparatus, a first receiver arm, and a second receiver arm.

As disclosed in FIG. 49, the transfer system 4600 includes, at least in part, the transfer apparatus 4630, a first receiver arm 4614a, and a second receiver arm 4614b. In various embodiments, the transfer apparatus 4630 includes the transfer device 4631', an offset arm 4634', and the patient care apparatus 4632 including, in various embodiments, the pole 4633. In various embodiments, the transfer device 4631' includes an upper housing 4920, a lower housing 4940, a support shaft 4996—also known as a support post—received therebetween, and a shaft brake mechanism 5200. In various embodiments, transfer device 4631' includes a security mechanism 5010. In various embodiments, transfer device 4631' is substantially symmetrical about a transverse plane of symmetry TP and substantially symmetrical about a longitudinal plane of symmetry LP with support shaft 4996 at the intersection of the transverse plane of symmetry TP and the longitudinal plane of symmetry LP. In various embodiments, the lower housing 4940 is received in the upper housing 4920 by a lip 5720 (shown in FIG. 57) at a joint line 4922. Support shaft 4996 is received in a bottom guide 5861 (shown in FIG. 58) of lower housing 4940 and in an upper guide 5750 (shown in FIG. 57) in the upper housing 4920. Support shaft 4996 protrudes from a shoulder 4921 of upper housing 4920 to engage a hub 4995 of offset arm 4634'. As shown in the portion of an embodiment of transfer device 4631' shown in FIG. 52, hub 4995 of offset arm 4634' does not include the ball detents described as being in at least some embodiments of offset arm 4634. In various embodiments, offset arm 4634' rotates with respect to transfer device 4631'.

Each receiver arm 4614a,b is attached to a support platform such as the stationary support platform 4610, mobile support platform 4650, or mobile stand-alone support platform 4670. In various embodiments, a fastener 4950 secures a bushing (not shown) inside a bore 5085 of receiver arm 4614 so that receiver arm 4614 will rotate smoothly about that portion of transfer system 4600 about which receiver arm 4614 rotates without dislodging or causing the bushing to rotate with respect to receiver arm 4614. In various embodiments, the bushing is formed from any one of a number of materials including, but not limited to metals, plastics, or composites. In various embodiments where it is desired that receiver arm 4614 not rotate with respect to that portion of transfer system 4600 on which receiver arm 4614 is mounted (for example, a shaft similar to a hinge pin 6580 to which a receiver arm 4614" is secured as in the stationary support platform 4610' of FIG. 68), a fastener 4960 secures the receiver arm 4614 to the mount (not shown).

Receiver arms 4614a,b include receivers 4615a',b' (4615a' shown in FIG. 50) and arm portions 4931a,b, respectively. At a distal end of each of arm portions 4931a,b is a receiver 4615a',b' that is configured for docking engagement with either of a pair of docking cups 5050a,b of transfer device 4631' of transfer apparatus 4630. Each of receivers 4615a',b' includes a spine 815 (shown in FIG. 50), one of a lower portion 4932a,b, respectively (4932a shown in FIG. 50), and one of an upper portion 4933a,b, respectively (4933a shown in FIG. 50). In various embodiments, each of upper portions 4933a,b includes a dome 820 and a guide surface 821. In various embodiments, lower portions 4932a,b define angled side surfaces 4942a,b, respectively. In various embodiments, angled side surfaces 4942a,b each define relief 4943 or a plurality of reliefs 4943. In various embodiments, spine 815 defines an undercut section defined as security engagement notch 4934a,b on each of receivers 4615a',b'. Each security engagement notch 4934 cooperates with a cone feeler 5068a,b of one of a pair of security levers 5065a,b, respectively, of the security mechanism 5010 to facilitate retention of receiver 4615a',b' in docking cups 5050a,b under certain conditions described herein. In various embodiments, receivers 4615a',b' are radially symmetrical about receiver axes 4916a,b, respectively, and docking cups 5050a,b are substantially radially symmetrical about docking cup axes 4915a,b, respectively.

In various embodiments, a receiver 4615 includes any structure receivable by docking cup 5050. In various embodiments, a receiver 4615 includes any structure receivable by docking cup 5050 where the receiver includes a security engagement notch 4634. In various embodiments, a receiver 4615 includes any structure receivable by docking cup 5050 where the receiver includes a security engagement notch 4634 and a dome 820 capable of engaging cone feeler 5068 of security lever 5065 of security mechanism 5010.

Figure 50:
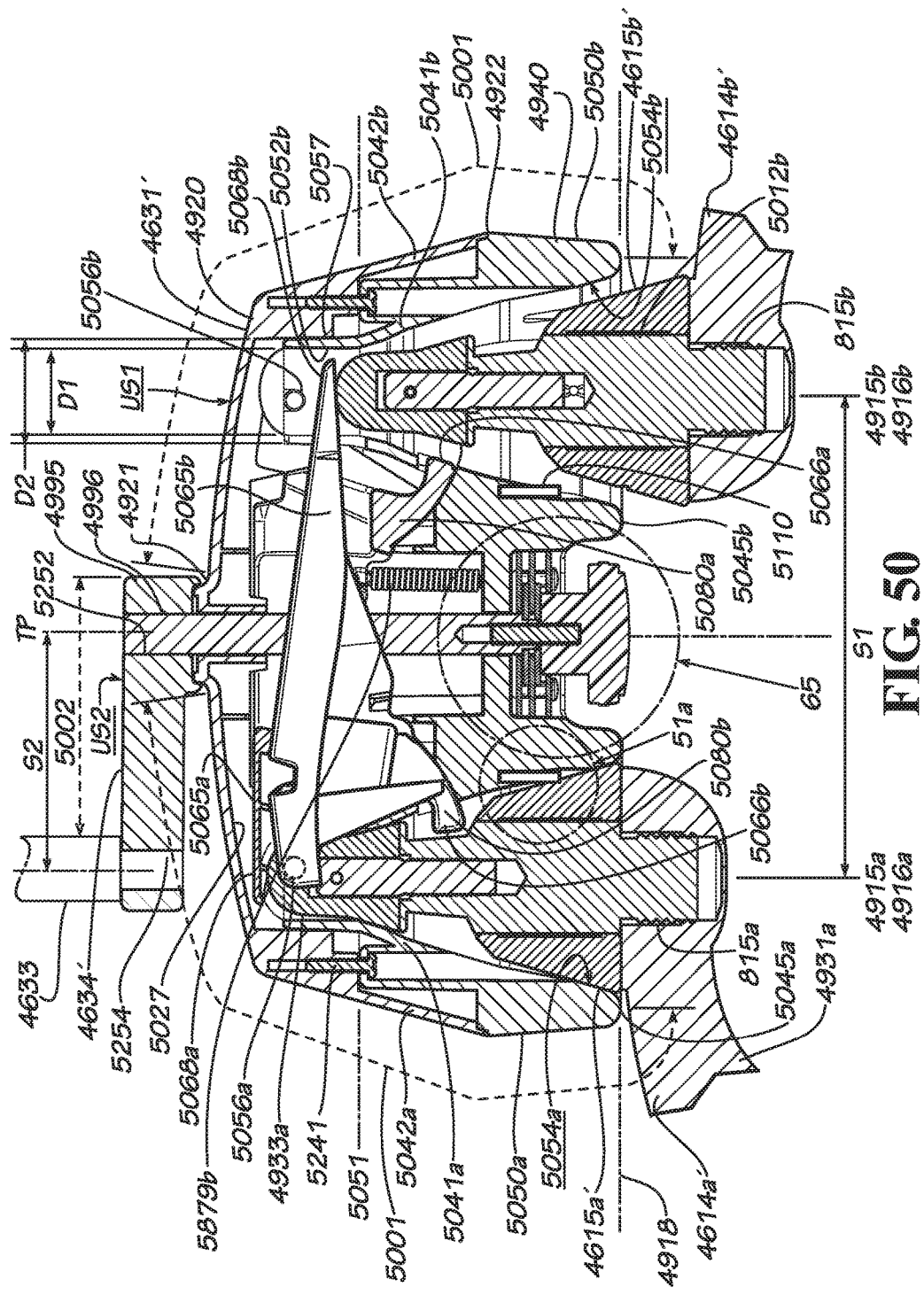
FIG. 50 is a sectional view of the transfer system of FIG. 49 taken along line 50-50 of FIG. 49.

FIG. 50 discloses a sectional view of a portion of the transfer system 4600 including transfer apparatus 4630 and receivers 4614a',b', transfer apparatus 4630 again including transfer device 4631. In various embodiments, each of arm portions 4931a,b is formed as an aluminum casting with a bore 5085 (shown in FIG. 49) aligned axially with arm axis 4917a or arm axis 4917b, respectively. Aluminum, for purposes of this disclosure, includes any one of a number of alloys containing aluminum. The disclosure of an aluminum casting, however, should not be considering limiting. In various other embodiments, a material other than aluminum or an aluminum alloy including plastics and other metals is used to form at least part of arm portions 4931a,b and one or more other components of transfer system 4600.

As previously described in regard to other embodiments, docking cups 5050a,b are substantially identical and generally symmetrical conical hollow structures defining inner surfaces 5054a,b, respectively. In various embodiments, inner surfaces 5054a,b may each also be described as a conical cavity. In various embodiments, docking cup 5050 includes an elongated extension 5057—extending upward from a neck plane 5051—to receive the upper portion 4933 of receiver 4615' in coaxial alignment as more fully described below. A bottom opening defining a deflection edge 5045 of each docking cup 5050 faces downward and is positioned such that each docking cup 5050 is open to the outside for insertion of receiver 4615' without exposing the security mechanism 5010.

The deflection edge 5045 at the bottom opening of docking cup 5050 is shaped to deflect misaligned insertion of dome 820 of upper portion 4933 of receiver 4615'. Because the deflection edge 5045 has a rounded shape, a misaligned dome 820 of receiver 4615' will deflect towards the inside of the docking cup 5050 or will deflect away from transfer device 4631' if significantly misaligned. In various embodiments, the shape of deflection edge 5045 is asymmetric such that dome 820 of receiver 4615' will be deflected into docking cup 5050 as long as the tip of the receiver in contact with transfer device is inboard from a radially-outermost exterior surface of docking cup 5050. In various embodiments, each docking cup 5050 includes a security aperture 5849 (shown in FIG. 58), which permits passage of a latch tip 5066 of a security latch 5080. In various embodiments, each docking cup 5050 includes a feeler notch 5848 (also shown in FIG. 58), which permits the cone feeler 5068 of security lever 5065 to drop down into throat 5057 of docking cup 5050—as far as to the bottom of feeler notch 5848 in various embodiments—when no receiver is docked so that the security latch 5080 engages the receiver 4615' docked inside the neighboring docking cup 5050, thereby preventing the removal of receiver 4615' until security latch 5080 is no longer engaged. In various embodiments, each docking cup 5050 includes an inner wall 5041 and an outer wall 5042. Extension 5057 of each docking cup 5050 also includes a throat 5550 (shown in FIG. 55), which includes a throat inner surface 5052 defining a throat clearance diameter D1 at neck plane 5051. An upper end of the outside of extension 5057 defines an outside diameter D2.

In various embodiments, upper housing 4920 is attached to lower housing 4940 with a plurality of fasteners 5241. In various embodiments, fastener 5241 will be a non-magnetic, stainless steel thread-forming screw including a triangular (or tri-lobular) shank to ensure a vibration-resistant connection in plastic, though the screw may be other materials in various embodiments. This type of screw is also known as a PLASTITE screw, described as having "coarse, sharply angled threads and a blunt tip." See, e.g., Item 96001A326 available from McMaster-Carr Supply Company. The aforementioned catalog describes the screw as providing "maximum holding strength with minimal stress in formable plastics such as polypropylene and polycarbonate." In various embodiments, the head of fastener 5241 will include a TORX recess in order to increase the tamper resistance of transfer apparatus 4630 and specifically transfer device 4631' by requiring a special tool for disassembly. However, the disclosure of a stainless-steel tri-lobular screw with a TORX head should not be considered limiting. In various embodiments, the upper housing 4920 and lower housing 4940 can be connected using one of a group of other attachment methods including, but not limited to, other threaded or non-threaded fasteners, weldments, plastic snap joints, and adhesives.

Docking cup axes 4915a and 4915b of docking cups 5050a and 5050b, respectively, are spaced apart horizontally by cup axis spacing S1. In various embodiments, cup axis spacing S1 is a distance equal to between two and two-and-a-half multiples of an outer diameter of docking cup 5050. In various embodiments, an offset arm spacing S2 is defined as the distance between a center of a hole 5090 and a center of a hole 5095 in offset arm 4634'. In various embodiments, the offset arm spacing S2 is equal to a distance between a center of support shaft 4996 and a center of pole 4633. In various embodiments, offset arm spacing S2 is substantially equal to one half of cup axis spacing S1 in order to bring pole 4633 of the patient care apparatus 4632 directly over the receiver 4615' at least when offset arm 4634' is so oriented along the longitudinal plane of symmetry LP. In various embodiments, the offset arm spacing S2 is such that a center of gravity (not shown) of the patient care apparatus 4632 lies directly over the support shaft 4996. In various embodiments, the offset arm spacing S2 measures between one half inch and ten inches. In various other embodiments, the offset arm spacing S2 measures outside this range. In various embodiments, offset arm spacing S2 is greater than or less than one half of cup axis spacing S1.

Transfer device 4631' defines an exposed upper exterior surface US1 along lines 5001 around the transfer device 4631' (although not only in the plane where lines 5001 are shown). The offset arm 4634' defines an exposed upper exterior surface US2 in the area shown by line 5002 (although not only in the plane where line 5002 is shown). The receiver arms 4614a,b define an exposed upper exterior surface US3 (shown in FIG. 59) along lines 5003 (although not only in the plane where lines 5003 are shown), and each of the other components separately define an exposed upper exterior surface (not shown). In various embodiments, one or more of the exposed upper exterior surfaces US1, US2, US3 (and other exposed upper exterior surfaces of the transfer system 4600 or the components thereof) are vertical or sloped outward so that no horizontal surfaces exist that can retain or trap a liquid—possible at least due to the surface tension of the liquid—and become a source of increased infection or contamination risk.

Further, docking cup 5050 defines a pivot slot 5056 that allows security lever 5065 to pivot about a pair of pivot pins 5475 upon movement of cone feeler 5068 away from docking cup 5050 and towards interior top cavity 5027 defined in upper housing 4920. Each security lever 5065 of security mechanism 5010 includes the security latch 5080 with the latch tip 5066 that pivots from a first secured position (e.g., the position of security latch 5080b of security lever 5065b in FIG. 50) to a second released position (e.g., the position of security latch 5080a of security lever 5065a in FIG. 50). The movement of security latch 5080 brings latch tip 5066 into and out of engagement with security engagement notch 4934 of receiver 4615' to control retention of receiver 4615' in the respective docking cup 5050 of transfer device 4631'. The cone feeler 5068 of each security lever 5065 causes the security latch 5080 of said security lever 5065 to pivot from a first secured position to a second released position in response to being displaced upward by the cone tip 711 of docking cone 700. In various embodiments, security lever 5065 is displaced upward against the bias of biasing element 5579 (shown in FIG. 55) or the bias of biasing element 5879 (shown in FIG. 58). In various embodiments, a biasing element is incorporated into security lever 5065. In various embodiments such as shown in a security lever 5065' of FIG. 54d, a biasing element is integrally formed with security lever 5065,5065'.

In various embodiments, the security mechanism 5010 is enclosed within the transfer device 4631'. In various embodiments, the security mechanism 5010 includes a first security lever 5065a and a second security lever 5065b, the first security lever 5065a positioned to disengage a first receiver 4615a' in the first docking cup 5050a when a second receiver 4615b' is received within the second docking cup 5050b, and the second security lever 5065b positioned to disengage the second receiver 4615b' in the second docking cup 5050b when the first receiver 4615a' is received within the first docking cup 5050a. In various embodiments, the security levers 5065a,b default to a position where the cone feelers 5068a,b, respectively, drop to the lowest position when no docking cone or receiver 4615' is inserted into the transfer device. In various embodiments, the default position is ensured by the presence of a biasing element such as biasing element 5579 (shown in FIG. 55) or biasing element 5879 (shown in FIG. 58) engaging each security lever 5065 so as to bias the cone feelers 5068*a,b* in the downward direction. In various embodiments, the default position is ensured by the force of gravity, by a magnetic force, or by another force acting on each of security levers 5065*a,b*.

In various embodiments, each docking cup 5050 includes a plurality of rotation-dampening elements 5110 for use in restraining or restricting or dampening the rotational movement of transfer device 4631' with respect to receiver 4615'. Rotation of transfer apparatus 4630 about receiver arm 4614 tends to allow the uncontrolled rotation, or swing-out, of the transfer apparatus 4630 during transport. In various other embodiments, no such element or only one such rotation-dampening element 5110 exists. In various embodiments, each of rotation-dampening elements 5110 has a flattened end.

Figures 51A, 51B:
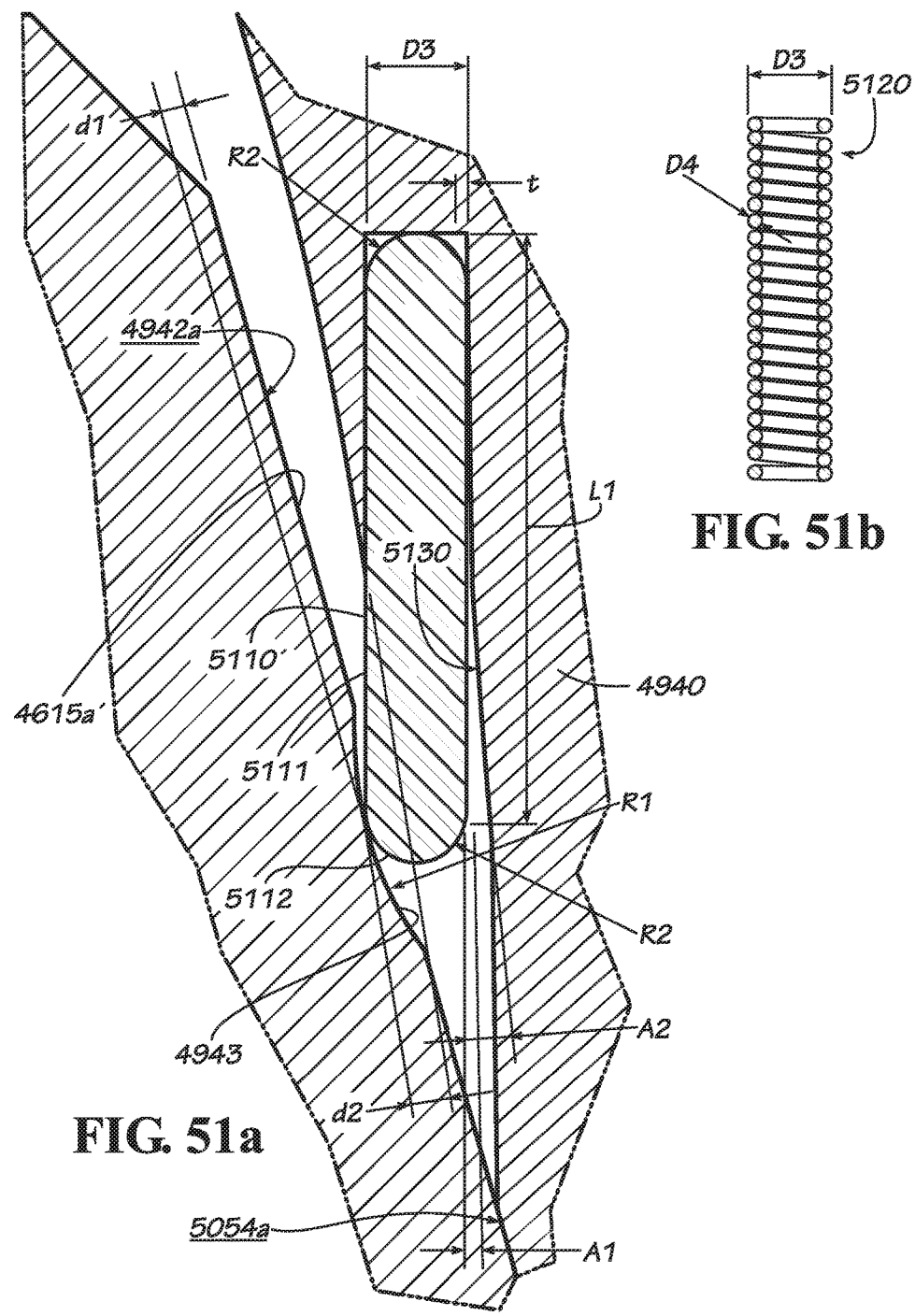
FIG. 51a is a detail sectional view of the transfer device of the transfer system of FIG. 49 taken from detail 51a of FIG. 50 showing one embodiment of a rotation-dampening element assembled to a docking cup of the transfer device.
FIG. 51b is a sectional view of another embodiment of a rotation-dampening element adapted for assembly to a docking cup of the transfer device in FIG. 49.

FIG. 51*a* shows a detail view of a rotation-dampening element 5110' assembled in a bore 5130 of docking cup 5050*a* of lower housing 4940 and engaged with relief 4943 defined in angled side surface 4942*a* so as to prevent or resist the rotational movement of transfer device 4631' with respect to receiver 4615'. In various embodiments and in conditions where rotation is not desired, the torque required to rotate transfer device 4631' about cup axis 4915 will not be sufficient to deform rotation-dampening element 5110' towards a radially outer surface of bore 5130 enough for an outer wall 5111 of rotation-dampening element 5110' to clear relief 4943. In various embodiments, rotation-dampening element 5110,5110' is a tube or is tube-shaped and made from vinyl, silicone, or similar flexible material. FIG. 51*b* discloses a rotation-dampening element 5120 formed as a coil spring. In various embodiments, an angled side surface 4942 of the receiver 4615' defines a relief 4943 and one or more rotation-dampening elements 5120,5110,5110' extends radially inward from the inner surface 5054 of the docking cup 5050. In various embodiments, one or more of rotation-dampening elements 5120,5110,5110' are replaceable if found to be worn after extended use. In various embodiments, one or more of rotation-dampening elements 5120, 5110,5110' are substitutable with a rotation-dampening elements 5120,5110,5110' having a different shape to increase the desired dampening effect.

Any one or more of the following specifications of the rotation-dampening element(s) 5120, 5110,5110' can be adjusted to increase the dampening effect:

1. Material
2. Quantity
3. Spacing
4. Relief depth d1 (measured from angled side surface 4942)
5. Longitudinal radius R1
6. Latitudinal radius as measured in a horizontal plane (not shown)
7. Protruding distance d2
8. Diameter D3
9. Length L1
10. Shape of edge 5112 (including size of tip radius R2 in some embodiments)
11. Material of docking cup inner surface 5054
12. Wall thickness t
13. Wire diameter D4
14. Angles A1 and A2

The above list is not an exhaustive list of the various methods for adjusting the dampening effect of the rotation-dampening elements. Additional materials and structures could be used to achieve a similar dampening effect including, but not limited to plastic springs molded into either the wall of docking cup 5050 or receiver 4615' or both or the use of flexible pawls like pawl 6570 shown incorporated into receiver 4615" in FIG. 68. In various embodiments where the rotation-dampening element is assembled to the inside of the docking cup 5050, crevices in receiver 4615' that could increase the difficulty of cleaning receiver 4615' will be minimized or eliminated.

Figure 51C:
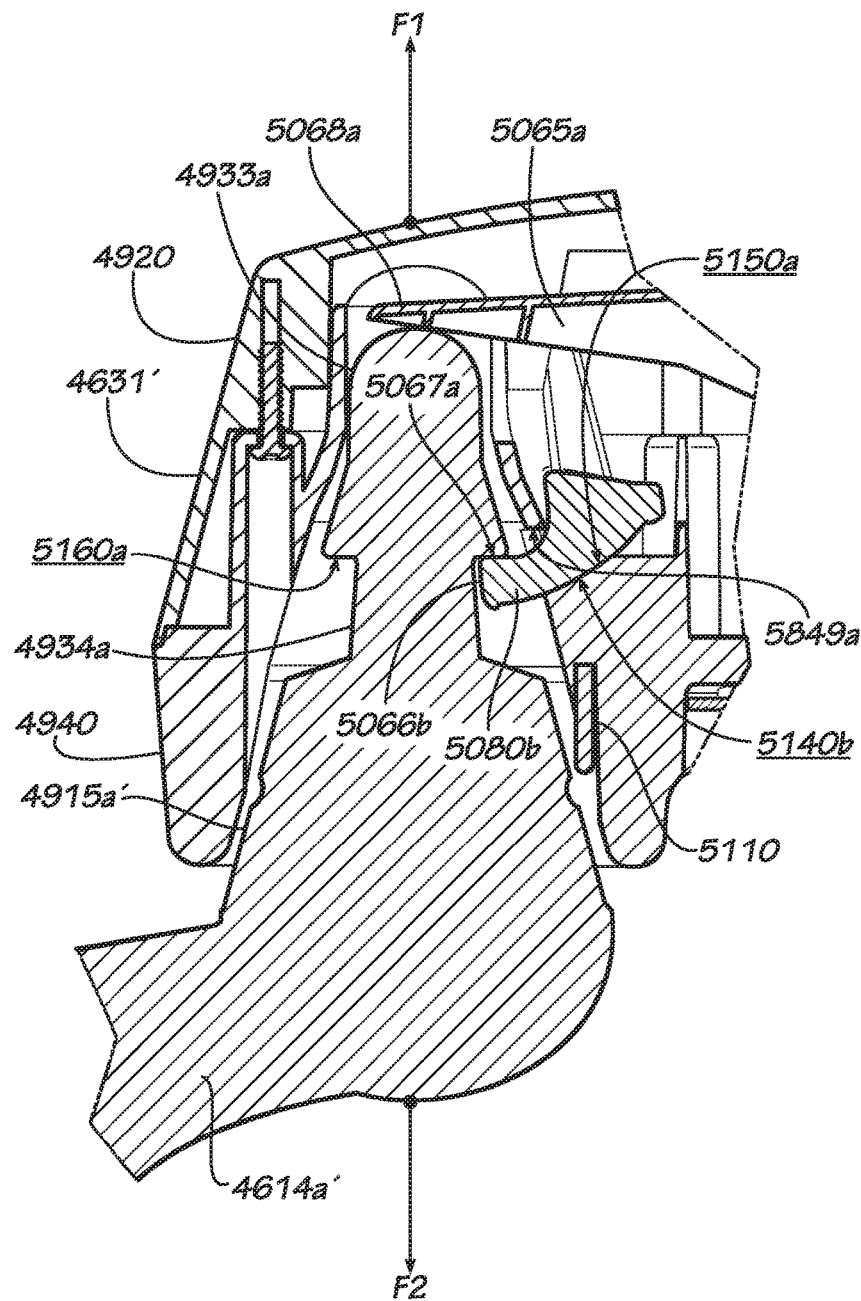
FIG. 51c is a detail sectional view of a portion of the transfer system of FIG. 49 showing the transfer device being lifted while a receiver of the transfer system is locked into a docking cup of the transfer device.

FIG. 51*c* discloses a partial sectional view of the transfer device 4631' of the transfer apparatus 4630 of FIG. 49 showing the transfer device 4631' being lifted with an upward-acting force F1. Simultaneously, downward-acting force F2 is acting on receiver 4615*a'* of the transfer system 4600, receiver 4615*a'* being locked into a docking cup 5050 of the transfer device 4631. In various embodiments, force F2 will result from the weight of the structure to which receiver 4615*a'* is part. In various embodiments, force F2 will be a resultant force resulting from the secure attachment of receiver 4615*a'* to a physical structure such as the wall, floor, or ceiling of a room.

In various embodiments, the transfer device 4631' including security mechanism 5010 can support the load applied when someone or something uses the transfer device 4631' to lift up at least some of the weight of the hospital bed 410 or other movable structure to which receiver arm 4614*a'* is attached. In various circumstances, someone or something lifts up the transfer device 4631' while security latch 5080*b* is engaged with security engagement notch 4934*a* of receiver 4615*a'* thereby preventing removal of receiver 4615*a'* from transfer device 4631'. In various circumstances, security latch 5080*b* is engaged with security engagement notch 4934*a* of receiver 4615*a'* specifically when locking receiver 4615*a'* is locked into docking cone 5050*a* but receiver 4615*b'* is not locked into docking cone 5050*b*. In such circumstances, security latch 5080*b* will bear some or all of the weight of the hospital bed 410 or other movable structure to which receiver 4615' is attached. At such times, a lower surface 5140*b* of the security latch 5080 contacts a lower edge surface 5150*a* of security aperture 5849*a* and an upper edge 5067*a* of the security latch 5080 contacts a lower edge surface 5160*a* of upper portion 4933*a* of receiver 4615' of receiver arm 4614 such that the transfer device 4631 supports the load represented by the force F2'. In various embodiments, each security lever 5065 will be shaped in such a way and made of such a material having sufficient strength to support the shear load that will act on security lever 5065 and particularly security latch 5080 in such circumstances as described.

In various embodiments, the security lever 5065 defines a curvature of the lower surface 5140 having a radius R3 (shown in FIG. 54*d*) which may be slightly smaller than but which substantially complements a radius (not shown) of the lower edge surface 5150 of the security aperture 5849 of the lower housing 4940 of the transfer device 4631'. In various embodiments, the lower surface 5140 and the lower edge surface 5150 are thus in a co-radial relationship. In normal operation of the transfer system 4600, a small gap exists between the lower surface 5140 of the security latch 5080 and the lower edge surface 5150 of the security aperture 5849; in various embodiments, this gap allows for free movement of the security latch 5080 without any encumbrance due to the sliding of lower surface 5140 on the lower edge surface 5150. When loading of the transfer device 4631' causes the security latch 5080 to be pushed towards the lower edge surface 5150, the small gap between the lower surface 5140 and the lower edge surface 5150 closes such that the lower surface 5140 bears against lower edge surface 5150 and is supported thereby in various embodiments. In various embodiments, the use of a glass-reinforced polymer material, metal, or another material for security lever 5065, the use of vertical ribs in security latch 5080 where contact is made with security aperture 5849 and receiver 4615', or both, will successfully support the described load. See FIG. 54c for additional description of the security lever 5065.

Figure 52:
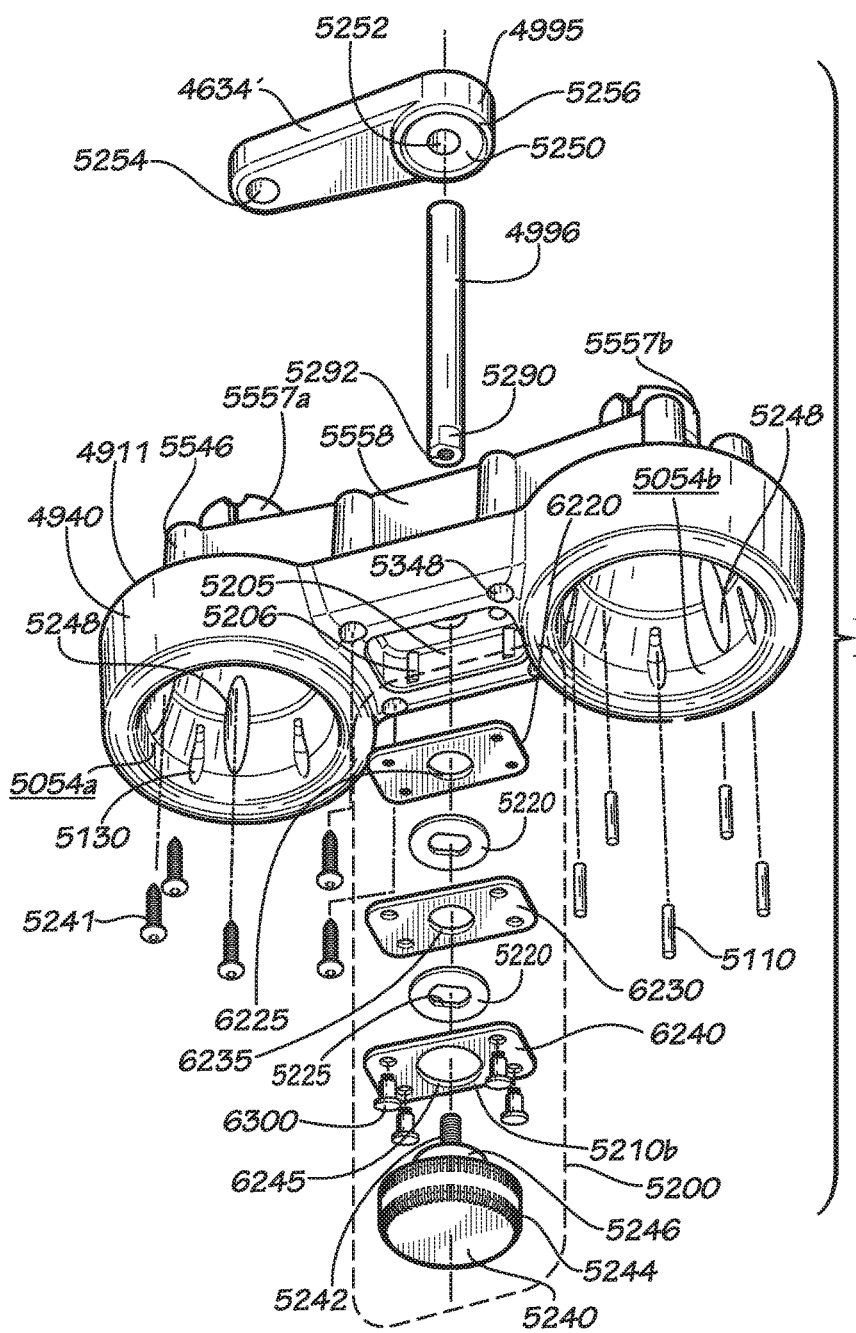
FIG. 52 is an exploded view of the transfer apparatus shown in FIG. 49 with an upper housing, a security mechanism, and the pole removed.

FIG. 52 discloses an exploded view of transfer device 4631 without the upper housing 4920 and the security mechanism 5010 but with the offset arm 4634'. Lower housing 4940 is shown with offset arm 4634', support shaft 4996, fasteners 5241, rotation-dampening elements 5110', and shaft brake mechanism 5200. Offset arm 4634' includes a bore 5252, a bore 5254, and a bearing surface 5250 recessed into hub 4995 to define a lip 5256. In various embodiments, the presence of lip 5256 prevents area between hub 4995 and shoulder 4921 of upper housing 4920 from being soiled. Support shaft 4996 is shown with threaded bore 5292 and flats 5290. The bottom of lower housing 4940 is shown with a rectangular recess 5205, the docking cup inner surfaces 5054a,b, bores 5130, and, a plurality of side protrusions 5206, fastener head bores 5248, and fastener head bores 5348. The top of lower housing 4940 is shown with extensions 5557a,b, a plurality of mounting bosses 5546, and a plurality of reinforcing ribs 5558.

In various embodiments, shaft brake mechanism 5200 includes a combination of any one or more of plates, brake pads, spacers, and brake fasteners. In various embodiments, some of the components of shaft brake mechanism 5200 are assembled to each other to form shaft brake assembly 6200 (shown in FIG. 62) before assembling shaft brake mechanism to transfer device 4631'. In the current embodiment, shaft brake mechanism 5200 includes an upper plate 6220, a middle plate 6230, a lower plate 6240, a pair of brake pads 5220, a plurality of standoff fasteners 6300, and a brake fastener 5240. In various embodiments, upper plate 6220, middle plate 6230, and lower plate 6240 are shown with bores 6225, bore 6235, and bore 6245, respectively. In various embodiments, brake pads 5220 include an anti-rotation cutout 5225. In various embodiments, brake fastener 5240 includes a threaded portion 5242, a knurled portion 5244, and a standoff portion 5246. In various embodiments, the lower housing 4940 is formed with a parting line 4911, although the location of the parting line is not limited to that shown.

When engaged by tightening brake fastener 5240, shaft brake mechanism 5200 fixes the rotational position of support shaft 4996—and by extension the patient care apparatus 4632—by fixing the rotational position of one or more brake pads 5220. Fixing the rotational position of one or more of brake pads 5220 is made possible by coupling each brake pad 5220 to support shaft 4996 by the use of the "double-D" anti-rotation cutout 5225. In various embodiments, anti-rotation cutout 5225 in each of brake pads 5220 matches the cross-sectional shape of support shaft 4996 at the lower end where support shaft 4996 defines a pair of flats 5290. In various embodiments, tightening brake fastener 5240 results in increased pressure between one or more brake pads 5220 and middle plate 6230. Such increased pressure between each of the parts and particularly at the surfaces of each of the brake pads 5220 increases the coefficient of friction and therefore the resistance to rotational movement—of the brake pads 5220 and therefore also the support shaft 4996 to which the brake pads 5220 are coupled.

In various other embodiments, more components or fewer components are present to accomplish the braking function. In various embodiments, brake fastener 5240 includes a lever portion extending from threaded portion 5242 and a cam portion proximate to the intersection between threaded portion 5242 and the lever portion. Bending the lever effectively translates the threaded portion 5242 without rotating threaded portion 5242. In various embodiments, the mechanical advantage created by the lever portion reduces the force (or torque in the case of a rotating fastener) required at the point of final engagement-which can be of benefit to users whose strength may be limited—and allows speedier, if not instant, engagement of the shaft brake mechanism 5200. In various embodiments, the structure and function is similar to that of the aforementioned bicycle wheel quick-release lever.

Figures 53, 54A:
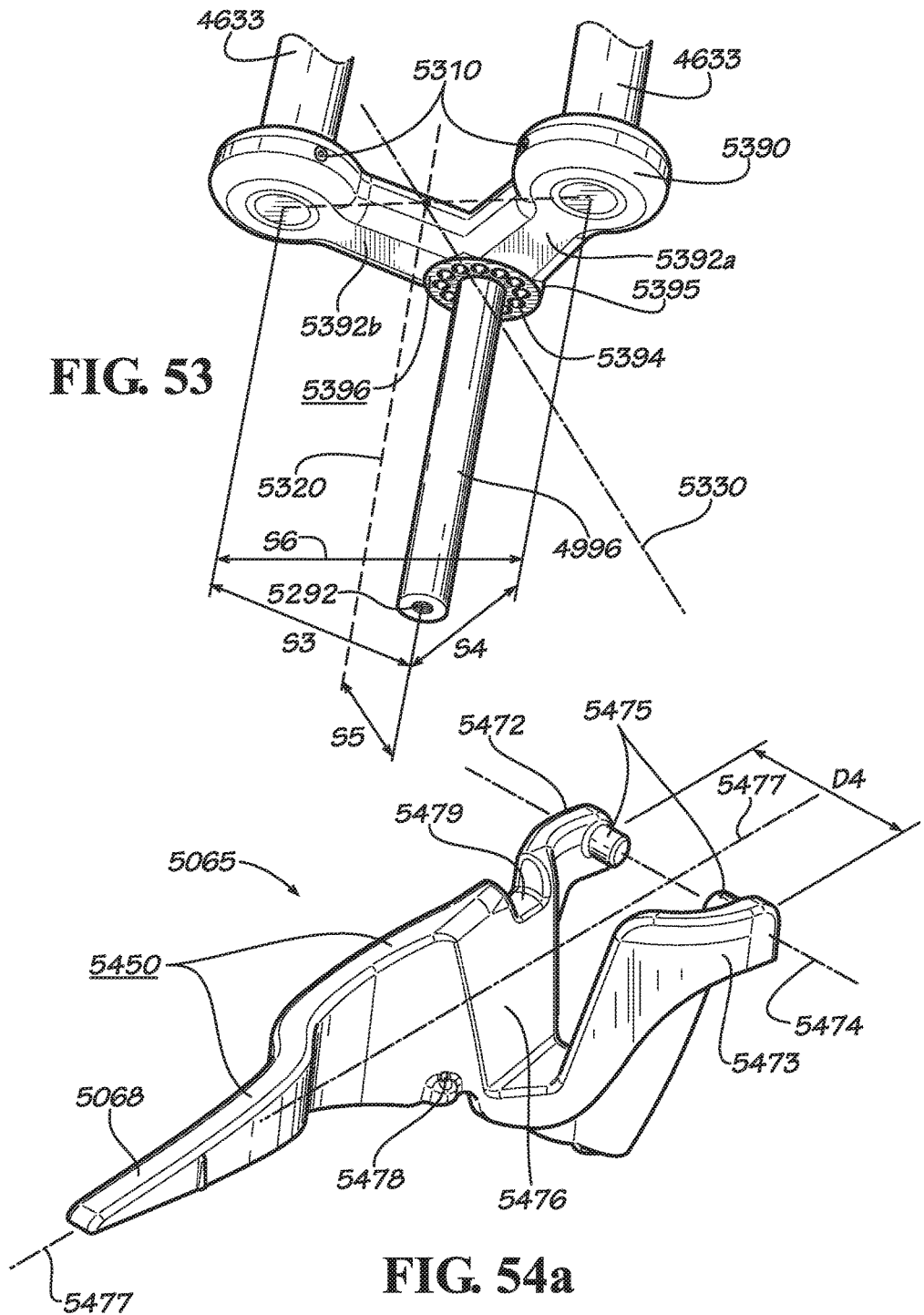
FIG. 53 is a perspective view of a shaft of the transfer apparatus of FIG. 49 with a multi-pole offset arm.
FIG. 54a is a perspective view of a security lever of the transfer device shown in FIG. 49.

FIG. 53 discloses a multi-pole offset arm 5390 including a plurality of arms 5392a,b, a hub 5395, and a plurality of ball detents 5394. The multi-pole offset arm 5390 is shown with an offset arm spacing S3 and an offset arm spacing S4 measured between an axial center of support shaft 4996 and each of the axial centers of the two poles 4633. The multi-pole offset arm 5390 is also shown with an effective offset spacing S5, the effective offset arm spacing S5 measured between a center of the support shaft 4996 and the axis 5320, which in the current embodiment lies in a plane defined by the axes of the two poles 4633 of each corresponding patient care apparatuses 4632. Finally, the multi-pole offset arm 5390 is also shown with pole spacing S6 measured between the centers of the two poles 4633. In various embodiments, the pole 4633 of each patient care apparatus 4632 is secured axially and rotationally by a set screw 5310. In various embodiments, the multi-pole offset arm 5390 allows more than two poles 4633, which may include IV poles or other components of the patient care apparatus 4632. In various embodiments, the multi-pole offset arm 5390 allows attachment of other additional equipment including more patient care apparatuses 4632 than would be feasible with offset arms 4634,4634' including only a single arm. Because in various embodiments it is desirable that the individuals using the transport device and the equipment mounted thereon be able to access the equipment, there is a limit in various embodiments to how high the equipment can be mounted and so the use of multiple poles 4633 on the multi-pole offset arm allow multiple pieces of equipment to be mounted while minimizing the height of each of these pieces of equipment on the patient care apparatus 4632. In various embodiments, the multi-pole offset arm 5390 is any sufficiently rigid structure defining a hole or other mechanisms of attachment for the support shaft 4996 and defining holes or other mechanisms of attachment for the poles 4633 and spaced apart as shown. In various embodiments, the multi-pole offset arm 5390 does not include "arms" per se but resemble a flat disc, plate, or shelf. In various embodiments, the multi-pole offset arm 5390 incorporates or accommodates a shelf such as a shelf 7350 shown in FIG. 73.

In various embodiments, the offset arm spacing S3 and the offset arm spacing S4 of each arm 5392a,b, respectively, of multi-pole offset arm 5390 is dimensioned to position the center of gravity of the patient care device 4638 or the center of gravity of the patient care apparatus 4632 substantially over the support shaft 4996 such that the center of gravity of either the patient care device 4638 or the center of gravity of the patient care apparatus 4632 is aligned vertically with the center of the support shaft 4996 along axis 5320. In various embodiments, the substantial vertical alignment of the center of gravity of the patient care apparatus 4632 with the support shaft 4996 along a vertical axis such as the axis 5320 reduces the tendency of the patient care apparatus 4632 or the transfer device 4631' to lean at an angle from the vertical. Maintaining the patient care apparatus 4632 in a vertical orientation can yield various functional and aesthetic benefits. Maintaining the patient care apparatus 4632 in a vertical orientation can also further improve the reliability of not only individual components of the transfer system 4600 but also the transfer system 4600 as a whole, in some cases reducing the wear experienced by various components by limiting the side loads acting between the support shaft 4996 and the upper housing 4920 and between the support shaft 4996 and the lower housing 4940.

Figure 55:
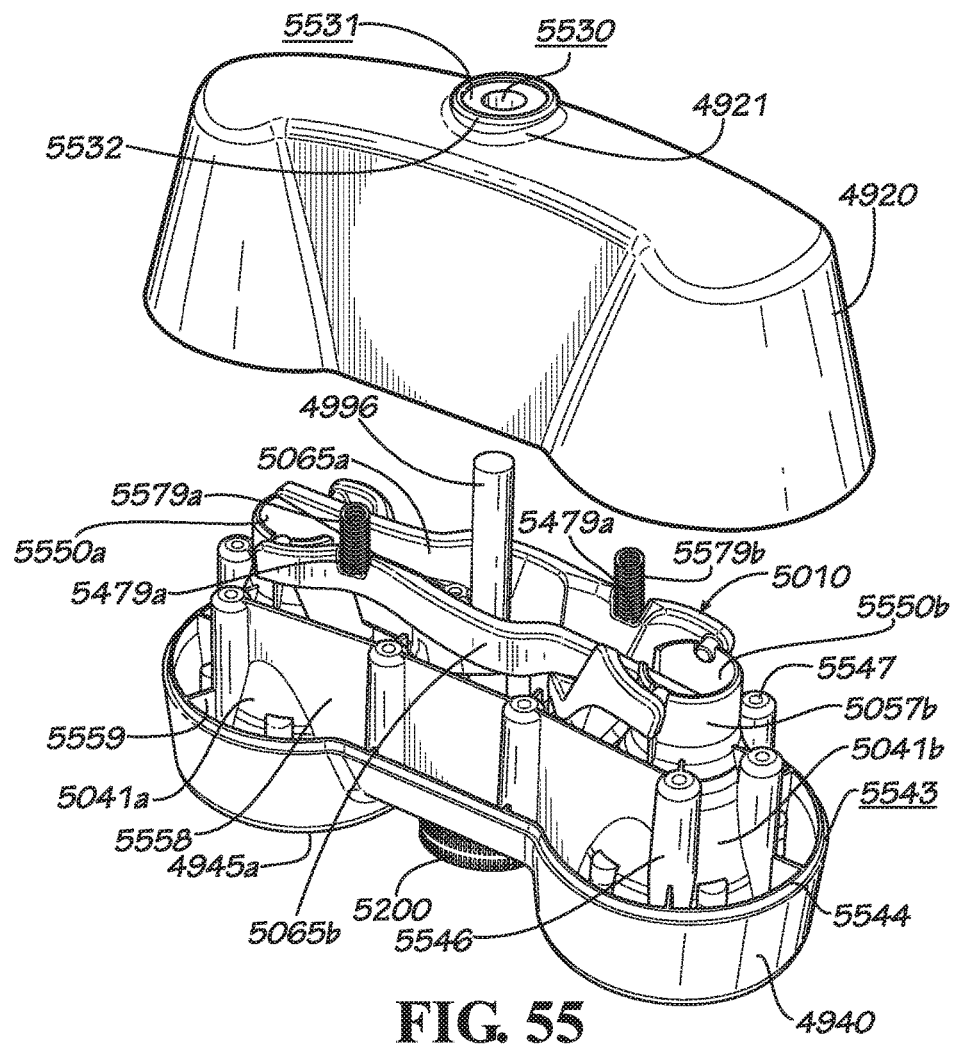
FIG. 55 is a partially-exploded perspective view of the transfer apparatus shown in FIG. 49 with the pole and offset arm removed.

FIG. 54a shows security lever 5065. In various embodiments, security lever 5065 includes the cone feeler 5068a,b, a first fork 5472, a second fork 5473, and a pair of pivot pins 5475 axially aligned along a pivot axis 5474. In various embodiments, upper surface 5450 of security lever 5065 defines a biasing element attachment hole 5478, a biasing element notch 5479, and a clearance slot 5476. Cone feeler 5068 is aligned with longitudinal axis 5477 bisecting the distance between pivot pins 5475 and orthogonal to pivot axis 5474. Because support shaft 4996 is able to nest in the space created between the security levers 5065 (as shown in FIG. 55), the overall height of transfer device 4631' can be minimized to accommodate attachment of more medical apparatuses to the patient care apparatus 4632. In various embodiments, the inside-to-inside spacing equal to a distance D5 between first fork 5472 and second fork 5473 is greater than or equal to the diameter D2 defined by the outside of extension 5057 and also greater than or equal to the diameter D6 defined by the outside of an upper extension 5730 (shown in FIG. 57) such that a surface 5732 (also shown in FIG. 57) is able to fit radially outward of extension 5057. As a result, pivot pins 5475 are supported from below by pivot slots 5056 from below and from above by pivot slots 5735 (shown in FIG. 57) in various embodiments. In various embodiments, the use of pivot slots both above and below pivot pins 5475 instead of pivot holes (not shown) in just the lower housing 4940 or upper housing 4920 improves the ease with which transfer device 4631' can be assembled and disassembled and reduces the number of parts. In various other embodiments, pivot holes can be employed successfully.

FIG. 54b discloses a side view or elevation view of security lever 5065 additionally showing security latch 5080, which in various embodiments defines a lower surface 5140 and includes the latch tip 5066 and the upper edge 5067. In various embodiments, some of which will be explained in more detail below, security lever 5065 is formed with a plurality of ribs 5480 (see FIG. 54c) to provide strength with a minimal amount of material to yield benefits including, but not limited to, lower material cost, reduced weight, and improved manufacturability. FIG. 54c, depicting a bottom view of security lever 5065, shows the ribs 5480 and a plurality of hollow cavities 5490 defined by the ribs 5480.

FIG. 54d discloses the security lever 5065' including a built-in biasing element, embodied here as biasing element 5410. In various embodiments, security lever 5065' includes the previously described features of security lever 5065. In various embodiments, security lever 5065' does not include one or more features of security lever 5065 such as biasing element notch 5479 or biasing element attachment hole 5478. In various embodiments, biasing element 5410 extends from upper surface 5450' of security lever 5065' and includes hinge portion 5440, leg portion 5430, and tip 5420. In order not to interfere with support shaft 4996 and other surrounding structure in various embodiments, biasing element 5410 substantially matches the profile of upper surface 5450'—at least at hinge portion 5440 and tip 5420—when security lever 5065' is viewed from the top or the bottom (i.e. as viewed from the perspective shown in FIG. 54c). In various embodiments, the position of hinge portion 5440 is such as not to interfere with the interior top cavity 5027. In various embodiments, the leg portion 5430 and the tip 5420 of biasing element 5410 is sized so as not to interfere with interior top cavity 5027 even when security lever 5065' is raised towards interior top cavity 5027 causing biasing element 5410 to bend into bent position 5410'. In various embodiments, the curvature of hinge portion 5440 of biasing element 5410 is large enough and the distance from hinge portion 5440 and tip 5420 great enough that the flexing of biasing element 5410 from the unbent position shown in solid lines to the bent position 5411 shown in dotted lines does not result in "plastic" or permanent deformation of the material of biasing element 5410 but rather only "elastic" deformation so that the biasing element 5410 returns to the original unbent position when the security lever 5065' rotates about the pivot pins 5474. In various embodiments, the biasing element 5410 is able to be bent repeatedly in the elastic range and then return to its natural, unbent position. The disclosure of the biasing element 5410 exactly as described here and in FIG. 54d, however, should not be considered limiting. In various embodiments, a security lever such as the security lever 5065 or the security lever 5065' defines a curvature of the lower surface 5140 with a radius R3, which substantially complements a radius (not shown) of the lower edge surface 5150 of the security aperture 5849 of the lower housing 4940 of the transfer device 4631' as shown in FIG. 51c.

FIG. 55 discloses a partially-exploded view of transfer device 4631' with upper housing 4920 lifted away from lower housing 4940. Upper housing 4920 is shown with a shaft bearing surface 5530 and a shoulder bearing surface 5531. In various embodiments, the shaft bearing surface 5530 supports and maintains the substantially vertical orientation of support shaft 4996 as it rotates within transfer device 4631'. In various embodiments, the load on shaft bearing surface 5530 from support shaft 4996 is higher when the center of gravity of the patient care apparatus 4632 is not axially aligned with an axial center of the support shaft 4996 and shaft bearing surface 5530—for example, when no offset arm is used and pole 4633 of the patient care apparatus 4632 is aligned with support shaft 4996. In various embodiments, the use of an offset arm 4634' with offset arm spacing S2, S3, S4, or S5 causes the center of gravity of the patient care apparatus 4632 to become axially aligned with an axial center of the support shaft 4996 and shaft bearing surface 5530. In various embodiments, the shoulder bearing surface 5531 supports and maintains offset arm 4634' and therefore also the patient care apparatus 4632 as offset arm 4634' rotates above shoulder 4921 of upper housing 4920 of transfer device 4631'. In various embodiments, the presence of downward-extending lip 5256 on offset arm 4634' and upward-extending lip 5532 on upper housing 4920 prevent water from entering transfer device 4631' by forcing any liquid trying to enter the joint to overcome the force of gravity, thereby allowing in only water forced into the joint under pressure. In various embodiments, the joint between offset arm 4634' and transfer device 4631' is a watertight joint that does not allow water to enter except under pressures to which it would not be subjected in normal use or even abuse.

Lower housing 4940 is shown assembled with security mechanism 5010—which includes security levers 5065—and with shaft brake mechanism 5200. Also shown are inner walls 5041a,b, throats 5550a,b, an assembly surface 5543, a lip 5544, and a plurality of mounting bosses 5546, mounting bores 5547, reinforcing ribs 5558, and reinforcing ribs 5559. In various embodiments, a pair of biasing elements 5579a,b fit in biasing element notches 5479a,b and are used to keep security levers 5065a,b in the default locked position or the aforementioned first secured position. In various embodiments, biasing elements 5579a,b are not required and only biasing elements 5879a,b are present or no biasing element is present at all. In various embodiments, the security mechanism 5010 minimizes the risk of accidentally disconnecting or dislodging transfer device 4631' from a receiver 4615' to which it may be docked. The security mechanism 5010 is fully enclosed inside transfer device 4631' in the current embodiment. When a first receiver 4615a' is in docking engagement with docking cup 5050a of transfer device 4631', for example, transfer device 4631' cannot be removed from the first docking cone 4615a' as long as docking cup 5050b is not in docking engagement with a second docking cone 4615b' because the engagement of security latch 5080b with security engagement notch 4934a prevents such removal of transfer device 4631' from the first docking cone 4615a'.

Figure 56:
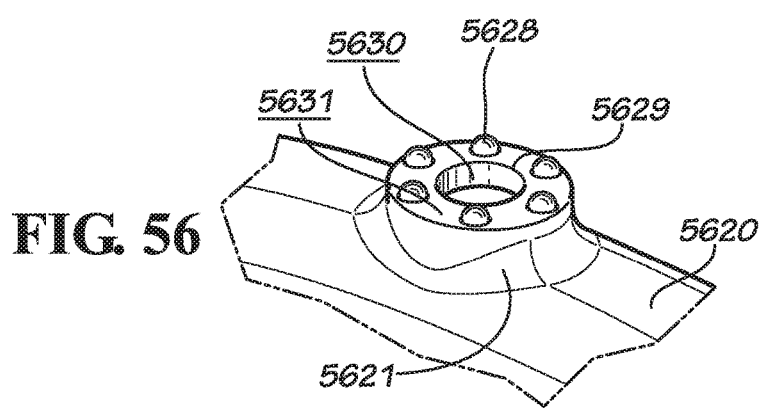
FIG. 56 is a perspective view of another embodiment of an upper housing of the transfer device of FIG. 55.

FIG. 56 discloses another embodiment of an upper housing in the form of an upper housing 5620. Upper housing 5620 includes a shoulder 5621 defining a bore 5629, a top surface 5631, a bore surface 5630, and a plurality of balls 5628. In various embodiments, the inclusion of balls 5628 and ball detents 5394 in multi-pole offset arm 5390 (shown in FIG. 53) or any other offset arm including offset arms 4634', 4634", 4634''' increases the resistance against rotation of offset arm 5394 and provides set angular positions at which offset arm 5394 can be "indexed" or rotated in pre-set increments. This resistance results in a minimum torque having to be applied to offset arm 4634' to produce the force necessary to push the mating balls (such as balls 5628) downward into the shoulder 5621 of upper housing 5620 of transfer device 4631' such that hub bottom surface 5396 clears balls 5628 and the offset arm 5390 can therefore rotate. In various embodiments, a force is necessary to push the balls 5628 into the shoulder 5621 because of the use of compression springs (not shown) behind balls 5628 to keep balls 5628 in the highest possible position inside transfer device 4631'.

Figure 57:
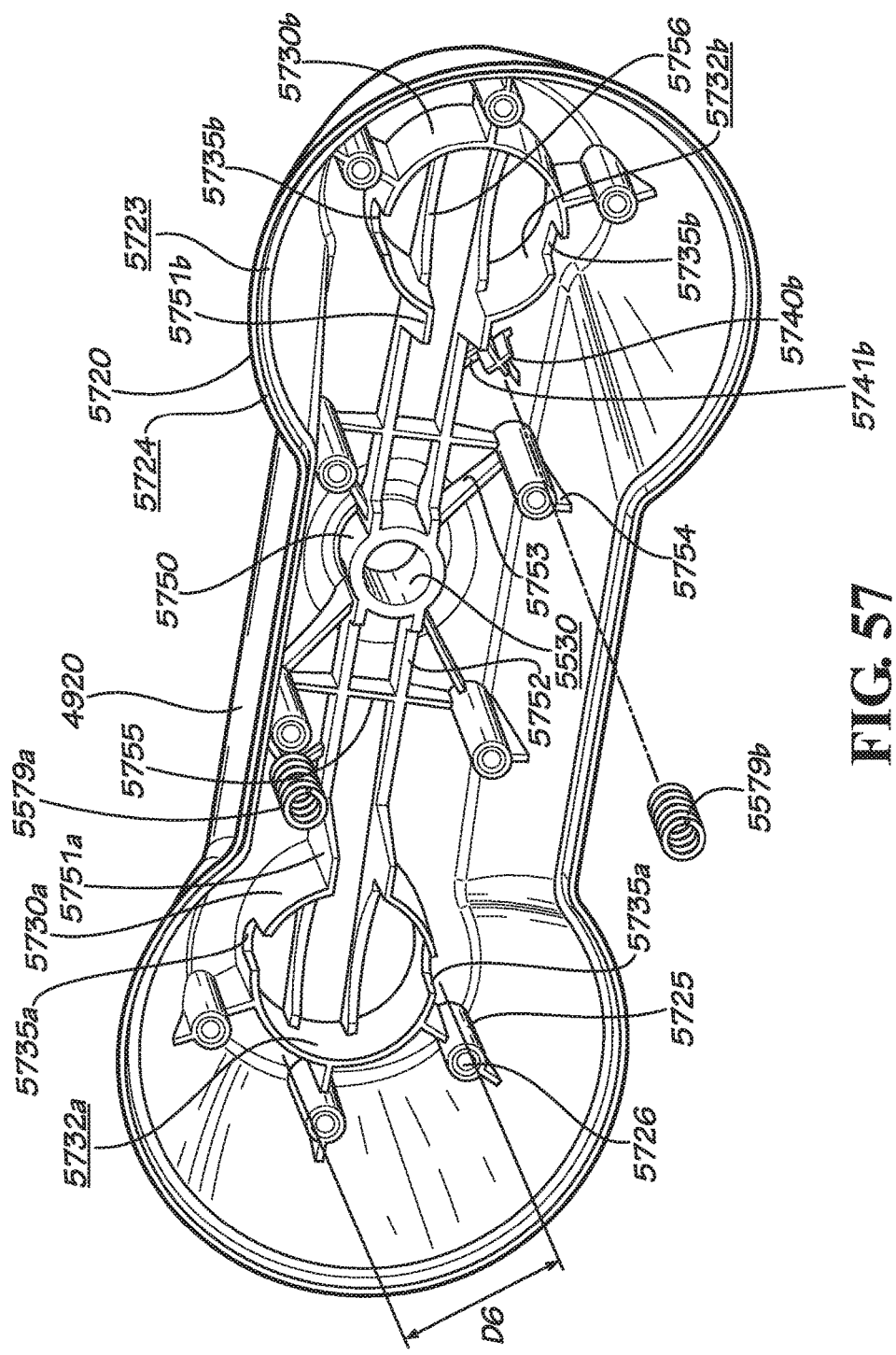
FIG. 57 is a partially-exploded perspective view of the upper housing in FIG. 55 shown together with a pair of biasing elements.

FIG. 57 discloses a partially-exploded view of biasing elements 5579a,b assembled to upper housing 4920. In various embodiments, the biasing elements 5579a,b are assembled to upper housing 4920 at a pair of protrusions 5740a,b (5740a is not shown because it is covered by biasing element 5579a), which are supported by reinforcing ribs 5741 and adapted to accept biasing elements 5579a,b because the protrusions 5740a,b are sized to tightly fit within biasing elements 5579a,b, which are springs in the current embodiment.

Upper housing 4920 is further shown with shaft bearing surface 5530 of upper guide 5750 buttressed with a plurality of longitudinal reinforcing ribs 5752 and a plurality of diagonal reinforcing ribs 5753. A plurality of mounting bosses 5725 defining fastener engagement holes 5726 are shown buttressed with a plurality of reinforcing ribs 5754 and a plurality of reinforcing ribs 5755. In various embodiments, the mounting bosses 5725 are positioned in the upper housing 4920 to receive fasteners from the bottom (as shown in FIG. 52) in order to keep the top or exposed upper exterior surface US1 of transfer device 4631' smooth to facilitate cleaning by the elimination of rough or discontinuous surfaces that could create crevices or otherwise inhibit cleaning Each of the upper extensions 5730 is shown buttressed with a plurality of ribs 5751 and a plurality of ribs 5756, longitudinally aligned with reinforcing ribs 5752 in the current embodiment. Mating with assembly surface 5543 and lip 5544 are surface 5724 of lip 5720 and assembly surface 5723, respectively.

Figure 58:
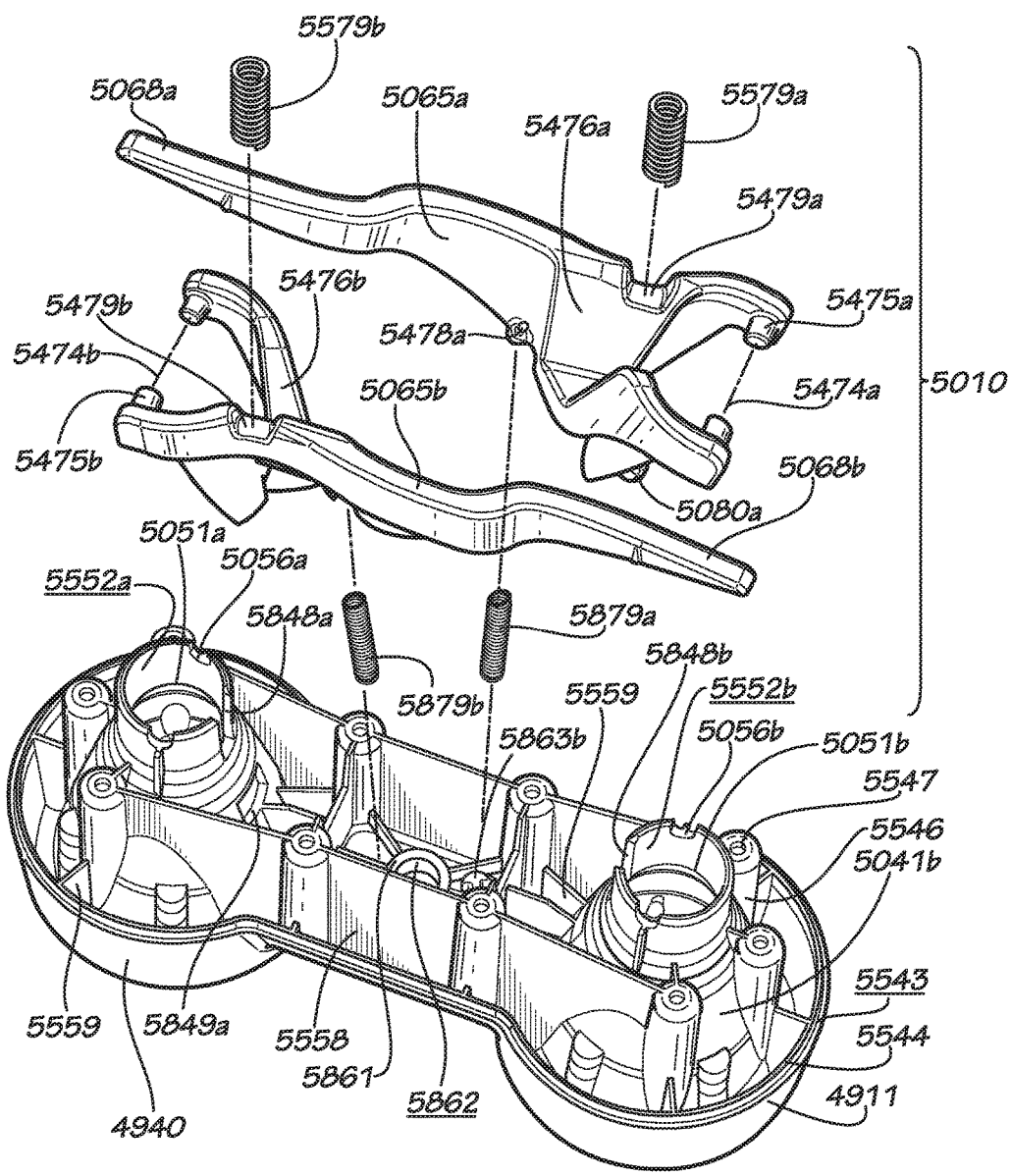
FIG. 58 is an exploded view of a lower housing and a security mechanism of the transfer device of FIG. 55.

FIG. 58 shows an exploded view of security mechanism 5010 together with lower housing 4940. Mounting bosses 5546 and mounting bores 5547 defined in lower housing 4940 are shown reinforced with reinforcing ribs 5559 and reinforcing ribs 5558. In addition, mounting bores 5547 of lower housing 4940 are axially aligned with fastener engagement holes 5726 of upper housing 4920. A throat inside surface 5552 is shown starting from neck plane 5051 defined by neck 5051a and neck 5051b. As previously mentioned, biasing elements 5579a,b are shown together with biasing elements 5879a,b even though both sets of biasing elements (both biasing elements 5579a,b and biasing elements 5879a,b) are not required for proper operation. Furthermore, in some embodiments one or more security levers 5065 will include a biasing element that derives its springiness from the elasticity and memory of the material. In various embodiments, the material used to form such a security lever will include any one or more of a group of flexible materials including, but not limited to, spring steel, plastics, and composites. When utilized, each of biasing elements 5879a,b stretch between the attachment hole 5478—present in some embodiments—or lower surface 5069 of security lever 5065 and an attachment bosses 5863 of lower housing 4940. Furthermore, each inner wall 5041 of docking cup 5050 is shown reinforced with a plurality of reinforcing ribs 5559. In various embodiments, the biasing element 5579 is a compression spring. In various embodiments, the biasing element 5879 is a tensile spring.

In various embodiments, each of the components of transfer system 4600 including transfer device 4631' and the biasing element and are made from magnetic-resonance-safe or magnetic-resonance-imaging-safe (MR-safe or MRI-safe, respectively) materials. Materials that are MR-safe can be selected from a group including, but not limited to, plastic, composites, aluminum, non-ferritic (typically non-magnetic) stainless steels and other non-non-magnetic or non-ferrous metals that are not adversely affected by or that do not adversely interfere with an environment utilizing magnetic-resonance technology. In various embodiments, the security levers 5065 are at least initially formed of an extruded shape. In various embodiments, the security levers 5065 are formed into a molded or cast shape using an additive manufacturing process, wherein additive manufacturing processes include, but are not limited to, injection molding, casting, and three-dimensional printing. However, the disclosure of an additive manufacturing process should not be considered limiting. In various embodiments, the security levers 5065 are molded from a polymer material.

Figure 59:
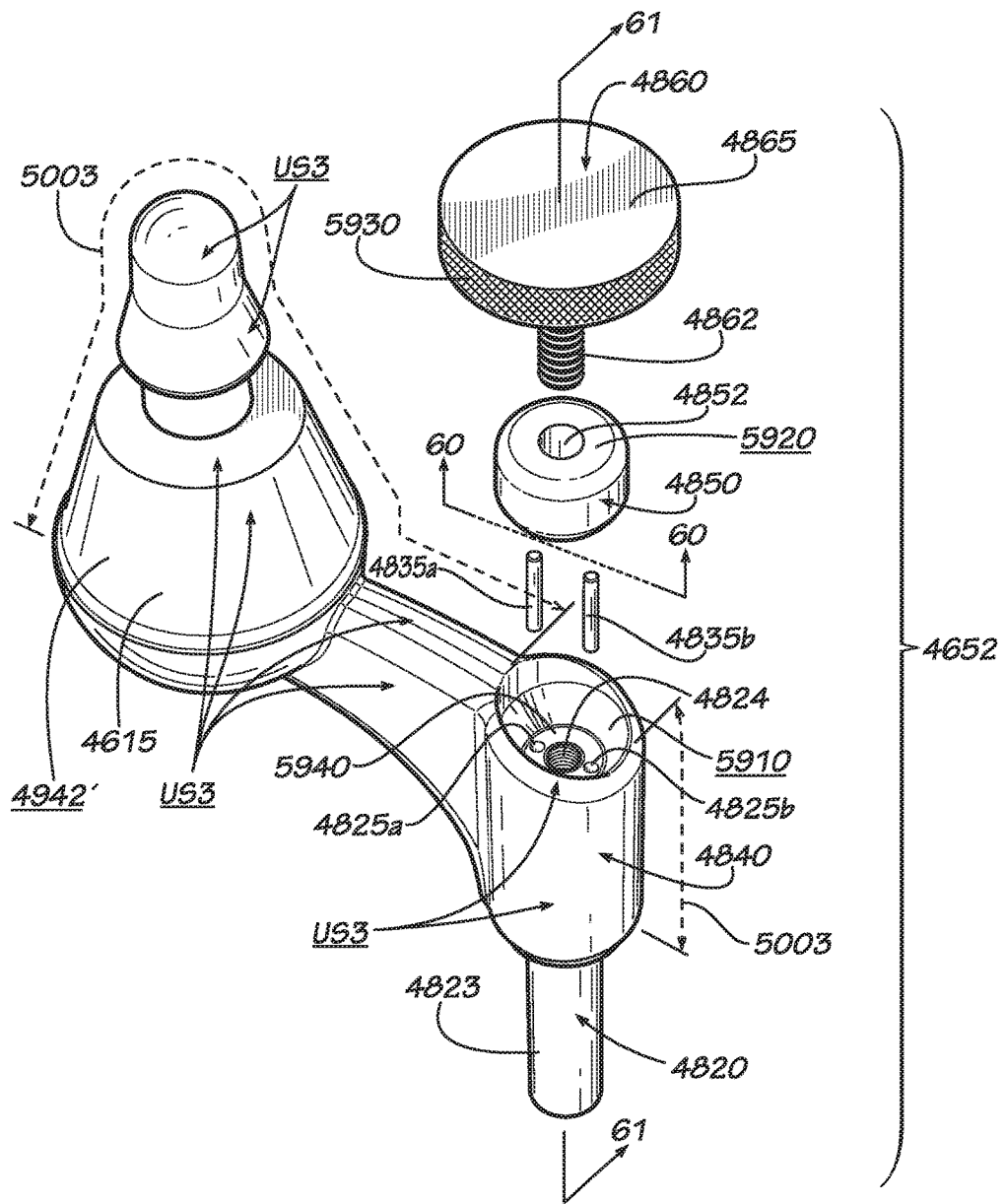
FIG. 59 is a partially-exploded detail view of the mobile support platform of FIG. 48 taken from detail 59 of FIG. 48.

FIG. 59 discloses additional details of the components of receiver arm 4652 shown in detail 59 of FIG. 48. Brake shaft 4820 is shown assembled in arm portion 4840 and ready to receive fasteners 4835a,b, brake spacer 4850, and brake fastener 4860. Arm portion 4840 includes a surface 5910 against which conical surface 6020 (shown in FIG. 60) of brake spacer 4850 contacts when threaded portion 4862 of brake fastener 4860 is assembled through bore 4852 of brake spacer 4850 into bore 4824 and tightened against surface 5920 of brake spacer 4850. As explained above, exposed upper exterior surfaces US3—and other exposed upper exterior surfaces of the transfer system 4600 or the components thereof—are vertical or sloped outward in various embodiments so that no horizontal surfaces exist that can retain or trap a liquid—possible at least due to the surface tension of the liquid—and become a source of increased infection or contamination risk.

Figure 60:
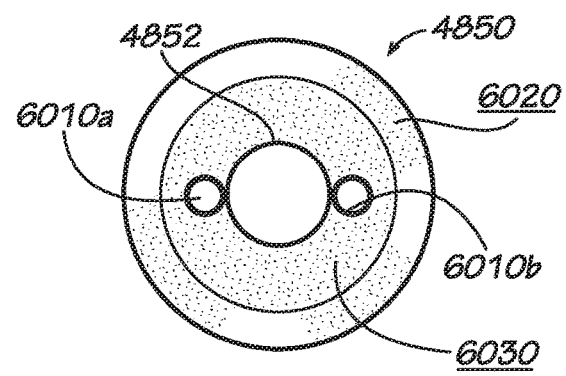
FIG. 60 is a bottom view of a brake spacer of the mobile support platform of FIG. 48 taken along line 60-60 of FIG. 59.

FIG. 60 discloses a bottom view of brake spacer 4850 including bore 4852 and fastener bores 6010*a,b*. Fastener bores 6010*a,b* are sized to accept a portion of fasteners 4835*a,b* to align the brake spacer 4850 with the brake shaft 4820.

Figure 61:
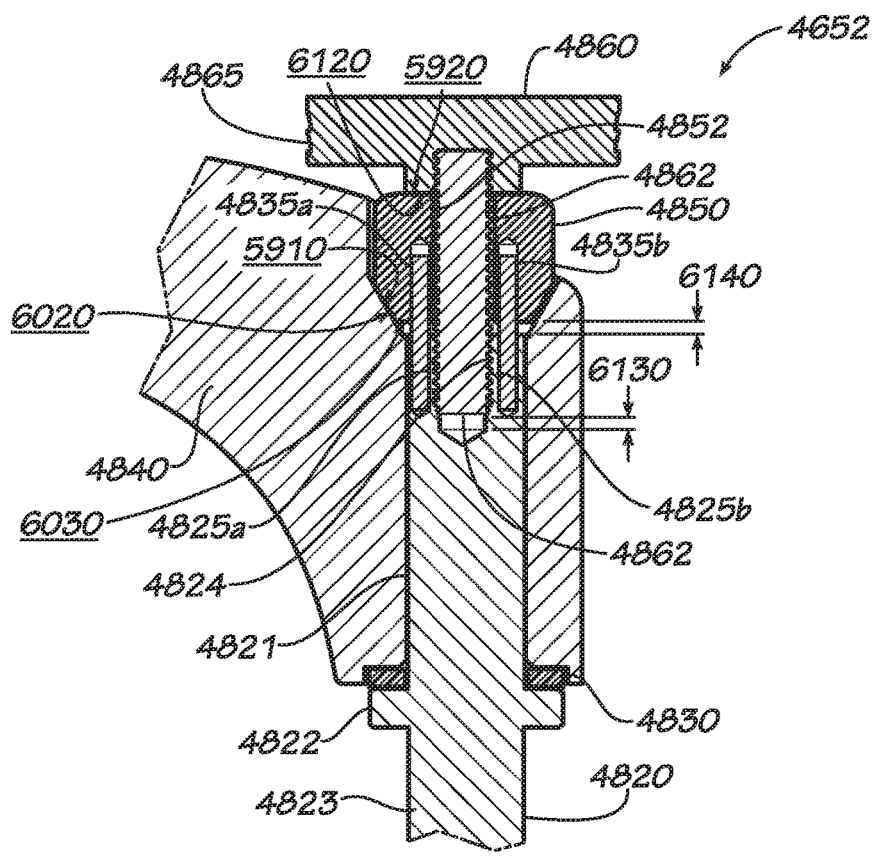
FIG. 61 is a sectional view of the mobile support platform of FIG. 48 taken along line 61-61 of FIG. 59.

FIG. 61 shows a sectional view of the components of receiver arm 4652 of FIG. 59 as they interact to dampen or restrict the rotational movement of arm portion 4840 relative to brake shaft 4820. When brake fastener 4860 is tightened, surface 6120 of fastener head 4865 contacts surface 5920 of brake spacer 4850 and subsequently causes conical surface 6020 to contact surface 5910 of arm portion 4840. In various embodiments where brake spacer 4850 is made of a flexible, deformable material such as rubber, the coefficient of friction between arm portion 4840 and brake spacer 4850 is increased and rotational movement of arm portion 4840 relative to brake shaft 4820 is restricted or prevented as brake spacer 4850 is compressed. In various embodiments, such compression and the resulting deformation of brake spacer 4850 is allowed by the incorporation of gap 6140 between surface 6030 of brake spacer 4850 and surface 5940 (shown in FIG. 59) of brake shaft 4820 and by gap 6130 between a bottom of bore 4824 of brake shaft 4820 and an end of threaded portion 4862 distal to fastener head 4865 of brake fastener 4860. In various embodiments, metal-to-metal contact between arm portion 4840 and brake shaft 4820 is prevented by forming washer 4830 from a non-metallic material. In various embodiments, because the soft material of washer 4830 and brake spacer 4850 will wear before any of the metallic parts and will typically be relatively low in manufacturing cost and simple to replace, service of the receiver arm 4652 can be kept at a minimum.

In various embodiments, the brake spacer 4850 is coupled to the brake shaft 4820. In various embodiments, the brake spacer 4850 is coupled to the brake shaft 4820 with fasteners 4835*a,b*. In various embodiments, fasteners 4835*a,b* are inserted into fastener bores 4825*a,b* of brake shaft 4820 and are inserted into fastener bores 6010*a,b* of brake spacer 4850 to prevent the rotation of brake spacer 4850 with respect to brake shaft 4820. In various embodiments, coupling the brake spacer 4850 to the brake shaft 4820 with fasteners 4834*a,b* and contacting arm portion 4840 with brake spacer 4850 fixes arm portion 4840 while reducing the risk of brake fastener 4860 loosening simply by the forced rotation of arm portion 4840 when arm brake mechanism 4730 has been tightened. In various embodiments, only one fastener 4834 coupled with one bore 4824 is required to prevent this loosening.

FIG. 62*a* shows another view of the shaft brake mechanism 5200 further including the shaft brake assembly 6200. In various embodiments, shaft brake mechanism 5200 includes shaft brake assembly 6200, where shaft brake assembly 6200 includes the upper plate 6220, the middle plate 6230, the lower plate 6240, brake pads 5220, standoff fasteners 6300, and the brake fastener 5240. In various embodiments, upper plate 6220 includes an upper surface 6222 and a lower surface 6221 (shown in FIG. 65) defining a plurality of assembly holes 6223, each of which is threaded to accommodate the assembly of standoff fasteners 6300. In various embodiments, middle plate 6230 includes an upper surface 6232 and a lower surface 6231 (shown in FIG. 65) defining a plurality of assembly holes 6233, each of which is sized to allow movement of middle plate 6230 with respect to standoff fasteners 6300. In various embodiments, a diameter D9 of each of the assembly holes 6233 will be equal to or greater than a diameter D7 of standoff fastener 6300 in order to allow such movement of middle plate 6230 with respect to standoff fasteners 6300. In various embodiments, lower plate 6240 includes an upper surface 6242 and a lower surface 6241 (shown in FIG. 65) defining bore 6245 and a plurality of assembly holes 6243, each of which is sized to allow movement of lower plate 6240 with respect to standoff fasteners 6300. In various embodiments, a diameter D8 of each of the assembly holes 6243 will be equal to or greater than a diameter D7 of standoff fastener 6300 in order to allow assembly of lower plate 6240 with standoff fasteners 6300. In the current embodiment, movement of lower plate 6240 with respect to standoff fasteners 6300 is not required for shaft brake mechanism 5200 to function properly. As described previously, brake fastener 5240 includes the threaded portion 5242, the knurled portion 5244, and the standoff portion 5246.

FIG. 62*b* discloses a detail view of the bottom end of the shaft 4996, which in various embodiments includes a surface 5295 adjacent to each flat 5290.

Standoff fastener 6300 is shown in FIG. 63. In various embodiments, each standoff fastener 6300 includes a body 6330 with diameter D7, a head 6320, a threaded portion 6350, and a distal end 6340 opposite the head 6320 along an axial direction of the standoff fastener 6300—help maintain a constant distance between upper plate 6220 and lower plate 6240, prevent the separation of any components of shaft brake assembly 6200 (shown in FIG. 62) including brake pads 5220 when not assembled to transfer device 4631', and facilitate serviceability of the transfer device 4631' in the field by making it possible to replace the entire shaft brake assembly 6200 as a single pre-assembled component if and when wear occurs sufficient to require service.

Figure 64A:
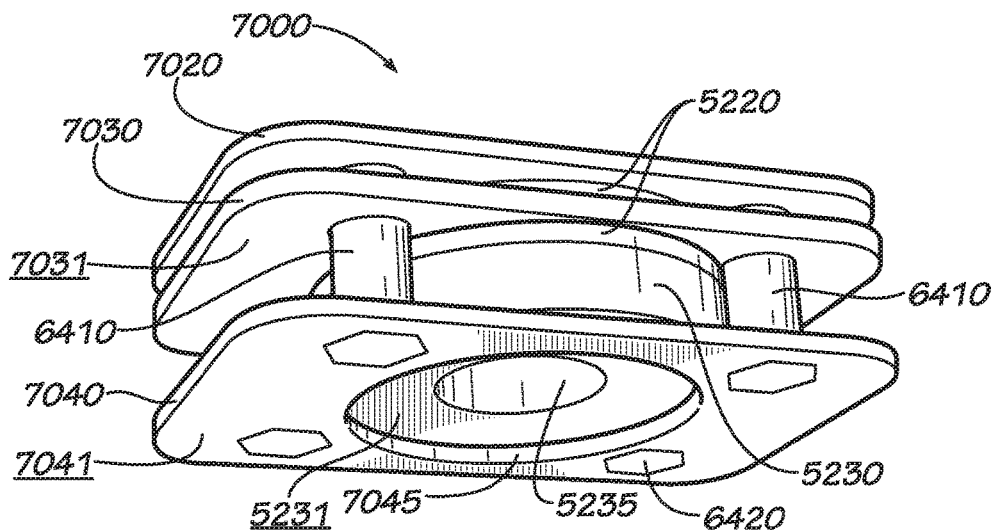
FIG. 64a is a bottom perspective view of a shaft brake mechanism of the transfer device of FIG. 55 according to another embodiment of the present disclosure.
Figure 64B:
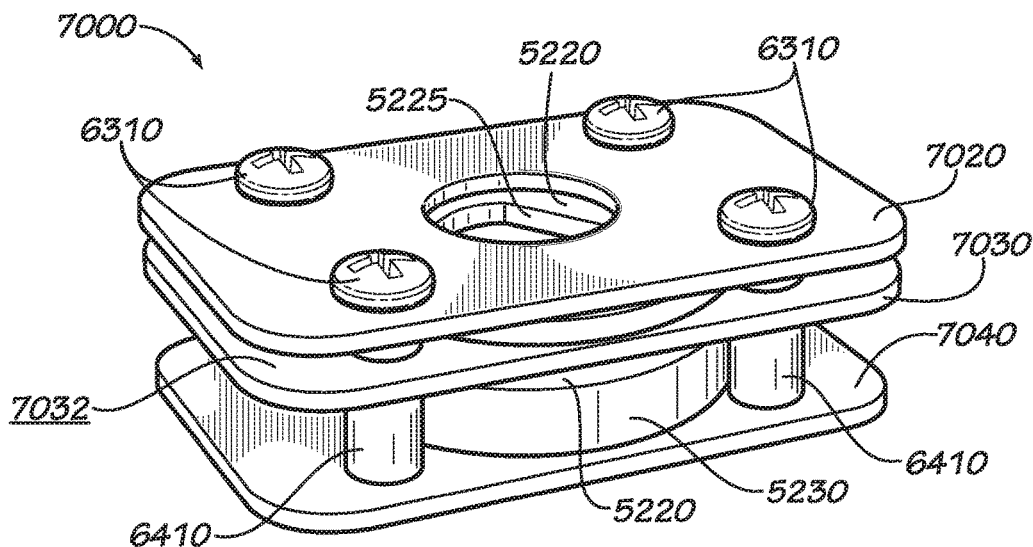
Figure 64C:
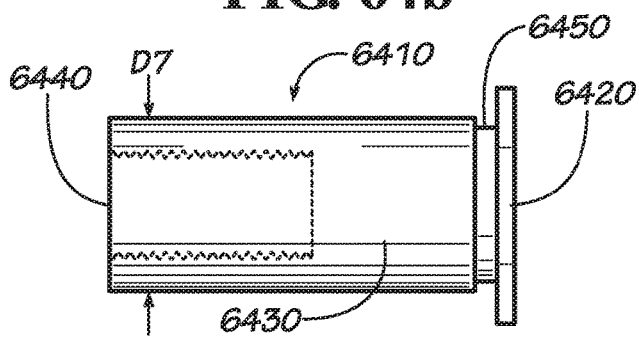

FIGS. 64*a* and 64*b* disclose two separate perspective views of another embodiment of a shaft brake assembly 7000. Shaft brake assembly 7000 includes upper plate 7020, lower plate 7040, and middle plate 7030, the middle plate 7030 defining holes (not shown) for passage of a plurality of standoff fasteners 6410 (shown also in FIG. 64*c*) such as a known PEM press-in or "clinch-style" fastener—each with a body 6430 of diameter D7 that is less than the diameter of each of the corresponding holes in middle plate 7030. See, e.g., Item 93090A460 available from McMaster-Carr Supply Company. Shaft brake assembly 7000 further includes a head 6420, and a distal end 6440 opposite the head 6420 along an axial direction of the standoff fastener 6410—and a plurality of fasteners 6310, which together maintain a constant distance between upper plate 7020 and lower plate 7040. In various embodiments, the head 6420 of each standoff fastener 6410 is made flush with surface 7041 of lower plate 7040 by use of a pressing operation that will sufficiently deform the material around a plurality of holes in the lower plate 7040 to upset and move it into a groove 6450 (shown in FIG. 64*c*) defined in standoff fastener 6410. In various embodiments, shaft brake assembly 7000 also includes spacer 5230. In lieu of spacer 5230, the standoff portion 5246 of brake fastener 5240 can be lengthened as desired and the length of standoff fasteners 6410 shortened to create a shaft assembly more closely resembling shaft brake assembly 6200.

Figure 65:
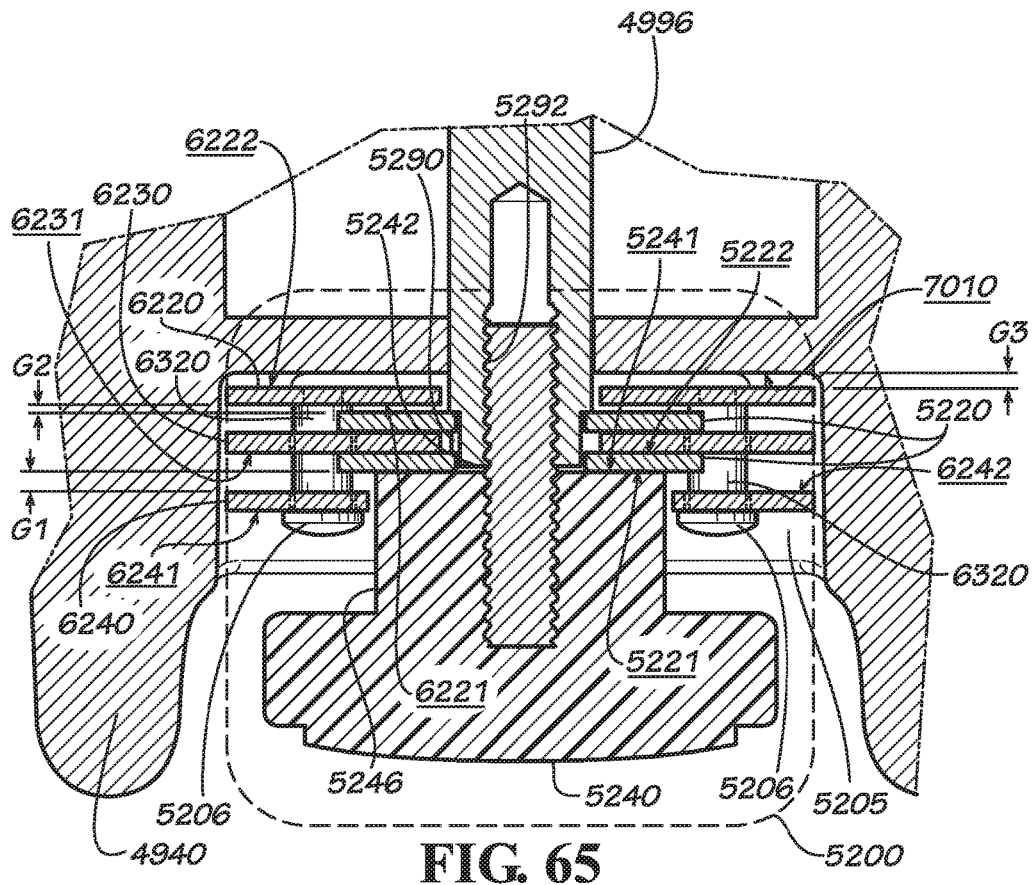
FIG. 65 is a sectional view of the shaft brake mechanism of FIG. 62 installed in the transfer system of FIG. 49 and arranged in the view of detail 65 of FIG. 50.

FIG. 65 shows a sectional view of previously described shaft brake mechanism 5200—including shaft brake assembly 6200—as it interacts with lower housing 4940 and support shaft 4996 to lock the rotation position of support shaft 4996. One or more brake pads 5220, much like the disc calipers in an automobile disc brake system, are positioned on one or both sides of middle plate 6230. When the brake fastener 5240 is tightened against one of a pair of brake pads 5220, the middle plate 6230 is subsequently sandwiched between brake pads 5220. The resulting friction between the middle plate 6230 and each of the brake pads 5220 results in restriction of rotational movement of the brake pads 5220 with respect to the middle plate 6230. In various embodiments, the lower surface 6231 of the middle plate 6230 contacts an upper surface 5222 of a lowermost brake pad 5220 positioned facing the lower surface 6231. In various embodiments, the upper surface 6232 of the middle plate 6230 contacts a lower surface 5221 of an uppermost brake pad 5220 positioned facing the upper surface 6232. In contrast to the disc calipers on an automobile disc brake assembly, the "disc" or middle plate 6230 of shaft brake mechanism 5200 does not rotate, being locked inside the rectangular recess 5205 in lower housing 4940 due to the rectangular shape of the middle plate 6230. Because the middle plate 6230 cannot rotate inside the rectangular recess 5205 of lower housing 4940, the brake pads 5220 also cannot rotate, thereby locking the support shaft 4996 to which the patient care apparatus 4632" is attached.

In various embodiments, a gap G1 is defined by the distance between upper surface 6242 of lower plate 6240 and lower surface 5221 of the lowermost brake pad 5220. In various embodiments, a gap G2 is defined by the distance between an upper surface 5222 of the uppermost brake pad 5220 and the lower surface 6221 of the upper plate 6220. In various embodiments, a gap G3 is defined by the distance between the upper surface 6222 of upper plate 6220 and the uppermost portion of surface 7010 of the lower housing 4940. In various embodiments, gap G2 and gap G3 are reduced to zero to reduce the vertical movement of support shaft 4996 and therefore also patient care apparatus 4632'. In various embodiments, gap G1 is maintained to allow the free rotational movement of support shaft 4996 when shaft brake mechanism 5200 is not engaged.

In various embodiments, the amount of frictional force generated by a specific brake fastener torque (as applied to brake fastener 5240, for example) can be adjusted by changing the material of middle plate 6230 or the brake pads 5220. In various embodiments, both middle plate 6230 and the brake pads 5220 are rigid enough not to deform even when the shaft brake mechanism 5200 is engaged and therefore causing various forces to act on each. In various embodiments, this frictional force can be adjusted by changing the contact surface area between middle plate 6230 and the brake pads 5220. In various embodiments, this frictional force can be adjusted by adjusting other factors including the ease at which the brake fastener 5240 can be tightened. If the force required to engage the brake is decreased, this effectively increases the frictional force generated should the applied force remain constant. Individual parts of the shaft brake assembly 6200 or the various other embodiments thereof can be serviced or the subassembly replaced as a whole as described previously. In various embodiments, recesses (not shown) will be created in lower housing 4940 to create space for the heads of fasteners 6310 of shaft brake assembly 7000 or to provide an attachment point for the aforementioned biasing elements 5879*a,b*. In various embodiments, both functions can be accomplished in the same structure by locating the attachment bosses 5863*a,b* coaxial with fasteners 6310. In various embodiments, the brake fastener 5240 is adapted to be tightened or is tightenable by hand without the necessity for tools. In various embodiments, the brake fastener 5240 includes a knob. The design of the knurled portion 5244 of the knob 5240 can facilitate hand tightening by the incorporation of features that allow a user's fingers to rotate the knob with only a minimal percentage of the applied force required to keep the user's fingers from slipping on the knob.

In various embodiments, a shaft brake mechanism (not shown) can be created from shaft brake assembly 6200 by removal of lower plate 6240 and standoff fasteners 6300. While both embodiments will function in the same way during use, the shaft brake assembly 6200 is installed and removed as a subassembly while the components of the shaft brake mechanism without lower plate 6240 and standoff fasteners 6300 can be removed individually as loose parts. As previously described in relation to shaft brake assembly 5200, it will benefit the end user or maintenance person in various embodiments to be able to quickly replace the shaft brake assembly 7000 without risk of losing small parts or reinstalling them incorrectly. In various other embodiments, the benefits of the shaft brake mechanism requiring fewer parts will outweigh the service benefits.

In various embodiments, only one brake pad 5220 is utilized in the shaft brake mechanism. In various embodiments, fewer components are used to accomplish the shaft-braking function. In various embodiments, shaft brake fastener 5240 and a single brake pad 5220 are used in combination with a shortened support shaft 4996 that protrudes a distance below an uppermost portion of surface 7010 that is no more than the thickness of a single brake pad 5220. In such an embodiment, the shaft brake fastener 5240 tightens the brake pad 5220 directly against the uppermost portion of surface 7010 of transfer device 4631' to create the desired resistance to rotational movement of brake pad 5220 and therefore also support shaft 4996 and the patient care apparatus 4632. In various embodiments, neither shaft brake assembly 7000 nor shaft brake assembly 6200 is required at all as brake fastener will sufficiently tighten against lower housing 4940, causing surface 7010 of lower housing 4940 to serve either directly or indirectly as a brake pad to resist rotational movement of offset arm 4634' and the patient care apparatus 4632 with respect to transfer device 4631'. As disclosed in FIG. 62*b*, in various embodiments, the upper brake pad 5220 is compressed against the surface 5295 adjacent the flat 5290 of the shaft 4996 by the shoulder 5246 of the knob 5240. In various embodiments, the surface 5295 is parallel to the brake pad 5220, at least when the brake pad 5220 is compressed against the surface 5295.

Figure 66:
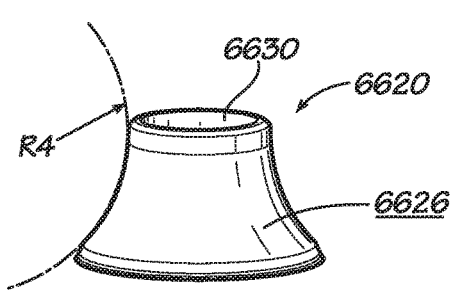
FIG. 66 is a perspective view of a scalloped cone insert of a receiver of the transfer system of FIG. 49.

FIGS. 66 and 67 show two additional embodiments of a lower portion of a receiver arm 4614. In various embodiments, lower portion 4932 of receiver arm 4614 (as shown in FIGS. 49 and 50, for example) can be substituted with a lower portion 6620 having a scalloped or concave side surface 6626 and an inner bore 6630. In various embodiments, the side surface 6626 will define a surface having radius of curvature R4, the radius being measured in a cross-section taken through a vertical centerline of lower portion 6620. In various embodiments, the side surface 6626 will define a surface having a radius that varies across the surface even to the point of having an infinite radius (i.e. representing a straight line) in some areas, the radius being measured in a cross-section taken through a vertical centerline of lower portion 6620. In various other embodiments, the lower portion 4932 of the receiver arm 4614 can be substituted with a lower portion 6720. In various embodiments, lower portion 6720 includes an angled side surface 6726 and an inner bore 6730 but does not include the plurality of reliefs 4943 defined in angled side surface 4942 of receiver 4615'.

In various other embodiments, the receiver arm 4614—including any of the aforementioned shape variations—is integrally molded, cast, machined or otherwise formed in one piece and fasteners are not required to assemble and maintain the integrity of the component. For the purposes of the current disclosure, to be "integrally-formed" or "integrally formed" means to be molded or shaped into a single part during the forming process and to be a "unitary" part means to remain a single indivisible homogeneous part throughout the forming process.

Figure 68:
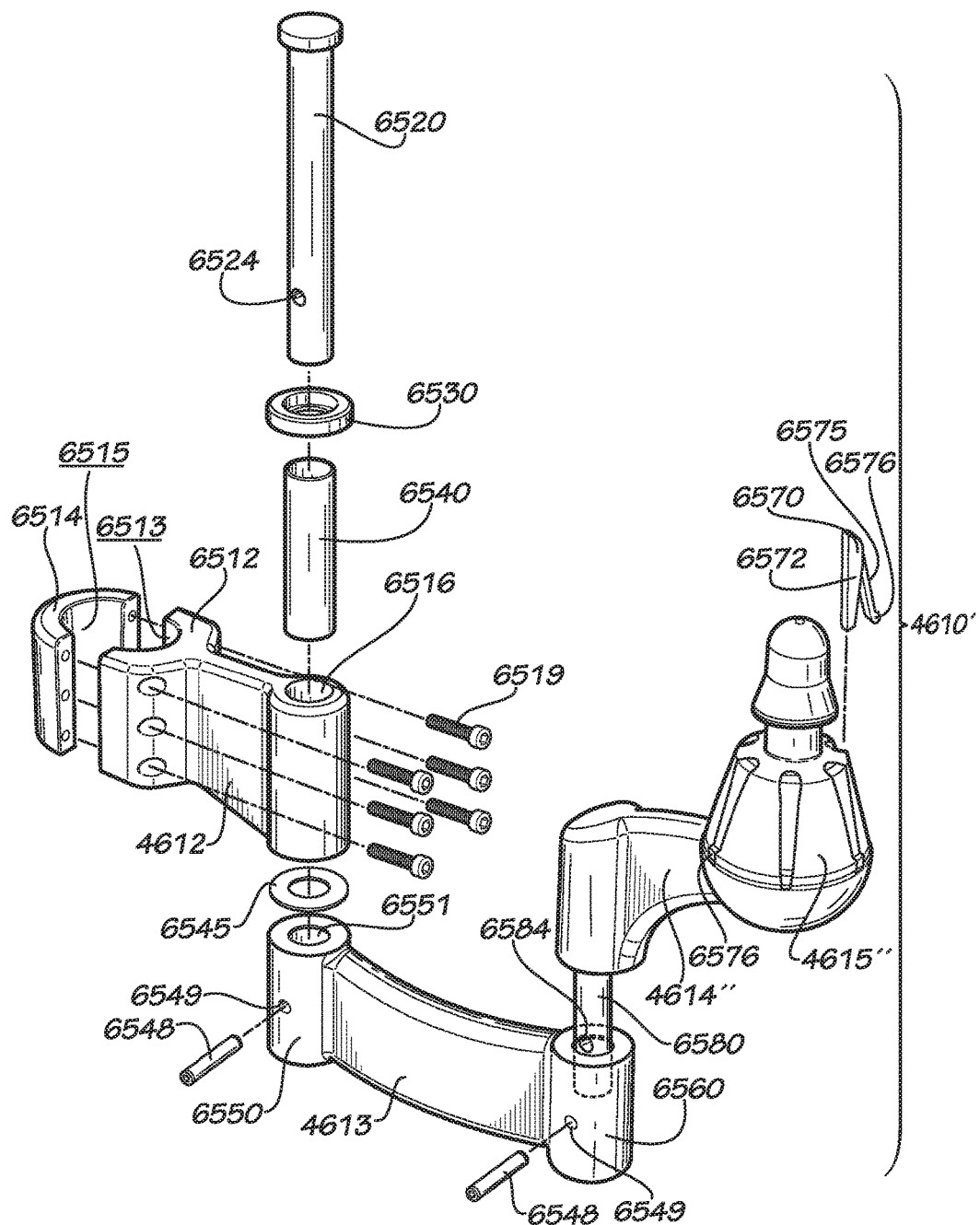
FIG. 68 is an exploded view of a stationary support platform of another embodiment of the transfer system in FIG. 46.

FIG. 68 shows an exploded view of another embodiment of a stationary support platform 4610' of FIG. 46 without mounting pole 4611. As described above, stationary support platform 4610 includes mounting pole 4611, pole link arm 4612, and connecting link arm 4613. In addition to including these components of stationary support platform 4610, stationary support platform 4610' further includes a receiver arm 4614" with a receiver 4615". In various embodiments, stationary support platform 4610' includes various connecting elements including, but not limited to, a hinge pin 6520, a washer 6530, a bushing 6540, a flat washer 6545, a hinge pin 6580, and one or more pins 6548—in various embodiments a clevis pin. In various embodiments, an end of the pole link arm 4612 distal to its attachment with mounting pole 4611 is connected through use of a bore 6516 to an end 6550 of connecting link arm 4613 by assembly of hinge pin 6520 through bore 6516 of pole link arm 4612 and into bore 6551 of the end 6550 of connecting link arm 4613. In various embodiments, the washer 6530 will be positioned around hinge pin 6520 and between a head of hinge pin 6520 and pole link arm 4612. In various embodiments, bushing 6540 will be positioned inside bore 6516 between pole link arm 4612 and hinge pin 6520. In various embodiments, flat washer 6545 will be positioned around hinge pin 6520 and between pole link arm 4612 and connecting link arm 4613. In various embodiments, a pin 6548 is shown inserted through a hole 6549 of end 6550 of connecting link arm 4613 and into a hole 6524 of hinge pin 6520 to lock the connection between the pole link arm 4612 and the connecting link arm 4613. A plurality of fasteners 6519 attach part 6512 of the pole link arm 4612 to part 6514 of the pole link arm 4612 sufficient to secure pole link arm 4612—including an inner surface 6513 of part 6512 and an inner surface 6515 of part 6514 in various embodiments—to mounting pole 4611. In various embodiments, receiver arm 4614" is connected to end 6560 of connecting link arm 4613 by assembly of hinge pin 6580 into a bore in end 6560 (not shown) and a pin 6548 is inserted through the hole 6549 defined in end 6560 of connecting link arm 4613 and into a hole 6584 defined in hinge pin 6580. Fasteners (not shown) and bushings (not shown) in receiver arm 4614" facilitate rotation of receiver arm 4614" with respect to connecting link arm 4613, and in various embodiments, a washer (not shown) will be inserted between receiver arm 4614" and connecting link arm 4613 to improve the function of the joint. Additional link arms 4613 may be added to a stationary support platform such as stationary support platform 4610' to extend the reach of a receiver such as receiver 4615".

As described above and shown in FIG. 68, flexible pawls such as pawl 6570 can be incorporated into receiver 4615' in FIG. 46 and receiver 4615" in FIG. 68. In various embodiments where pawl 6570 is used as a rotation-dampening element, protruding portion 6576 of pawl 6570 engages with features (not shown) inside a docking cup 5050' that will resist movement of the receiver 4615" with respect to the docking cup 5050'. In various embodiments, these features include a plurality of detents (not shown) defined in each docking cup—detents into which one or more pawls can engage but also disengage under sufficient force to push protruding portion 6576 clear of inside surface 5054 of docking cup 5050. In various embodiments, the features into which pawls 6570 engage allow transfer device 4631' to rotate with respect to receiver 4615" when transfer device 4631' is pushed or pulled by hand with sufficient force but prevent transfer device 4631' from swinging wildly or freely on its own during use. In various embodiments, each of these detents resembles relief 4943 but are defined in the inside surface 5054 of docking cup 5050. In various embodiments, the depth of each of these detents or the radius—including the radii at both the entrance and exit of the detent—can be adjusted to increase the force necessary to rotate the transfer device 4631'. In various embodiments, transfer device 4631' can be rotated by hand about receiver 4615" (or any other compatible receiver) with sufficient force but is prevented from swinging wildly. As shown in FIG. 68, the structure of pawl 6570 with a base portion 6572 and a flex portion 6575 allows movement of protruding portion 6576 away from the inside of the docking cup 5050' when the torque is sufficient high.

Figure 33:
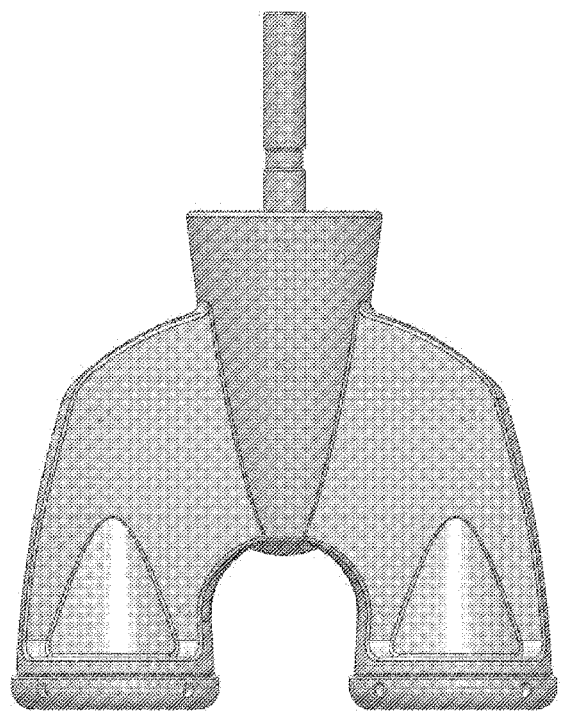
FIGS. 33-39 are various views of a second embodiment of the transfer device of the present invention.
Figure 34:
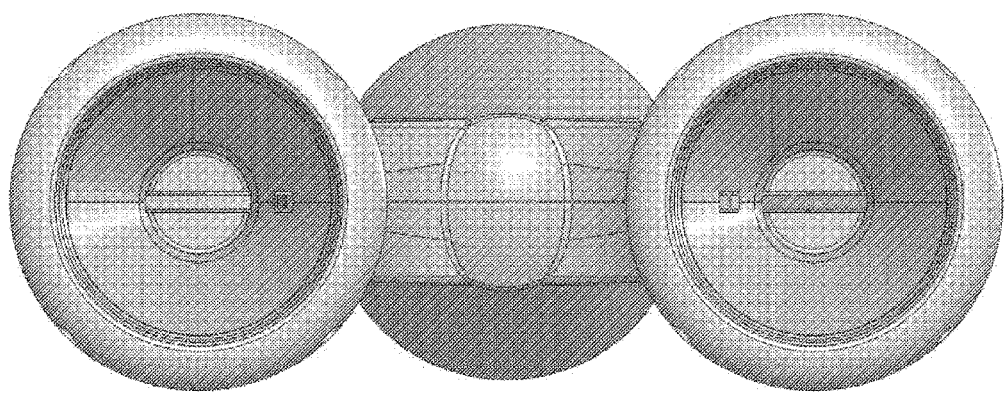
Figure 35:
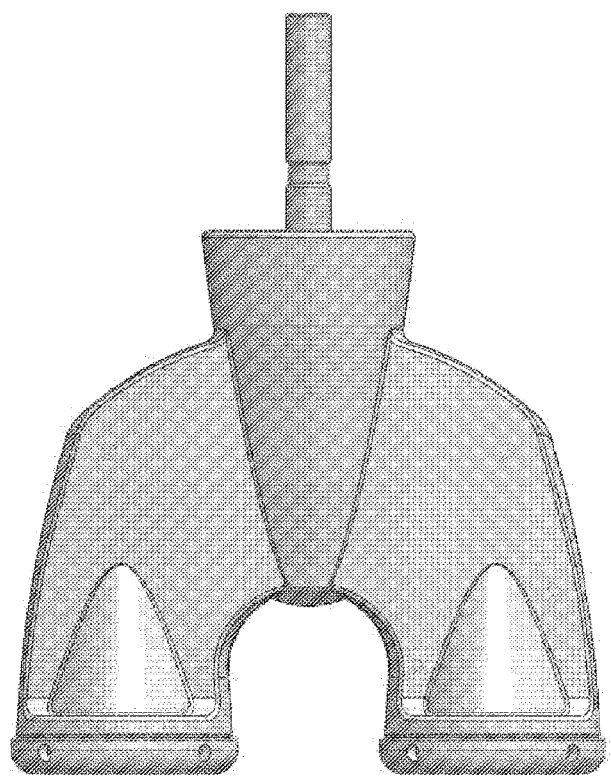
Figure 36:
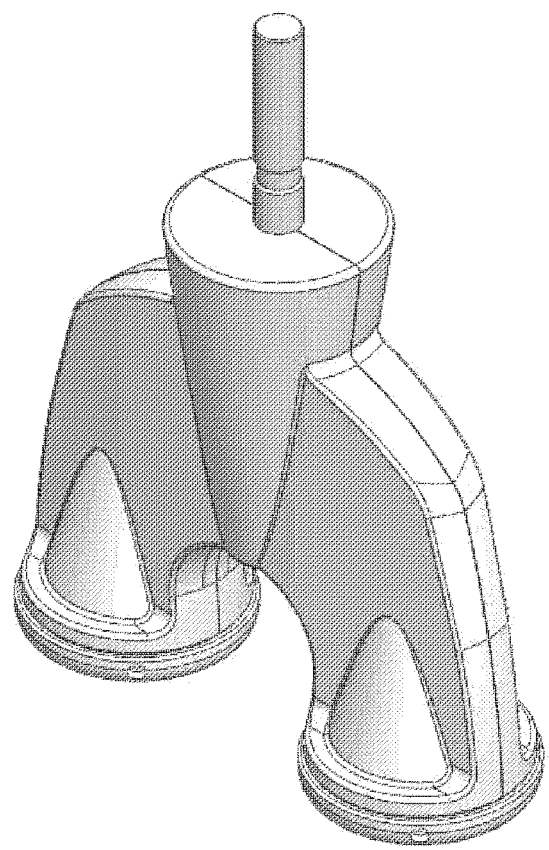
Figure 37:
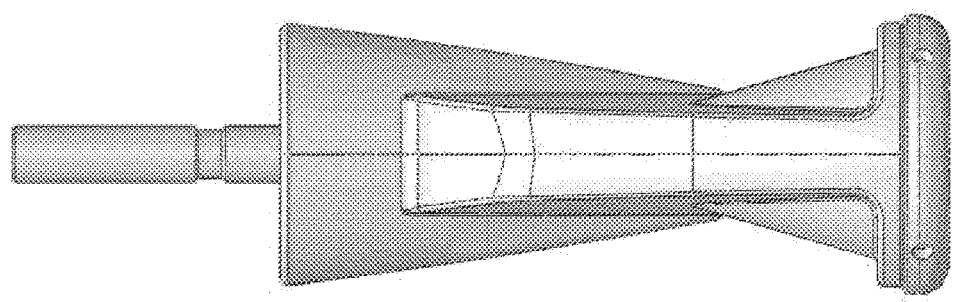
Figure 38:
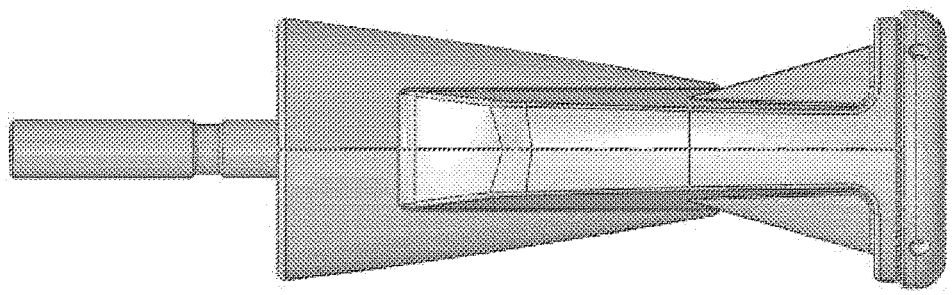
Figure 39:
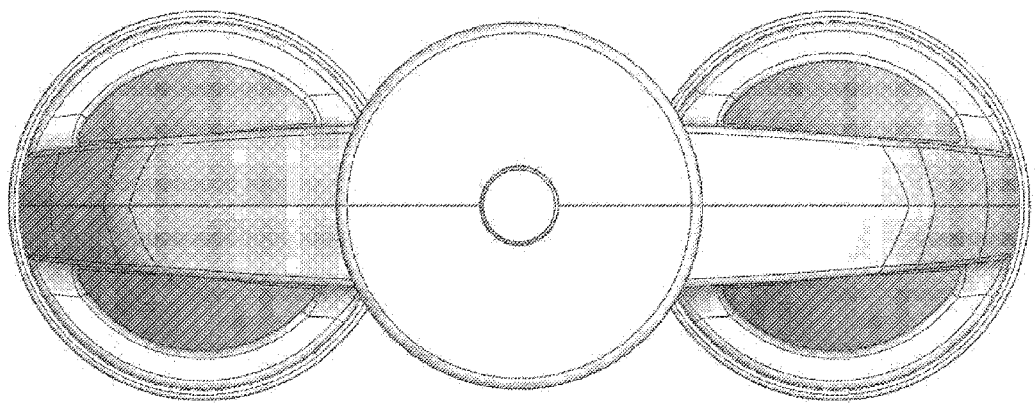
Figure 40:
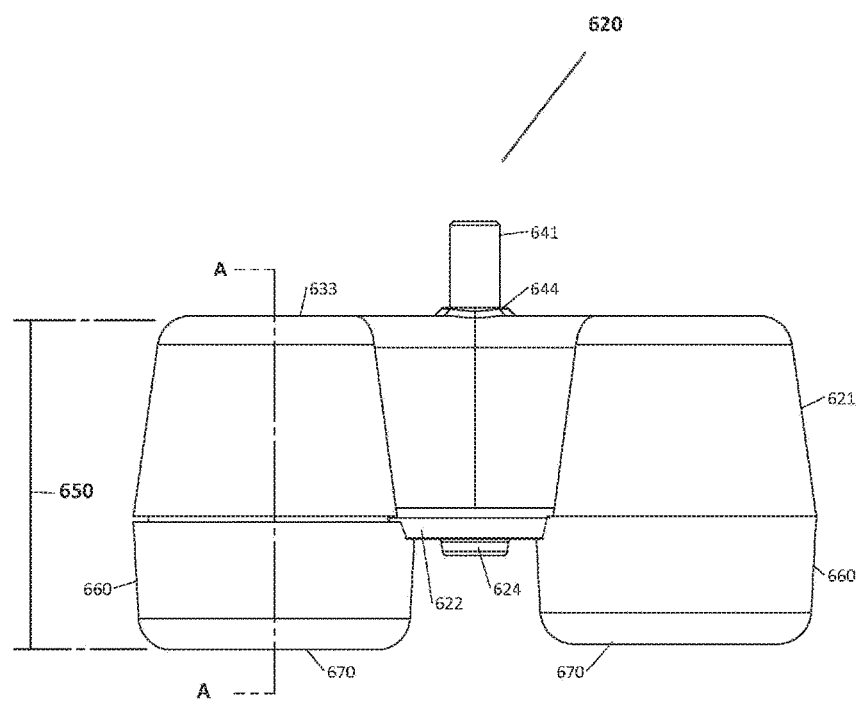
FIG. 40 is a side view of a third embodiment of the transfer device of the present invention.
Figure 69:
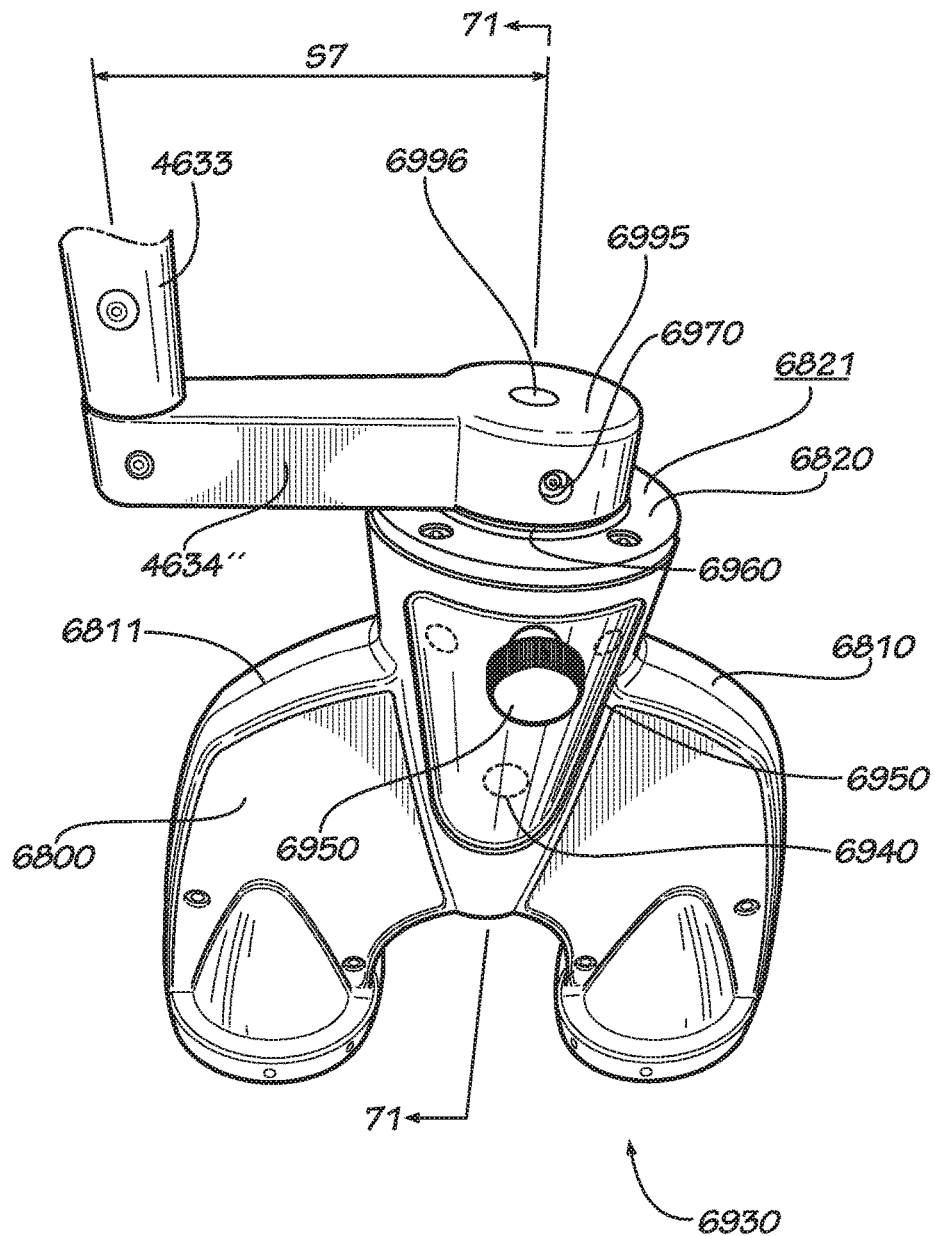
FIG. 69 is a side perspective view of another embodiment of the transfer device of FIG. 33.
Figure 70:
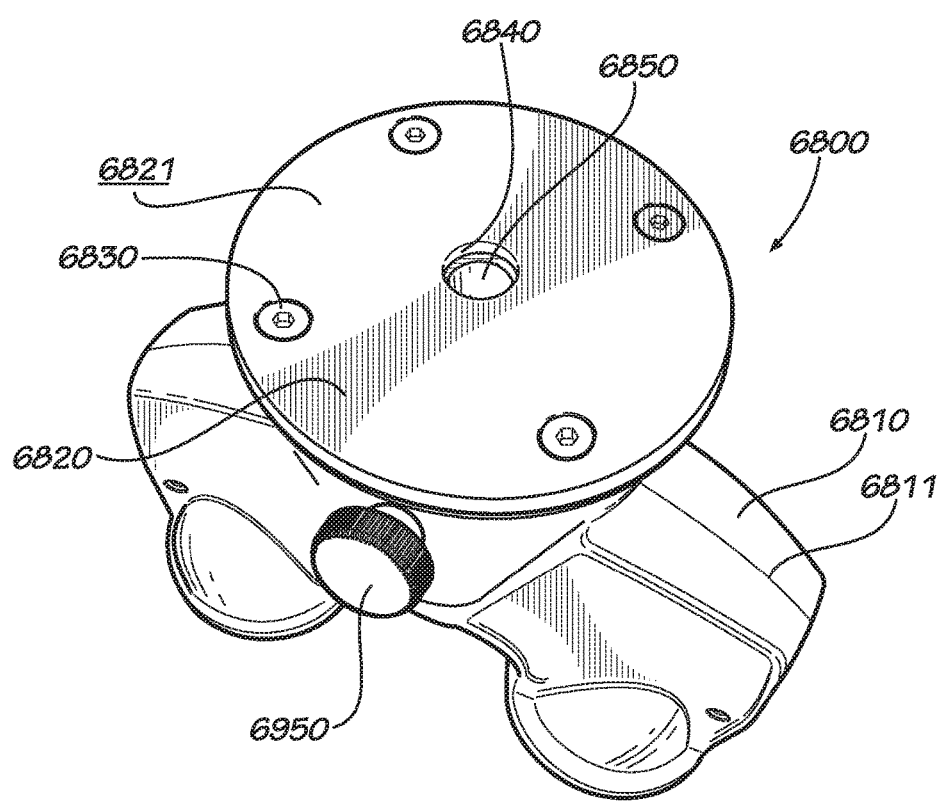
FIG. 70 is a top perspective view of the transfer device of FIG. 69.

FIGS. 69 and 70 show a transfer device 6800, which is another embodiment of the transfer device of FIG. 33. By incorporating an offset arm 4634" in transfer apparatus 6930 with an offset arm spacing S7 measured between a center of a shaft 6996 and a center of a pole 4633 of the patient care apparatus 4632, the patient care apparatus 4632 and embodiments thereof including embodiments with one or more IV pump loads can be more closely centered over the axis of the support platform. In various embodiments, the offset arm spacing S7 is between three inches and three and three-quarter inches. However, the disclosure of a specific range of values for offset arm spacing S7 should not be considered limiting. Because of the "clamshell" construction of transfer device 6800 described above, it can be advantageous in various embodiments to modify or retrofit the original design of the transfer device previously disclosed and shown in FIG. 33 by attaching a plate 6820 at the top end of the transfer device 6800, adding a washer 6960 between the offset arm 4634" and the plate 6820, re-drilling and tapping a plurality of holes 6940 defined in a housing 6810, reassembling the parts, and covering some or all of a side of the transfer device 6800 with a label 6950 to hide the fasteners and create an easily cleanable surface. Each of these modifications can be made to an existing transfer device such as the transfer device shown in FIG. 33. In various embodiments, the disclosed transfer device 6800 can be manufactured originally as shown without the necessity for later modification or retrofitting.

In various embodiments, the plate 6820 helps maintain the integrity of the transfer device 6800 by helping lock the two housing halves 6810a,b (shown in FIG. 71) together with a plurality of fasteners 6830 to close a housing seam 6811. The plate 6820 also provides a wide, flat surface 6821 on which a hub 6995 of the offset arm 4634" can rotate. In various embodiments, the hub 695 of offset arm 4634" defines one or more holes in which a fastener 6970—in various embodiments a set screw—secures offset arm 4634" to shaft 6996. In various embodiments, the plate 6820 defines a hole 6840 in the center to provide clearance for the shaft (not shown) to which the offset arm 4634" is connected).

In various embodiments, the thickness and diameter of plate 6820 may vary depending on the load that is to be supported and other factors. In various embodiments, the plate 6820 can be secured to the housing 6810 by a different type of fastener or quantity of fasteners than the plurality of fasteners 6830 shown. In various embodiments, one or more fasteners oriented in a plane parallel to and not perpendicular to the surface 6821 as shown, attach the plate 6820 to the housing 6810 by engaging one or more side surfaces (not shown) of the housing 6810 and a surface (not shown) of the plate 6820. In various such embodiments, the plate 6820 may have vertical flanges defining threads or one or more holes or keyhole slots for the purpose of attaching the plate 6820 to the housing 6810. The plate 6820 may resemble a cap in various embodiments.

In various embodiments, the washer 6960 separates the hub 6995 of offset arm 4634" from plate 6820 in order to prevent metal-to-metal contact. In various embodiments, holes 6940 on each side of housing 6810 are sized to fit a plurality of elongated-tip fasteners 6945 (shown in FIG. 71) to prevent a sleeve 6850 (shown in FIGS. 70-72) internal to the housing 6810 from sliding vertically, moving side to side, or rotating during rotation of the offset arm 4634". In various embodiments, the fasteners 6945 are ⁵⁄₁₆-24 set screws (i.e. ⁵⁄₁₆" in nominal diameter, twenty four threads per inch, with an internal hex head, and of various lengths as measured from the base of the head to the tip of the fastener). The disclosure of a specific style or size of fastener 6945, however, should not be considered limiting. In various embodiments, one or more of fasteners 6945 includes a knob 6950.

Figure 71:
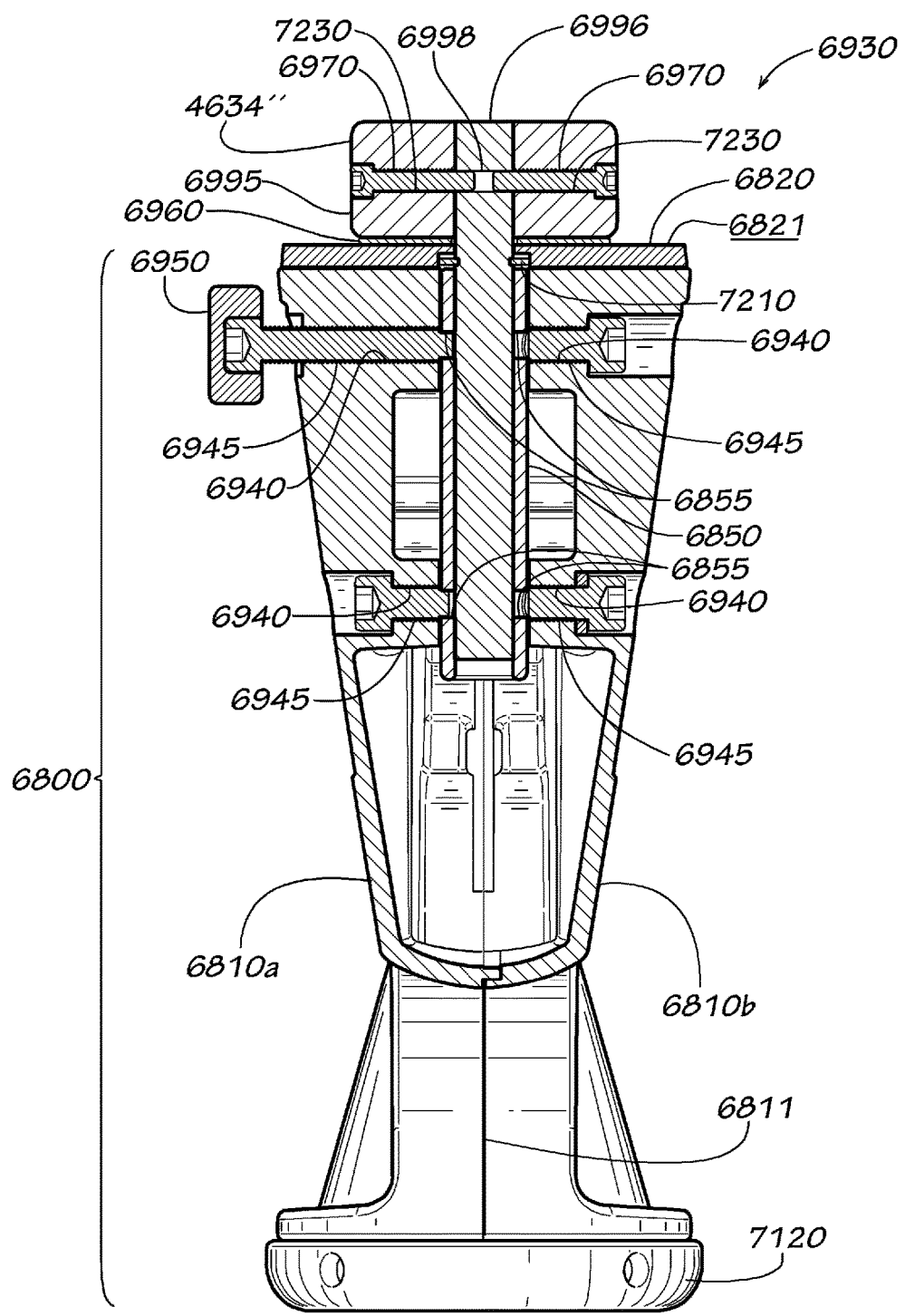
FIG. 71 is a sectional view of the transfer device of FIG. 69 taken along line 71-71 of FIG. 69.

FIG. 71 a sectional view of the transfer apparatus 6930 including transfer device 6800. In various embodiments, transfer device 6800 includes docking ring 7120. In various embodiments, sleeve 6850 is aligned with shaft 6996 and centered between housing halves 6810a and 6810b of housing 6810. In various embodiments as previously described, sleeve 6850 is held in place with one or more fasteners 6945. In various embodiments, a tip of one or more fasteners 6945 installed in holes 6940 at least partially engages holes 6955 of sleeve 6850 to secure sleeve 6850. One fastener 6945 is shown with the aforementioned knob 6950. In various embodiments, the tip of one or more fasteners 6945 extends to an outer surface of shaft 6996 such that the tightening of fastener 6945 fixes the rotational position of shaft 6996 with respect to housing 6810 of transfer device 6800. In various embodiments, retaining ring 7210 is positioned in groove 6997 (shown in FIG. 72) of shaft 6996 below plate 6820. In various embodiments, one or more fasteners 6970 are positioned in one or more holes 7230 of offset arm 4634" and extend at least partially into hole 6998 of shaft 6996 above plate 6820. In various embodiments, the assembly of fasteners 6970 above plate 6820 and the assembly of retaining ring 7210 below plate 6820 holds together each component of a patient care apparatus kit 7200 (shown in FIGS. 72 and 73). Consequently, the patient care apparatus kit 7200 can be prepared and assembled to transfer device 6800 as a self-contained subassembly including in the field as may be desired to update a transfer device 6800 that for whatever reason does not already include one or more features inherent in the patient care apparatus kit 7200.

Figure 72:
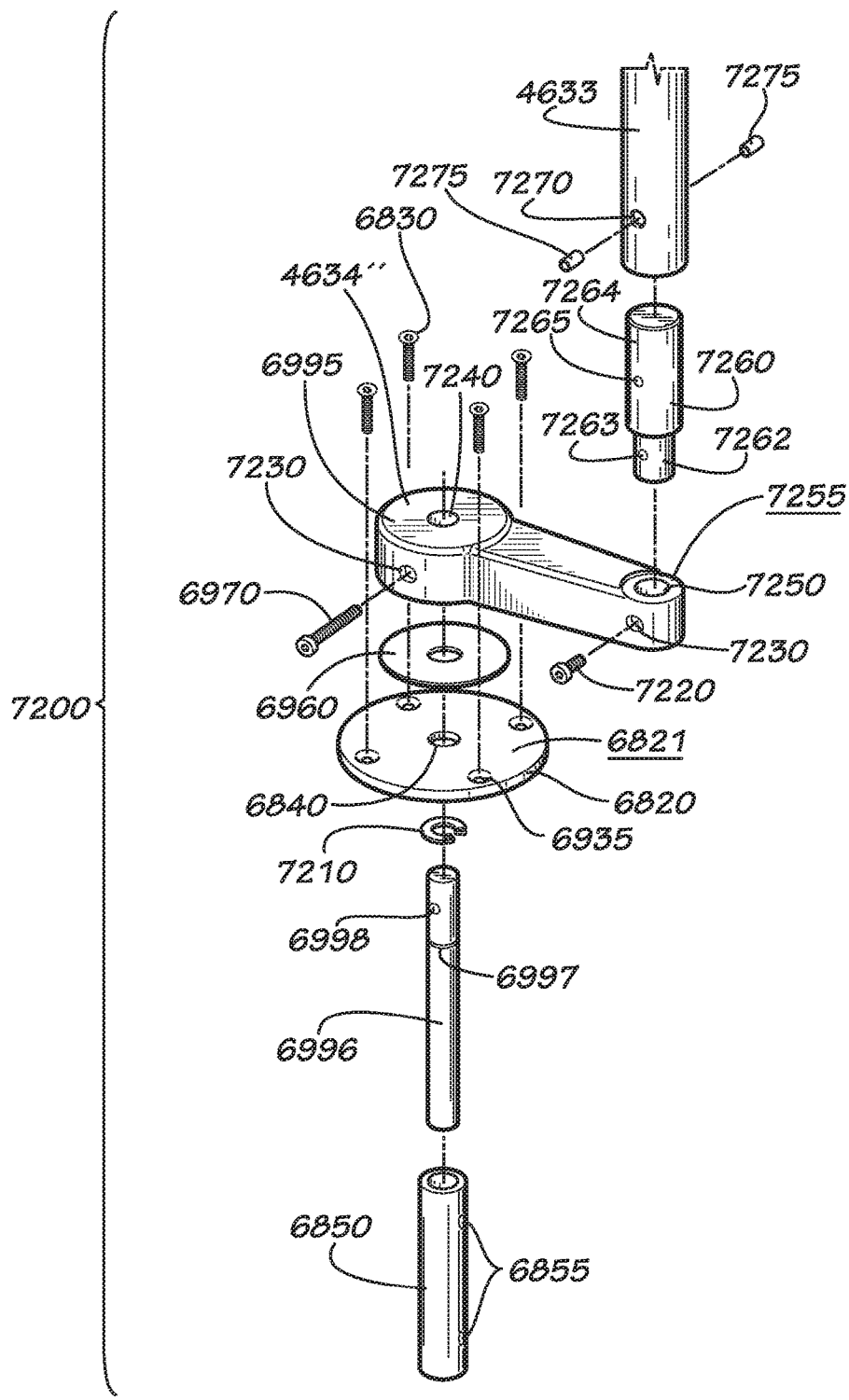
FIG. 72 is an exploded view of a single-pole patient care apparatus kit for use with the transfer device of FIG. 33.

FIG. 72 shows an exploded view of a single-pole version of the patient care apparatus kit 7200. Sleeve 6850, shaft 6996, retaining ring 7210, plate 6820, and washer 6960 are aligned with—in preparation for assembly in—hole 7240 of offset arm 4634". In various embodiments, shaft 6996 is shown with groove 6997 to receive retaining ring 7210 and hole 6998 to receive one or more fasteners 6970. Fasteners 6830—countersunk in the current embodiments so as to remain flush with plate 6820—are aligned with mating holes 6935 of plate 6820. Pole 4633 and a pole adapter 7260 are shown aligned with—in preparation for assembly in—a hole 7250 of offset arm 4634". In various embodiments, pole 4633 is shown with one or more holes 7270 to align with one or more holes 7265 in an upper portion 7264 of pole adapter 7260 when assembled to upper portion 7264 of adapter 7260 with fasteners 7275. In various embodiments, offset arm 4634" is shown with one or more holes 7230 to align with one or more holes 7263 in a lower portion 7262 of pole adapter 7260 when assembled to lower portion 7262 of adapter 7260 with one or more fasteners 7220. In various embodiments, the offset arm 4634" includes a surface 7255 to facilitate the orthogonal positioning of an axis of pole 4633 with respect to offset arm 4634".

Figure 73:
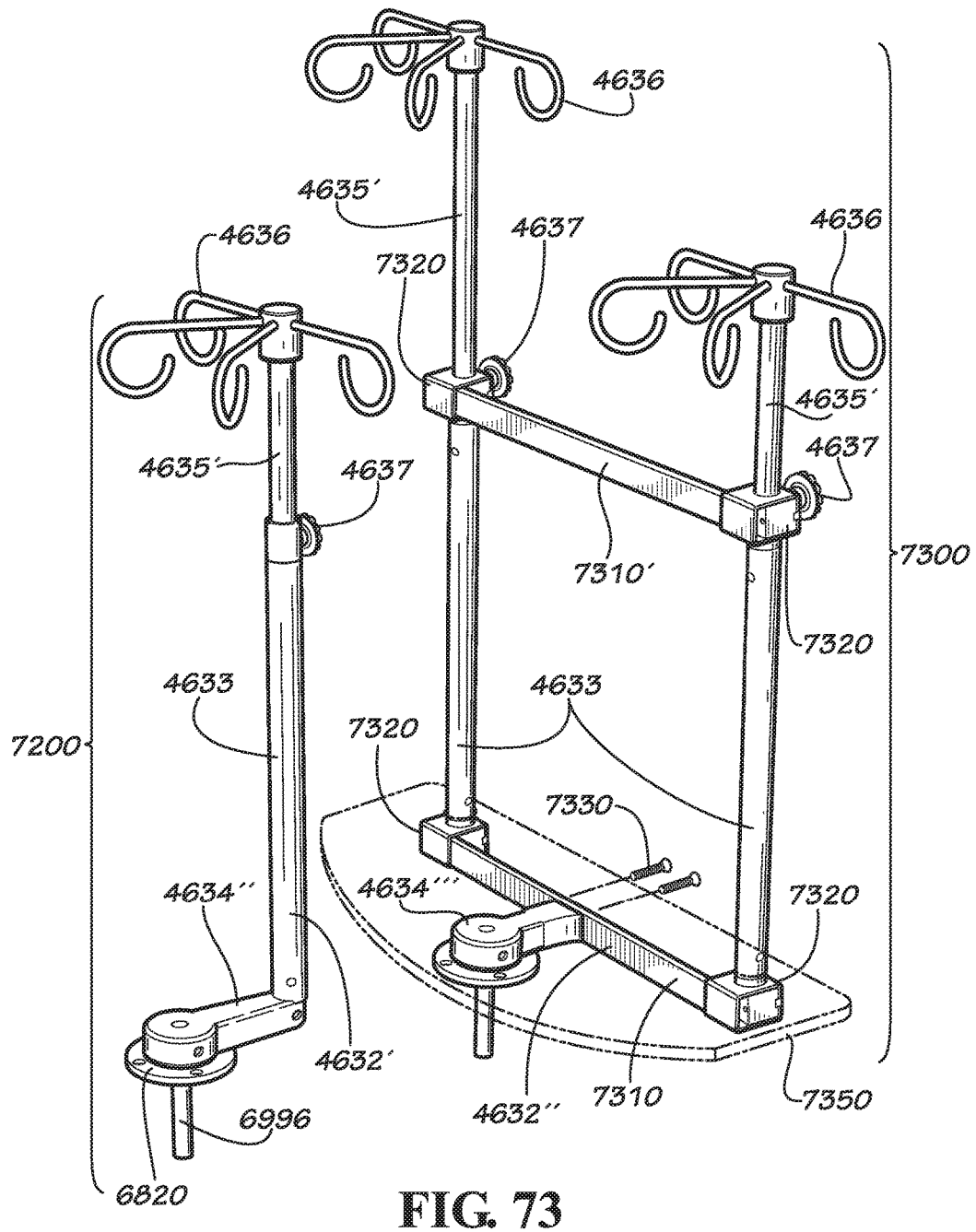
FIG. 73 is a perspective view of each of two embodiments of a patient care apparatus kit, one being the single-pole embodiment of FIG. 72 and one being another embodiment including multiple poles.

In part, FIG. 73 discloses the single-pole version of the patient care apparatus kit 7200 as assembled. In various embodiments, the patient care apparatus kit 7200 includes a patient care apparatus 4632', the plate 6820, the shaft 6996, and various other components previously described as being included in the patient care apparatus kit 7200. In various embodiments, the patient care apparatus 4632' includes an offset arm 4634" and a pole 4633 that is an IV pole in the current embodiment. In various embodiments, the patient care apparatus 4632' includes a top portion 4635' and adjustment knob 4637 to allow the top portion 4635' to be raised or lowered with respect to the pole 4633. In various embodiments, top portion 4635' includes hooks 4636, shown in a different configuration than that shown in the top portion 4635 of FIG. 46. As previously noted, hooks 4636 can take on any number of different shapes and are not limited to the "rams-horn" style shown. In various embodiments, the quantity and placement of hooks 4636 varies from that shown. In various embodiments, offset arm 4634" includes ball detents (not shown) similar to ball detents 5394 shown in FIG. 53 in order to increase the resistance against rotation of offset arm 4634" or to provide set angular positions at which offset arm 4634" can be "indexed" or rotated in pre-set increments. In various embodiments, resistance against rotation of offset arm 4634" is accomplished by incorporating a brake mechanism such as the shaft brake mechanism 5200 shown in transfer device 4631'.

In part, FIG. 73 also discloses a multi-pole version of the patient care apparatus kit in the embodiment of a patient care apparatus kit 7300. In various embodiments, the patient care apparatus kit 7300 includes a patient care apparatus 4632" and the same components previously described as being included in the patient care apparatus kit 7200 with the exception of offset arm 4634" and the components connecting offset arm 4634" to pole 4633. In various embodiments, the patient care apparatus 4632" includes an offset arm 4634''' and a lower rail 7310 secured to offset arm 4634''' with one or more fasteners 7330—countersunk in the current embodiment. In various embodiments, the patient care apparatus 4632" additionally includes a plurality of poles 4633, each connected to the lower rail 7310 and to an upper rail 7310' using a plurality of connectors. In various embodiments, connectors 7320 are slidably attached to rail 7310, 7310' and locked to the rails by set screws at the desired spacing of poles 4633. Two or more poles can thus be attached to rails 7310,7310'. In various embodiments, a shelf 7350 is placed on the top surface of an offset arm such as the offset arm 4634''' and in some embodiments fastened by screws or other mechanisms known in the art in order to provide a temporary support during installation of the patient care device 4638 to poles 4633 or rails 7310,7310' of a patient care apparatus such as the patient care apparatus 4632''' so as to help users to install the patient care device 4638 patient care apparatus so that the center of gravity of the patient care device 4638 is centered approximately over the axis of support shaft 6996. The shelf 7350 may be made of an opaque or translucent material but in various embodiments is made from a material that is easily cleanable. In various embodiments, the shelf 7350 is removable from the patient care apparatus 4632''' including for cleaning In various embodiments, the patient care apparatus 4632" additionally includes the top portion 4635' and adjustment knob 4637 to allow the top portion 4635' to be raised or lowered with respect to the remaining portion of the patient care apparatus 4632". In various embodiments, top portion 4635' includes hooks 4636. In various embodiments, the quantity and placement of rails 7310,7310', poles 4633, connectors 7320, or top portions 4635' including hooks 4636 varies from that shown. By changing the length or position of one or more of the aforementioned components of the patient care apparatus 4632", various types of equipment can be secured to the patient care apparatus 4632".

In the current embodiment, the end of offset arm 4634''' distal to where shaft 6996 is attached includes a vertical surface in which holes (not shown) are defined and in which fasteners 7330 are secured. In various embodiments, offset arm 4634''' includes ball detents (not shown) similar to ball detents 5394 shown in FIG. 53 in order to increase the resistance against rotation of offset arm 4634''' or to provide set angular positions at which offset arm 4634''' can be "indexed" or rotated in pre-set increments. In various embodiments, resistance against rotation of offset arm 4634''' is accomplished by incorporating a brake mechanism such as the shaft brake mechanism 5200 shown in transfer device 4631'.

In various embodiments, one or more features or elements of the patient care apparatus 4632' or 4632" are incorporated into transfer system 4600 with transfer device 4631 or 4631'. Because the offset arm 4634',4634",4634''' can vary between various embodiments of various parts of transfer system 4600, various embodiments of the patient care apparatus 4632,4632',4632" can be coupled with various embodiments of transfer device 4631,4631',6800 and various other transfer devices including transfer devices of an older design that are already in use by customers.

In various embodiments where the transfer system 4600 includes a transfer device 4631', the transfer device 4631' includes the support shaft 4996 and a shaft brake mechanism 5200 including shaft brake assembly 6200. In various embodiments, a shaft brake mechanism (not shown) will include the embodiment reflected in shaft brake assembly 7000. In various embodiments, the shaft brake mechanism 5200 is engageable with the support shaft 4996, a method of using the transfer system 4600 includes disengaging the shaft brake mechanism 5200 by hand; rotating the support shaft 4996; and re-engaging the shaft brake mechanism 5200 by hand. In various embodiments where the transfer system 4600 further includes a receiver arm 4614 attachable to a mobile support platform 4650 and receivable by the transfer device 4631' and an arm brake mechanism 4730 engageable with an arm portion 4840 of the receiver arm 4652, the method further includes disengaging the arm brake mechanism 4730 by hand, rotating the arm portion 4840; and re-engaging the arm brake mechanism 4730 by hand. In various embodiments where the transfer device 4631' is mounted to a mobile support platform 4650, the method further includes maintaining the angular orientation of the transfer device 4631' relative to the mobile support platform 4650 while moving the mobile support platform 4650. In various embodiments where the receiver arm 4652 includes a receiver 4615' and the receiver includes a plurality of pawls 6570, the method further comprises rotationally dampening the receiver arm 4652 within a docking cup 5050 of the transfer device 4631'.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described.

One should note that conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more particular embodiments or that one or more particular embodiments necessarily include logic for deciding, with or without user input or prompting, whether these features, elements and/or steps are included or are to be performed in any particular embodiment.

It should be emphasized that the above-described embodiments are merely possible examples of implementations, merely set forth for a clear understanding of the principles of the present disclosure. Any process descriptions or blocks in flow diagrams should be understood as representing modules, segments, or portions of code which include one or more executable instructions for implementing specific logical functions or steps in the process, and alternate implementations are included in which functions may not be included or executed at all, may be executed out of order from that shown or discussed, including substantially concurrently or in reverse order, depending on the functionality involved, as would be understood by those reasonably skilled in the art of the present disclosure. Many variations and modifications may be made to the above-described embodiment(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

That which is claimed is:

1. A transfer system for a patient care apparatus, the transfer system comprising:

a transfer device including a first docking cup and a second docking cup, each of the first docking cup and the second docking cup aligned with a vertical axis, defining a conical surface aligned with the vertical axis, and sized to accept a receiver; and a security mechanism enclosed within the transfer device and including a first security lever and a second security lever, the first security lever positioned to disengage a first receiver in the first docking cup when a second receiver is received within the second docking cup, and the second security lever positioned to disengage the second receiver in the second docking cup when the first receiver is received within the first docking cup.

2. The transfer system of claim 1, wherein the first docking cup includes a rotation-dampening element.

3. The transfer system of claim 2, wherein the rotation-dampening element is replaceable.

4. The transfer system of claim 2, further comprising a receiver, a surface of the receiver defining a relief and the rotation-dampening element extending radially inward from the inner surface of the docking cup.

5. The transfer system of claim 1, further comprising a first biasing element engaging the first security lever, and a second biasing element engaging the second security lever.

6. The transfer system of claim 5, wherein each of the first docking cup, the second docking cup, the first security lever, the second security lever, the first biasing element, and the second biasing element is formed from a magnetic-resonance-safe (MR-safe) material.

7. The transfer system of claim 1, further comprising a support shaft and an offset arm, the support shaft disposed between the first docking cup and the second docking cup of the transfer device, the offset arm coupled to the support shaft.

8. The transfer system of claim 1, further comprising a support shaft disposed between the first security lever and the second security lever of the transfer device.

9. The transfer system of claim 7, wherein the transfer device further includes a housing and a plate attached to the housing between the housing and the offset arm.

10. The transfer system of claim 1, further comprising a receiver configured to be inserted into the first docking cup or the second docking cup along a vertical axis and to support the weight of the transfer device, the receiver integrally formed as a single part.

11. The transfer system of claim 1, further comprising a receiver arm, the receiver arm integrally formed as a single part.

12. The transfer system of claim 1, further comprising a receiver arm and an arm brake mechanism, the arm brake mechanism including a brake shaft, a brake spacer, and an arm brake fastener, the brake spacer coupled to the brake shaft so at to rotate together.

13. The transfer system of claim 12, wherein the brake spacer is coupled to the brake shaft with a fastener.

14. The transfer system of claim 12, wherein the brake spacer includes a conical surface, the receiver arm includes a conical surface, and the arm brake fastener includes a threaded portion, the conical surface of the brake spacer, the conical surface of the receiver arm, and the threaded portion of the arm brake fastener being coaxial.

15. The transfer system of claim 1, further comprising a receiver, a side surface of the lower portion of the receiver having a concave shape.

16. The transfer system of claim 1, wherein each of the first docking cup and the second docking cup define a pivot slot and wherein each of the first security lever and the second security lever include a pivot pin, the pivot pin of the first security lever rotatable within the pivot slot of the first docking cup and the pivot pin of the second security lever rotatable within the pivot slot of the second docking cup.

17. The transfer system of claim 16, wherein the transfer device further includes a housing, the housing defining a security aperture, a curvature of a lower surface of the first security lever co-radial with a lower edge surface of the housing, the lower edge surface of the housing in supportive contact with the lower surface of the first security lever when the transfer device is lifted relative a receiver when the receiver is engaged in the first docking cup.

18. A transfer device for a patient care apparatus comprising:
   a first docking cup and a second docking cup, each of the first docking cup and the second docking cup aligned with a vertical axis, defining a conical surface aligned with the vertical axis, and sized to receive a receiver; and
   a security mechanism enclosed within the transfer device, the security mechanism including a first security lever and a second security lever, the first security lever including a biasing element, the biasing element vertically offset upward from the first security lever.

19. The transfer device of claim 18, further comprising a support shaft and a shaft brake mechanism engageable with the support shaft.

20. The transfer device of claim 19, wherein the shaft brake mechanism includes a brake fastener, and wherein the brake fastener is tightenable.

21. The transfer device of claim 20, wherein the brake fastener includes a knob.

22. The transfer device of claim 19, wherein the shaft brake mechanism includes a brake disc, a plate, and a brake fastener, the brake fastener increasing a force holding the brake disc to the plate when the brake fastener is tightened.

23. The transfer device of claim 18, further comprising a support shaft and a multi-pole offset arm, the support shaft disposed between the first docking cup and the second docking cup of the transfer device, the multi-pole offset arm coupled to the support shaft.

24. The transfer device of claim 18, further comprising a support shaft and an offset arm and a patient care device, the support shaft disposed between the first docking cup and the second docking cup of the transfer device, the offset arm coupled to the support shaft, and an offset arm spacing of the offset arm such that a center of gravity of the patient care apparatus is substantially aligned vertically with and above a support shaft of the transfer device.

25. The transfer device of claim 18, wherein all exposed upper exterior surfaces of the transfer device are vertical or sloped.

26. The transfer device of claim 18, wherein the biasing element is a compression spring.

27. The transfer device of claim 18, wherein the first security lever is formed using an additive manufacturing process.

* * * * *